US009276218B2

(12) United States Patent
Kim et al.

(10) Patent No.: US 9,276,218 B2
(45) Date of Patent: Mar. 1, 2016

(54) ARYLAMINE COMPOUND AND ORGANIC LIGHT-EMITTING DEVICE COMPRISING SAME

(71) Applicant: SAMSUNG DISPLAY CO., LTD., Yongin, Gyeonggi-do (KR)

(72) Inventors: Soo-Yon Kim, Yongin (KR); Seok-Hwan Hwang, Yongin (KR); Young-Kook Kim, Yongin (KR); Hye-Jin Jung, Yongin (KR); Jin-O Lim, Yongin (KR); Sang-Hyun Han, Yongin (KR); Eun-Jae Jeong, Yongin (KR); Jun-Ha Park, Yongin (KR); Eun-Young Lee, Yongin (KR); Jong-Hyuk Lee, Yongin (KR)

(73) Assignee: Samsung Display Co., Ltd., Samsung-ro, Giheung-Gu, Yongin-si, Gyeonggi-Do (KR)

( * ) Notice: Subject to any disclaimer, the term of this patent is extended or adjusted under 35 U.S.C. 154(b) by 342 days.

(21) Appl. No.: 14/016,316

(22) Filed: Sep. 3, 2013

(65) Prior Publication Data

US 2014/0175398 A1 Jun. 26, 2014

(30) Foreign Application Priority Data

Dec. 26, 2012 (KR) ........................ 10-2012-0153570

(51) Int. Cl.

*H01L 51/00* (2006.01)
*C07D 405/14* (2006.01)

(Continued)

(52) U.S. Cl.

CPC ............ *H01L 51/006* (2013.01); *C07D 209/56* (2013.01); *C07D 405/14* (2013.01); *H01L 51/0061* (2013.01); *H01L 51/0072* (2013.01); *H01L 51/0073* (2013.01);

(Continued)

(58) Field of Classification Search

None

See application file for complete search history.

(56) References Cited

U.S. PATENT DOCUMENTS

| | | | |
|---|---|---|---|
| 3,968,051 | A | 7/1976 | Stamm et al. |
| 6,465,115 | B2 | 10/2002 | Shi et al. |
| 6,596,415 | B2 | 7/2003 | Shi et al. |
| 7,053,255 | B2 | 5/2006 | Ikeda et al. |

(Continued)

FOREIGN PATENT DOCUMENTS

KR 10-2006-0006760 A 1/2006

OTHER PUBLICATIONS

Sigma-Aldrich. 4H-benzoldeflcarbazole, printed on Nov. 4, 2015 from www.sigmaaldrich.com A novel conjugated polymer based on 4H-benzo[def]carbazole backbone for OLED, 2009 Fall Assembly and Symposium, 2009, vol. 34, No. 2.

*Primary Examiner* — J. L. Yang

(74) *Attorney, Agent, or Firm* — Robert E. Bushnell, Esq.

(57) ABSTRACT

An arylamine compound of Formula 1 below and an organic light-emitting device including the arylamine compound are provided:

<Formula 1>

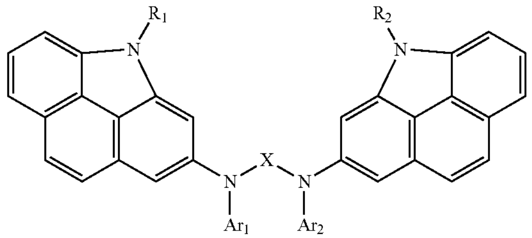

Substituents in Formula 1 are as defined in the specification.

20 Claims, 1 Drawing Sheet

(51) Int. Cl.
*C07D 209/56* (2006.01)
*H01L 51/50* (2006.01)

(52) U.S. Cl.
CPC ........ *H01L 51/0052* (2013.01); *H01L 51/0059* (2013.01); *H01L 51/0077* (2013.01); *H01L 51/5012* (2013.01); *H01L 51/5056* (2013.01); *H01L 51/5088* (2013.01)

(56) References Cited

U.S. PATENT DOCUMENTS

| | | | | |
|---|---|---|---|---|
| 7,233,019 | B2 | 6/2007 | Ionkin et al. | |
| 7,571,894 | B2 | 8/2009 | Sotoyama | |
| 2014/0110675 | A1 * | 4/2014 | Kim ..................... | C07D 401/10 257/40 |

* cited by examiner

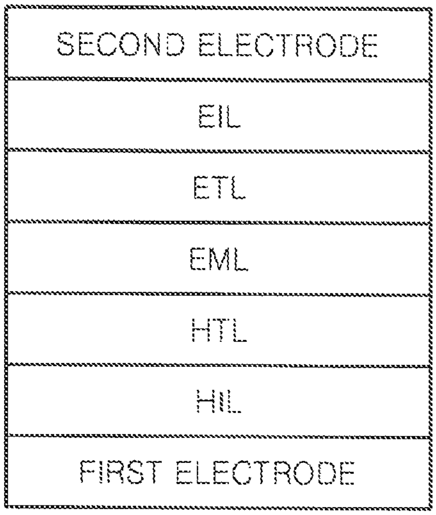
SECOND ELECTRODE
EIL
ETL
EML
HTL
HIL
FIRST ELECTRODE

ARYLAMINE COMPOUND AND ORGANIC LIGHT-EMITTING DEVICE COMPRISING SAME

CLAIM OF PRIORITY

This application makes reference to, incorporates the same herein, and claims all benefits accruing under 35 U.S.C. §119 from an application for ARYLAMINE COMPOUND AND ORGANIC LIGHT-EMITTING DEVICE COMPRISING SAME earlier filed in the Korean Intellectual Property Office on 26 Dec. 2012 and there duly assigned Serial No. 10-2012-0153570.

BACKGROUND OF THE INVENTION

1. Field of the Invention

One or more embodiments of the present invention relate to an arylamine compound and an organic light-emitting device including the arylamine compound.

2. Description of the Related Art

Organic light-emitting devices (OLEDs), which are self-emitting devices, have advantages such as wide viewing angles, excellent contrast, quick response, high brightness, excellent driving voltage characteristics, and can provide multicolored images.

A typical OLED has a structure including a substrate, and an anode, a hole transport layer (HTL), an emission layer (EML), an electron transport layer (ETL), and a cathode which are sequentially stacked on the substrate. In this regard, the HTL, the EML, and the ETL are organic thin films formed of organic compounds.

An operating principle of an OLED having the above-described structure is as follows.

When a voltage is applied between the anode and the cathode, holes injected from the anode move to the EML via the HTL, and electrons injected from the cathode move to the EML via the ETL. The holes and electrons recombine in the EML to generate excitons. When the excitons drop from an excited state to a ground state, light is emitted.

There has been an ongoing demand for a material having improved electrical stability, high charge-transfer or emission capability, and a high glass transition temperature that is high enough to prevent crystallization, in regards to existing unimolecular materials.

SUMMARY OF THE INVENTION

One or more embodiments include a novel compound that has improved electrical characteristics, improved charge transporting capability, improved emission capability, and a high glass transition temperatures (Tg) enough to prevent crystallization, and thus is suitable as an electron transporting or electron injecting material for fluorescent or phosphorescent devices of any color of red, green, blue, or white.

Additional aspects will be set forth in part in the description which follows and, in part, will be apparent from the description, or may be learned by practice of the presented embodiments.

According to one or more embodiments of the present invention, there is provided an arylamine compound represented by Formula 1 below:

<Formula 1>

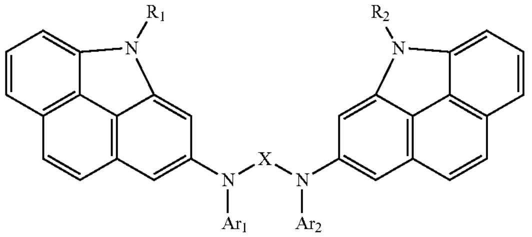

wherein, in Formula 1,

X is a substituted or unsubstituted C6-C60 arylene group, a substituted or unsubstituted C2-C60 heteroarylene group, a substituted or unsubstituted C6-C60 polycyclic group, or a divalent linking group with at least two of the arylene group, the heteroarylene group, and the polycyclic group liked together;

$R_1$ and $R_2$ are each independently a substituted or unsubstituted C1-C60 alkyl group, a substituted or unsubstituted C3-C60 cycloalkyl group, a substituted or unsubstituted C6-C60 aryl group, a substituted or unsubstituted C2-C60 heteroaryl group, a substituted or unsubstituted C6-C60 polycyclic group, or a cyano group; and $Ar_1$ and $Ar_2$ are each independently a substituted or unsubstituted C6-C60aryl group, a substituted or unsubstituted C2-C60 heteroaryl group, or a substituted or unsubstituted C6-C60 polycyclic group.

According to one or more embodiments of the present invention, an organic light-emitting device includes: a first electrode; a second electrode; and an organic layer disposed between the first electrode and the second electrode, the organic layer including the aryamine compound of Formula 1 above.

According to one or more embodiments of the present invention, a flat panel display device includes the above-described organic light-emitting device, wherein the first electrode of the organic light-emitting device is electrically connected to a source electrode or a drain electrode of a thin-film transistor.

BRIEF DESCRIPTION OF THE DRAWING

A more complete appreciation of the invention, and many of the attendant advantages thereof, will be readily apparent as the same becomes better understood by reference to the following detailed description when considered in conjunction with the accompanying drawings in which like reference symbols indicate the same or similar components, wherein:

FIG. 1 schematically illustrates the structure of an organic light-emitting device according to an embodiment of the present invention.

DETAILED DESCRIPTION OF THE INVENTION

Reference will now be made in detail to embodiments, examples of which are illustrated in the accompanying drawings, wherein like reference numerals refer to the like elements throughout. In this regard, the present embodiments may have different forms and should not be construed as being limited to the descriptions set forth herein. Accordingly, the embodiments are merely described below, by referring to the figures, to explain aspects of the present description. As used herein, the term “and/or” includes any and all combinations of one or more of the associated listed items.

Expressions such as "at least one of," when preceding a list of elements, modify the entire list of elements and do not modify the individual elements of the list.

According to an embodiment of the present invention, there is provided an organic light-emitting compound represented by Formula 1 below:

<Formula 1>

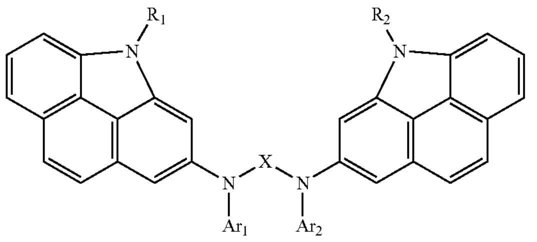

In Formula 1, X is a substituted or unsubstituted C6-C60 arylene group, a substituted or unsubstituted C2-C60 heteroarylene group, a substituted or unsubstituted C6-C60 polycyclic group, or a divalent linking group with at least two of an arylene group, a heteroarylene group, and a polycyclic group liked together;

$R_1$ and $R_2$ are each independently a substituted or unsubstituted C1-C60 alkyl group, a substituted or unsubstituted C3-C60 cycloalkyl group, a substituted or unsubstituted C6-C60 aryl group, a substituted or unsubstituted C2-C60 heteroaryl group, a substituted or unsubstituted C6-C60 polycyclic group, or a cyano group; and $Ar_1$ and $Ar_2$ are each independently a substituted or unsubstituted C6-C60 aryl group, a substituted or unsubstituted C2-C60 heteroaryl group, or a substituted or unsubstituted C6-C60 polycyclic group.

In some embodiments the arylamine compound of Formula 1 may be used as a hole transporting material, a hole injecting material, or a light-emitting material.

The arylamine compound of Formula 1 has a high glass transition temperature (Tg) or melting point due to the introduction of the heterocyclic group. Thus, the arlyamine compound has high heat resistance against Joule's heat generated in an organic layer, between organic layers, or between an organic layer and a metal electrode when light emission occurs, and has high durability in high-temperature environments. Accordingly, an organic light-emitting device manufactured using the arylamine compound of Formula 1 may have high durability when stored or operated.

Substituents in the arylamine compound of Formula 1 will now be described in detail.

In some embodiments, $R_1$ and $R_2$ in Formula 1 may be each independently a substituted or unsubstituted C1-C30 alkyl group or

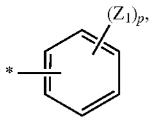

wherein $Z_1$ is a hydrogen atom, a deuterium atom, a substituted or unsubstituted C1-C20 alkyl group, a substituted or unsubstituted C5-C20 aryl group, a substituted or unsubstituted C2-C20 heteroaryl group, or a substituted or unsubstituted C6-C20 polycyclic group; p is an integer from 1 to 5; and * indicates a binding site In some embodiments, X in Formula 1 may be a group represented by one of Formulae 2a to 2m below:

In Formulae 2a to 2m, $Y_1$ is CH or N;

$Q_1$ is a linking group represented by $—C(R_{30})(R_{31})—$, $—NR_{32}—$, $—Si(R_{33})(R_{34})—$, —S—, or —O—;

$R_{30}$ to $R_{34}$, and $Z_1$ are each independently, a hydrogen atom, a deuterium atom, a substituted or unsubstituted C1-C20 alkyl group, a substituted or unsubstituted C5-C20 aryl group, a substituted or unsubstituted C6-C20 polycyclic group, wherein $R_{30}$ and $R_{31}$ are optionally linked to each other to form a ring;

p is an integer from 1 to 8; and * indicates a binding site.

In some other embodiments, $Ar_1$ and $Ar_2$ in Formula 1 may be each independently a group represented by one of Formulae 3a to 3c below:

2a

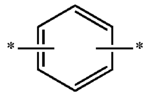

2b

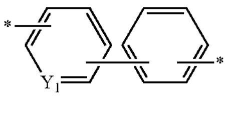

2c

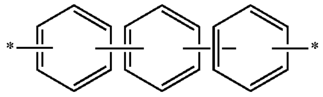

2d

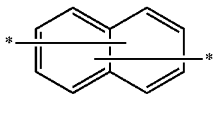

2e

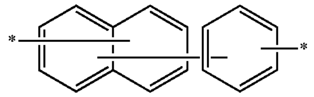

2f

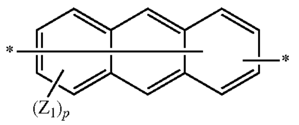

2g

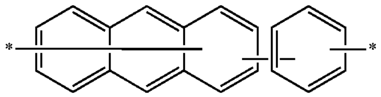

2h

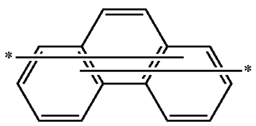

2i

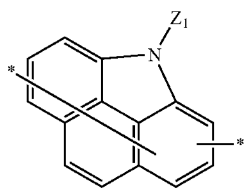

-continued

2j

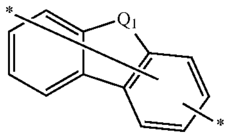

2k

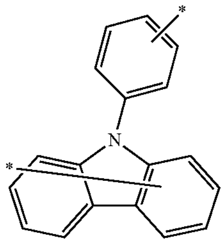

2l

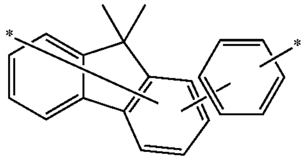

2m

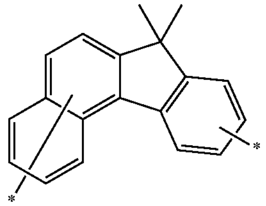

3a

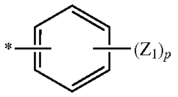

3b

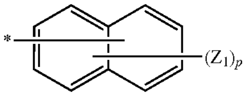

3c

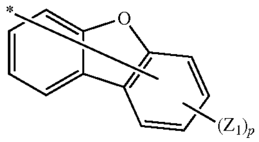

In Formulae 3a to 3c, $Z_1$ is a hydrogen atom, a deuterium atom, a substituted or unsubstituted C1-C20 alkyl group, a substituted or unsubstituted C5-C20 aryl group, an amino group substituted with a substituted or unsubstituted C5-C20 aryl group, or a substituted or unsubstituted C6-C20 polycyclic group;

p is an integer from 1 to 7; and * indicates a binding site.

In some other embodiments, $Ar_1$ and $Ar_2$ in Formula 1 may be linked to each other directly or via an adjacent substituent.

In some other embodiments, $R_1$ and $R_2$ in Formula 1 may be the same.

Hereinafter, substituents described with reference to the formulae will now be described in detail. In this regard, the numbers of carbons in substituents are presented only for illustrative purposes and do not limit the characteristics of the substituents. The substituents not defined herein are construed as the same meanings understood by one of ordinary skill in the art.

The unsubstituted C1-C60 alkyl group used herein may be linear or branched. Examples of the alkyl group may include, but are not limited to, a methyl group, an ethyl group, a propyl group, an isobutyl group, a sec-butyl group, a pentyl group, an iso-amyl group, a hexyl group, a heptyl group, an octyl group, a nonanyl group, and a dodecyl group. At least one hydrogen atom of the alkyl group may be substituted with a deuterium atom, a halogen atom, a hydroxyl group, a nitro group, a cyano group, an amino group, an amidino group, a hydrazine, a hydrazone, a carboxyl group or a salt thereof, a sulfonic acid group or a salt thereof, a phosphoric acid group or a salt thereof, a C1-C10 alkyl group, a C1-C10 alkoxy group, a C2-C10 alkenyl group, a C2-C10 alkynyl group, a C6-C16 aryl group, an alkylsilyl group, an arylsilyl group, or a C4-C16 heteroaryl group.

The unsubstituted C2-C60 alkenyl group indicates an unsaturated alkyl groups having at least one carbon-carbon double bond in the center or at a terminal of the alkyl group. Examples of the alkenyl group are an ethenyl group, a propenyl group, a butenyl group, and the like. At least one hydrogen atom in the unsubstituted alkenyl group may be substituted with a substituent described above in conjunction with the alkyl group.

The unsubstituted C2-C60 alkynyl group indicates an alkyl group having at least one carbon-carbon triple bond in the center or at a terminal of the alkyl group. Non-limiting examples of the unsubstituted C2-C20 alkynyl group are acetylene, propylene, phenylacetylene, naphthylacetylene, isopropylacetylene, t-butylacetylene, and diphenylacetylene. At least one hydrogen atom in the alkynyl group may be substituted with a substituent described above in conjunction with the alkyl group.

The unsubstituted C3-C60 cycloalkyl group indicates a C3-C60 cyclic alkyl group wherein at least one hydrogen atom in the cycloalkyl group may be substituted with a substituent described above in conduction with the C1-C60 alkyl group.

The unsubstituted C1-C60 alkoxy group indicates a group having a structure of —OA wherein A is an unsubstituted C1-C60 alkyl group as described above. Non-limiting examples of the unsubstituted C1-C60 alkoxy group are a methoxy group, an ethoxy group, a propoxy group, an isopropyloxy group, a butoxy group, and a pentoxy group. At least one hydrogen atom of the alkoxy group may be substituted with a substituent such as those described above in conjunction with the alkyl group.

The unsubstituted C5-C60 aryl group indicates a carbocyclic aromatic system containing at least one ring. At least two rings may be fused to each other or linked to each other by a single bond. The term 'aryl' refers to an aromatic system, such as phenyl, naphthyl, or anthracenyl. At least one hydrogen atom in the aryl group may be substituted with a substituent described above in conjunction with the unsubstituted C1-C60 alkyl group.

Non-limiting examples of the substituted or unsubstituted C5-C60 aryl group are a phenyl group, a C1-C10 alkylphenyl group (for example, an ethylphenyl group), a biphenyl group, a C1-C10 alkyl biphenyl group, a C1-C10 alkoxybiphenyl group, a o-, m-, and p-toryl group, an o-, m-, and p-cumenyl group, a mesityl group, a phenoxyphenyl group, a (α,α-dimethylbenzene)phenyl group, a (N,N'-dimethyl)aminophenyl group, a (N,N'-diphenyl)aminophenyl group, a pentalenyl group, an indenyl group, a naphthyl group, a C1-C10 alkylnaphthyl group (for example, a methylnaphthyl group), a C1-C10 alkoxynaphthyl group (for example, a methoxynaphthyl group), an anthracenyl group, an azulenyl group, a heptalenyl group, an acenaphthylenyl group, a phenalenyl group, a fluorenyl group, an anthraquinolyl group, a methylanthryl group, a phenanthryl group, a triphenylene group, a pyrenyl group, a chrycenyl group, an ethyl-chrysenyl group, a picenyl group, a perylenyl group, a pentaphenyl group, a pentacenyl group, a tetraphenylenyl group, a hexaphenyl group, a hexacenyl group, a rubicenyl group, a coronelyl group, a trinaphthylenyl group, a heptaphenyl group, a heptacenyl group, a pyranthrenyl group, and an ovalenyl group.

The unsubstituted C3-C60 heteroaryl group used herein includes one, two or three hetero atoms selected from N, O, P and S. At least two rings may be fused to each other or linked to each other by a single bond. Non-limiting examples of the unsubstituted C4-C60 heteroaryl group are a pyrazolyl group, an imidazolyl group, an oxazolyl group, a thiazolyl group, a triazolyl group, a tetrazolyl group, an oxadiazolyl group, a pyridinyl group, a pyridazinyl group, a pyrimidinyl group, a triazinyl group, a carbazol group, an indol group, a quinolyl group, an isoquinolyl group, and a dibenzothiophene group. In addition, at least one hydrogen atom in the heteroaryl group may be substituted with a substituent described above in conjunction with the unsubstituted C1-C60 alkyl group.

The unsubstituted C5-C60 aryloxy group is a group represented by —$OA_1$, wherein $A_1$ may be a C5-C60 aryl group. An example of the aryloxy group is a phenoxy group. At least one hydrogen atom in the aryloxy group may be substituted with a substituent described above in conjunction with the unsubstituted C1-C60 alkyl group.

The unsubstituted C5-C60 arylthio group is a group represented by —$SA_1$, wherein $A_1$ may be a C5-C60 aryl group. Non-limiting examples of the arylthio group are a benzenethio group and a naphthylthio group. At least one hydrogen atom in the arylthio group may be substituted with a substituent described above in conjunction with the unsubstituted C1-C60 alkyl group.

The unsubstituted C6-C60 condensed polycyclic group used herein refers to a substituent including at least two rings wherein at least one aromatic ring and/or at least one non-aromatic ring are fused to each other, or refers to a substitutent having an unsaturated group in a ring that may not form a conjugate structure. The unsubstituted C6-C60 condensed polycyclic group are distinct from an aryl group or a heteroaryl group in terms of being non-aromatic.

Non-limiting examples of the compound represented by Formula 1 are Compounds 1 to 56 represented by the following formulae.

1

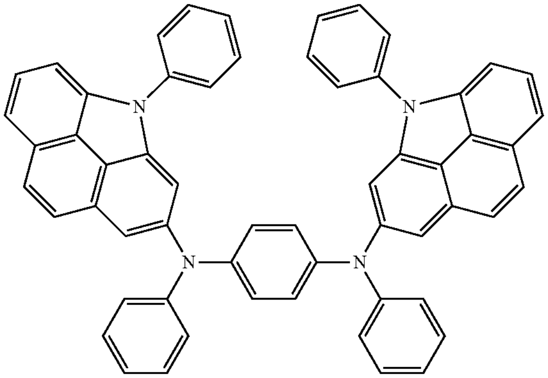

2

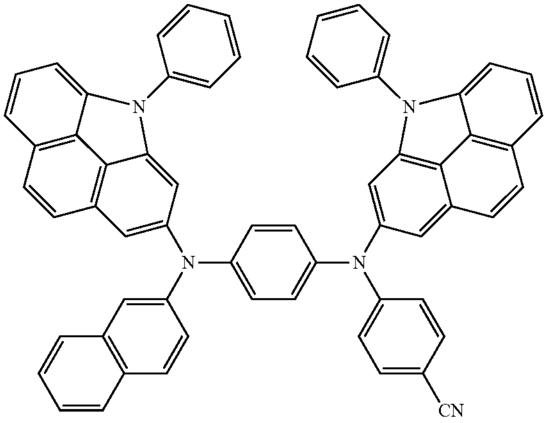

3

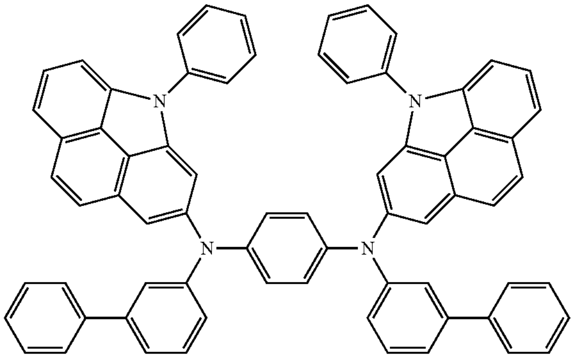

4

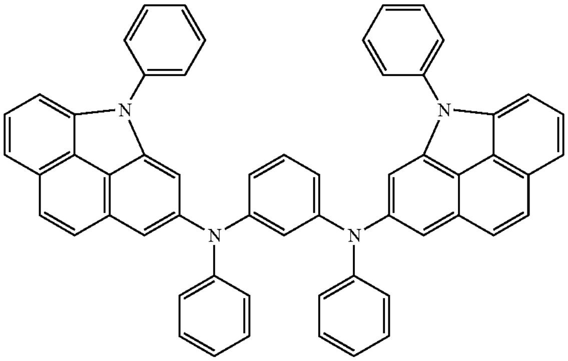

-continued
5
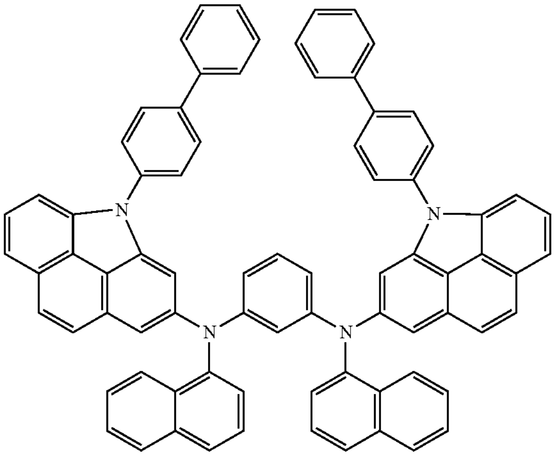
6
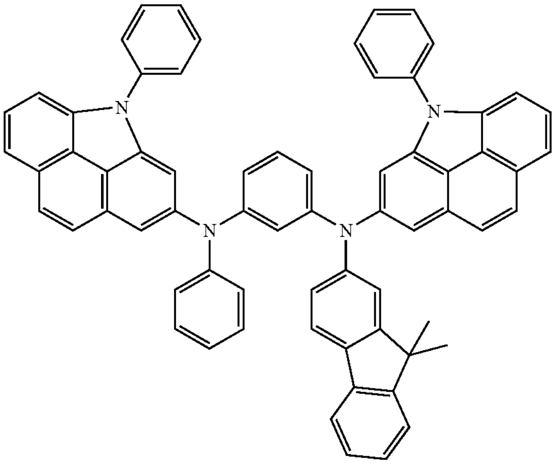
7
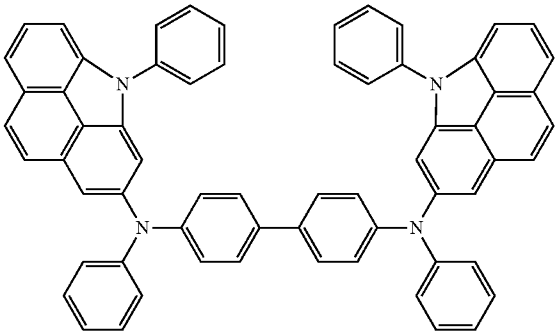
8
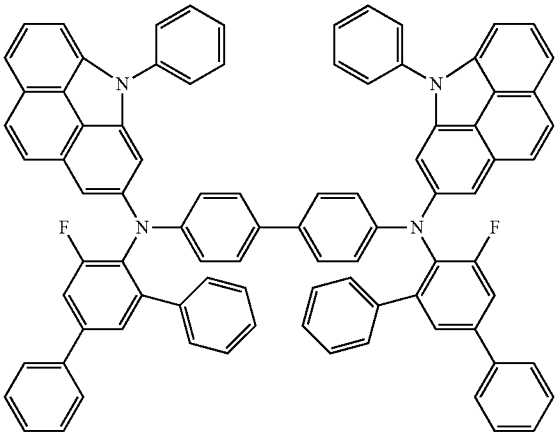
9
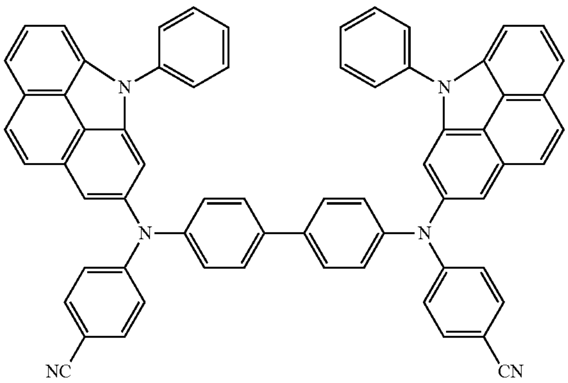
10
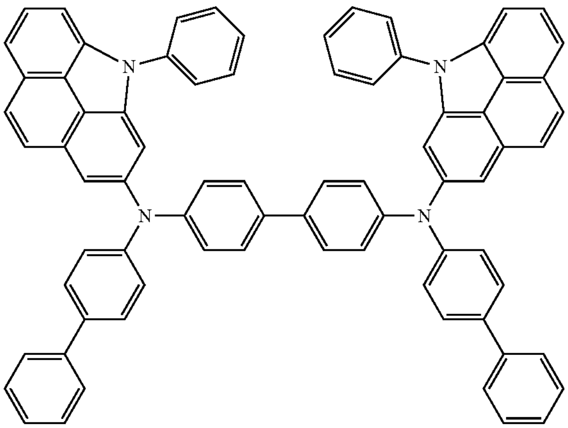

-continued
11
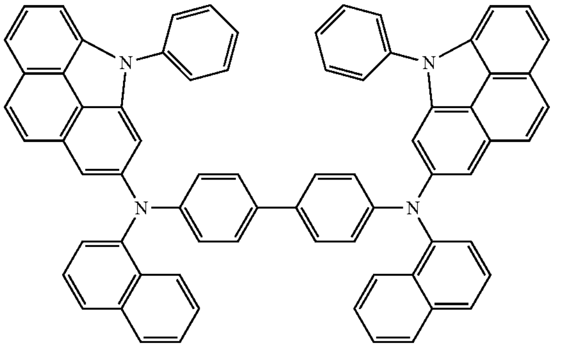
12
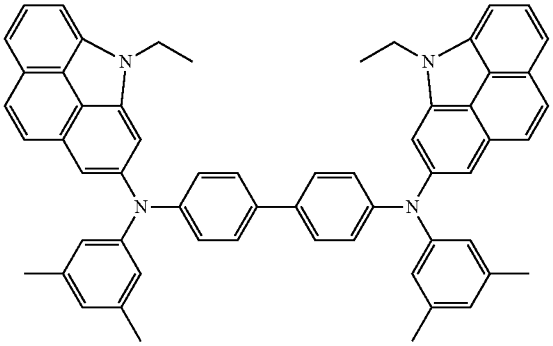
13
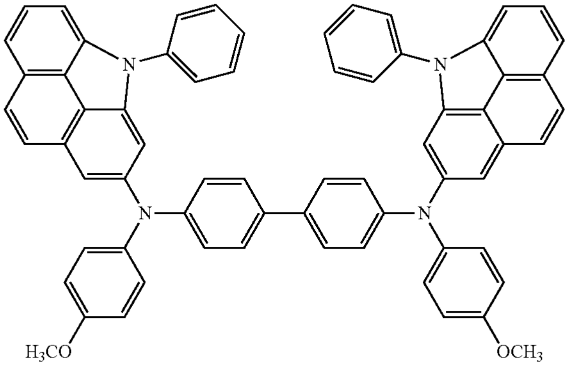
14
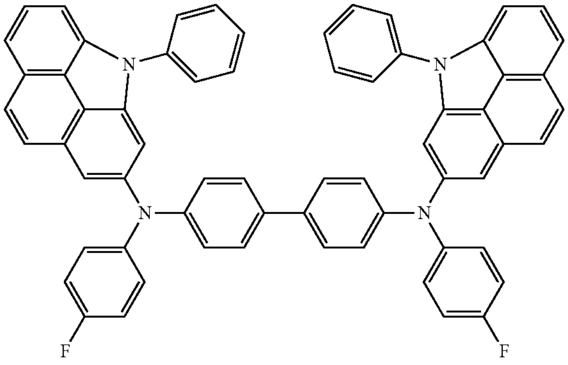
15
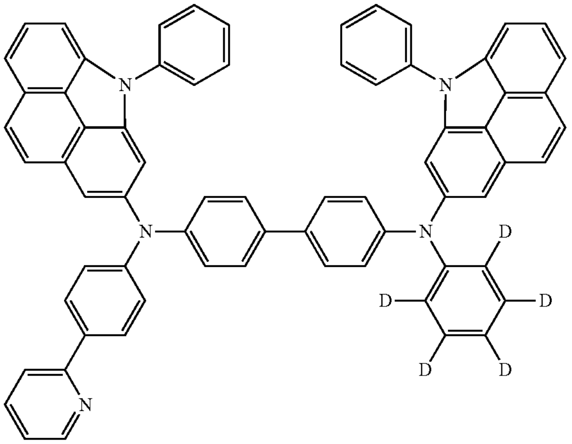
16
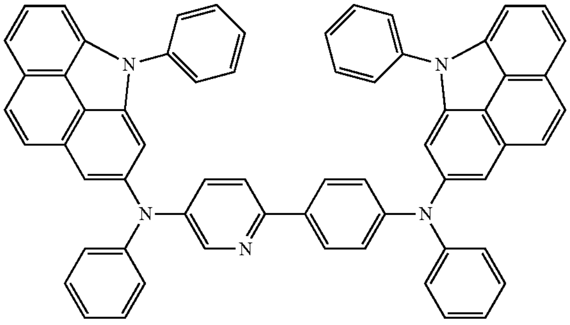

-continued
17
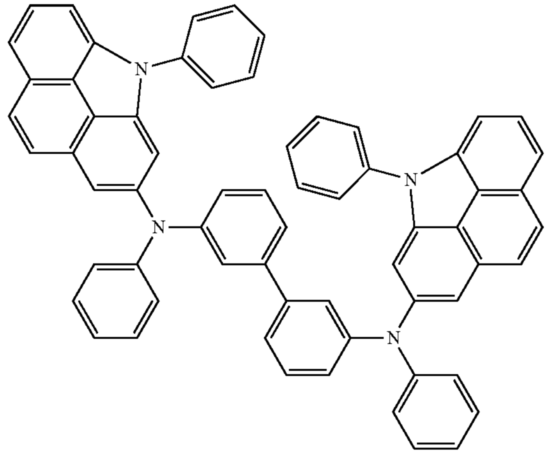
18
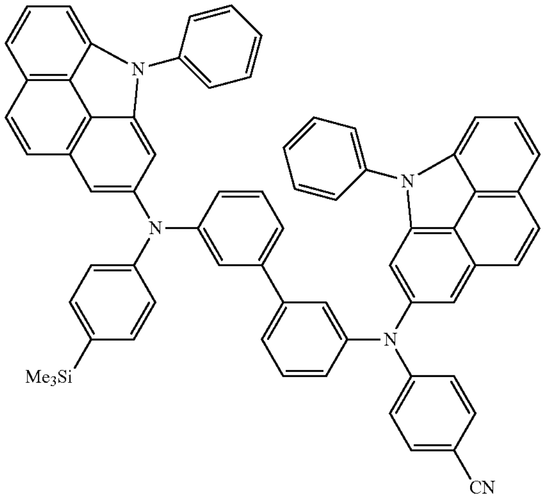
19
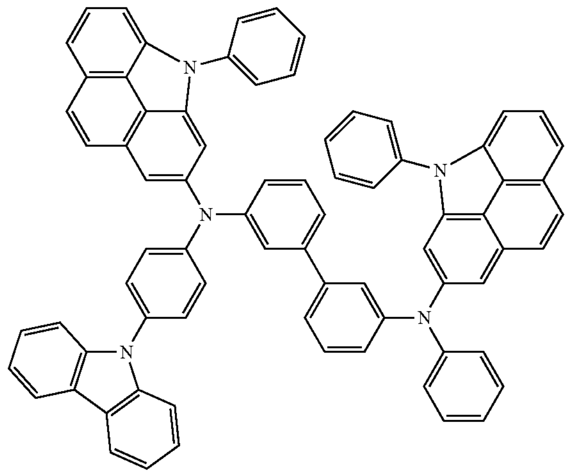
20
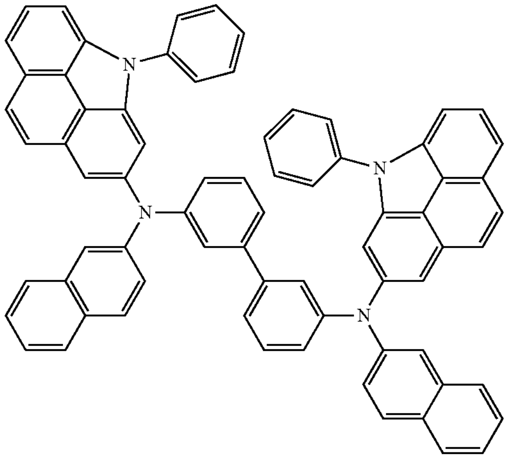
21
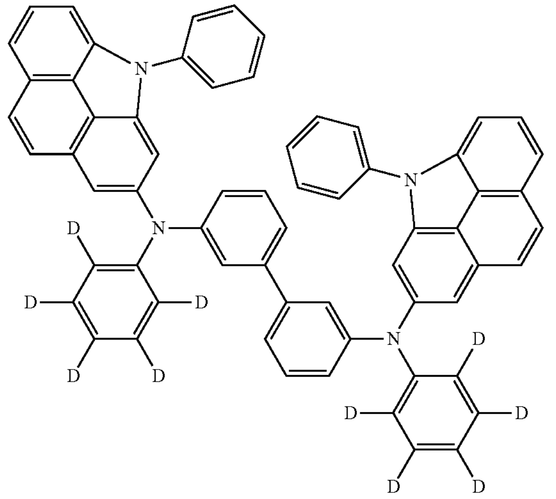
22
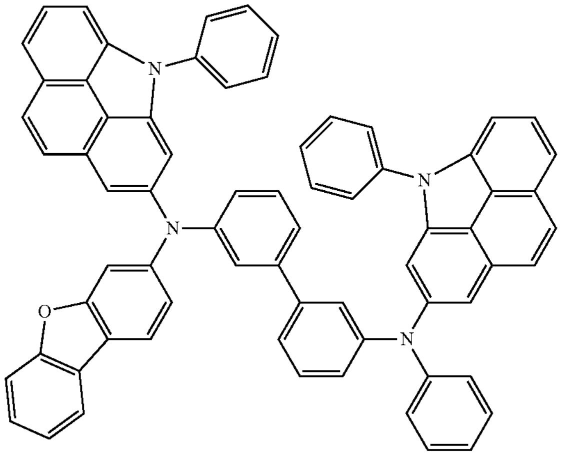

-continued
23
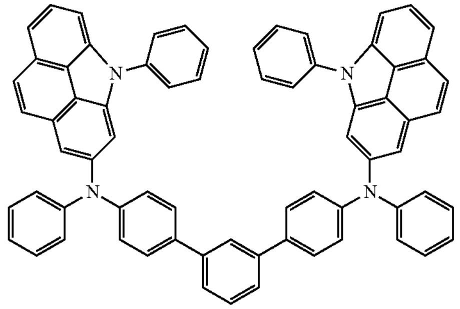
24
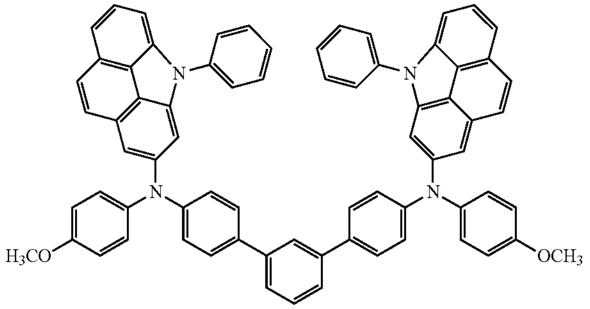
25
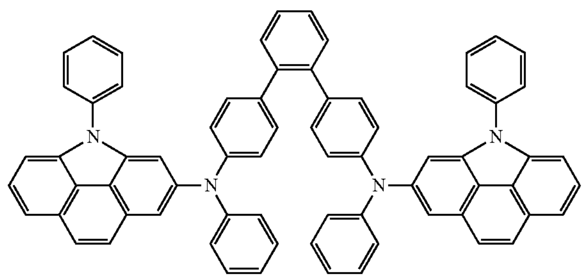
26
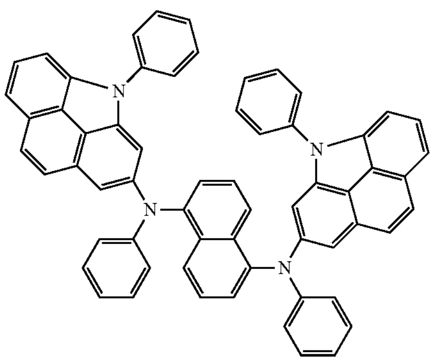
27
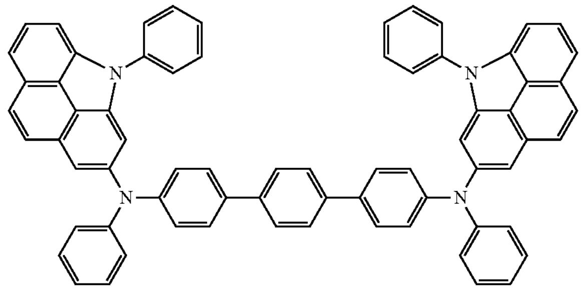
28
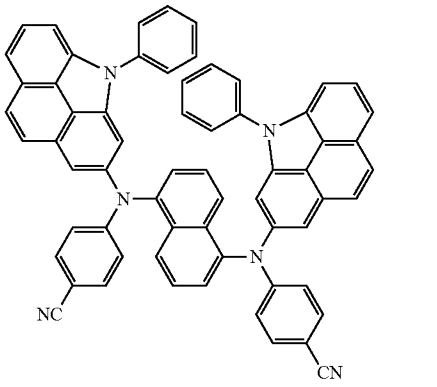
29
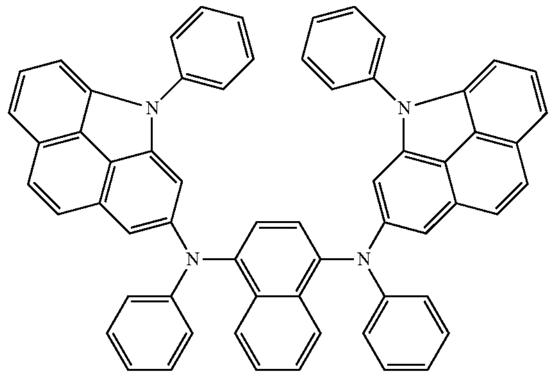
30
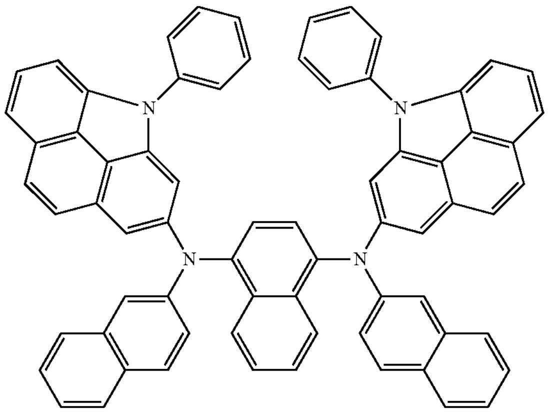

-continued
31
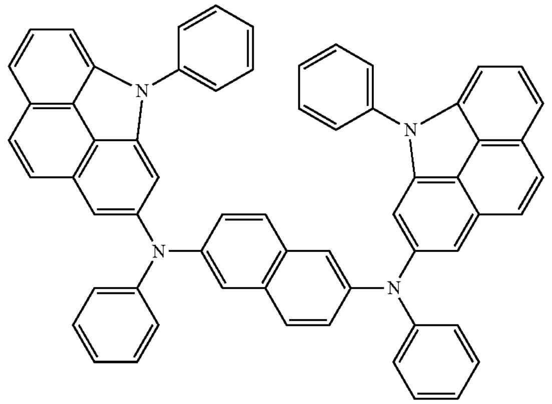
32
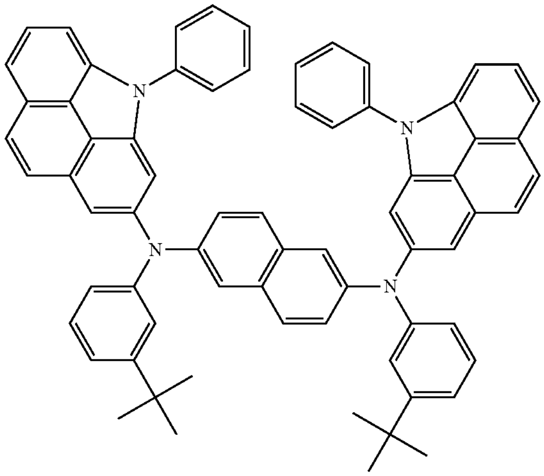
33
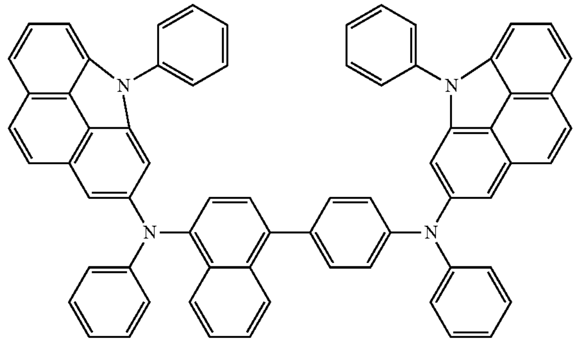
34
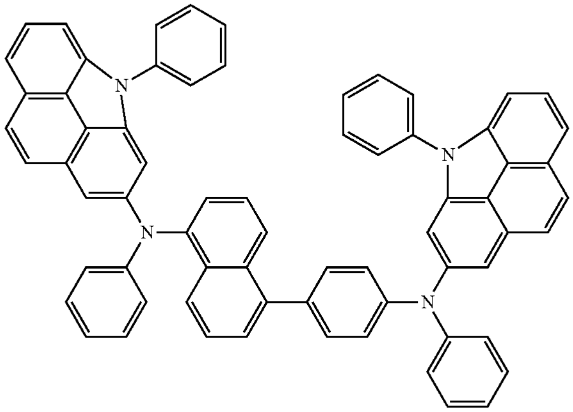
35
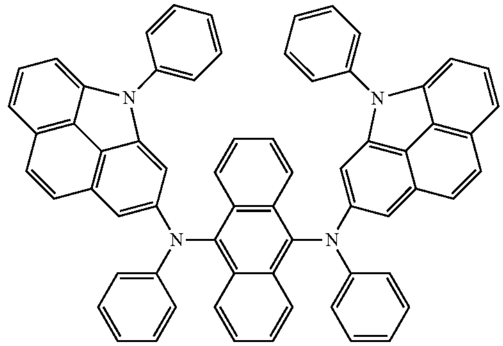
36
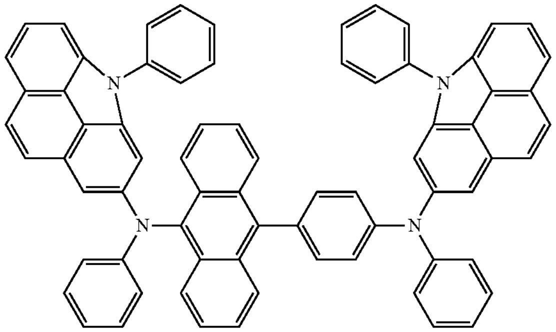
37
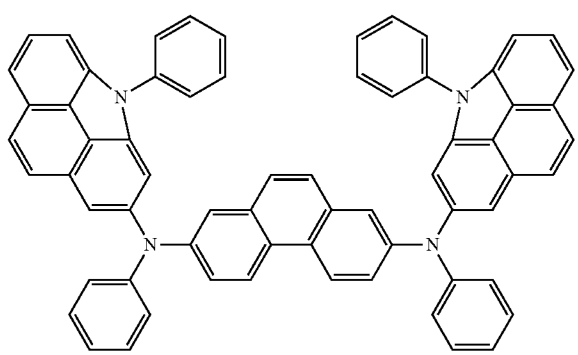
38
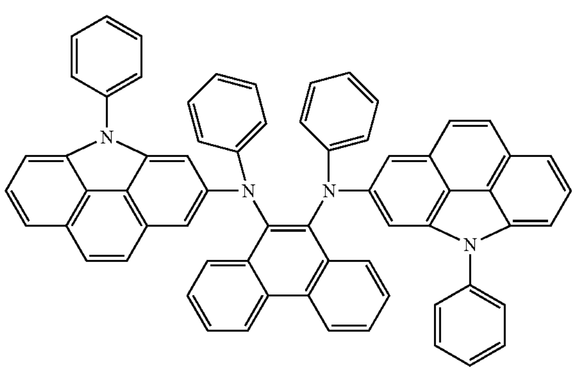

-continued
39
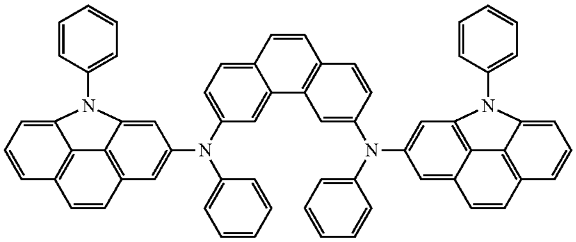
40
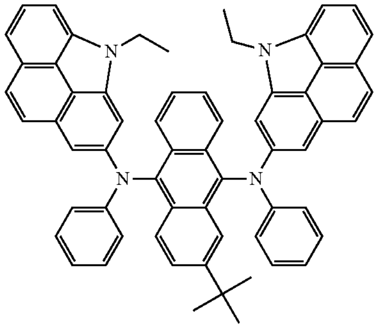
41
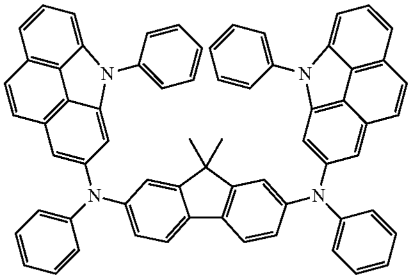
42
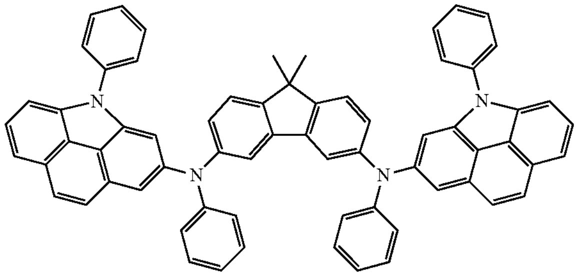
43
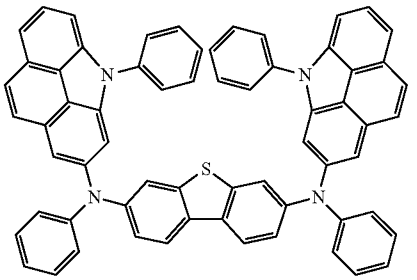
44
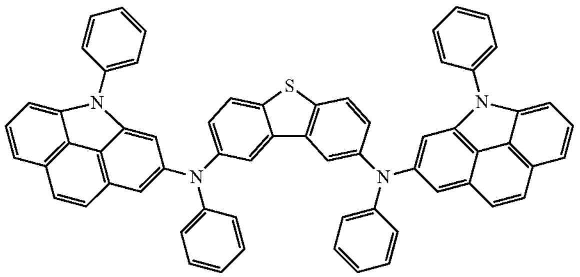
45
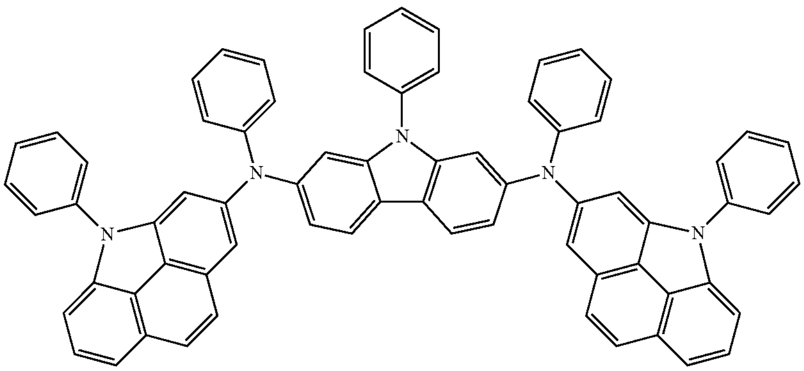

-continued
46
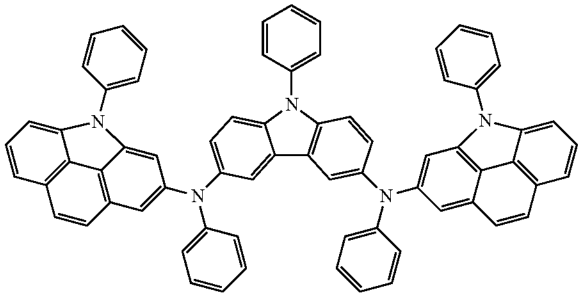
47
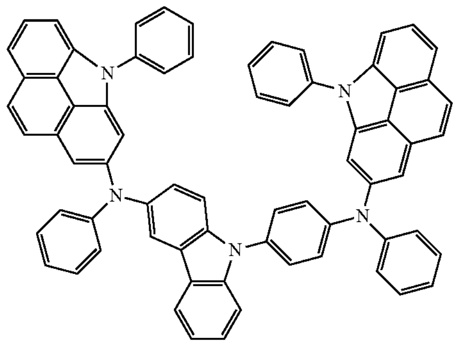
48
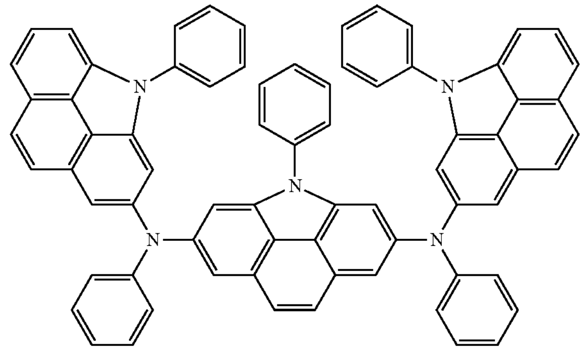
49
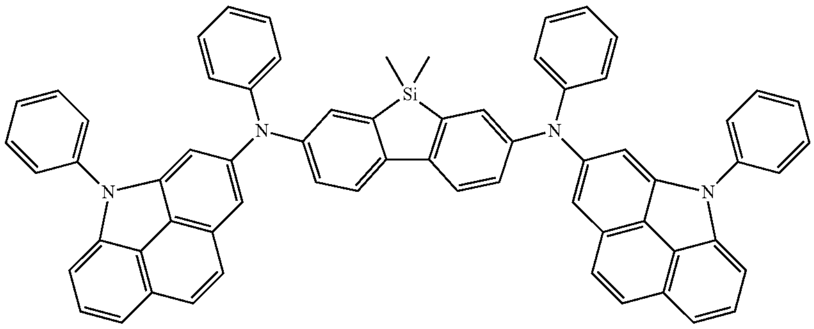
50
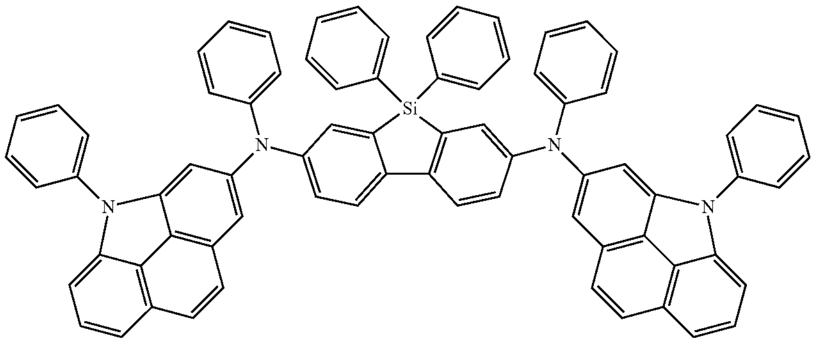

-continued
51
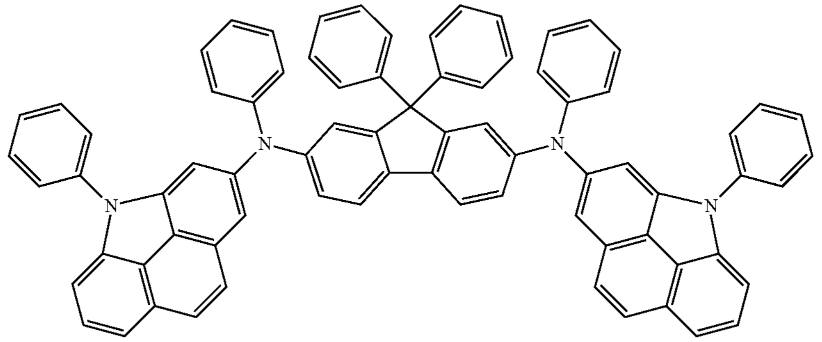
52
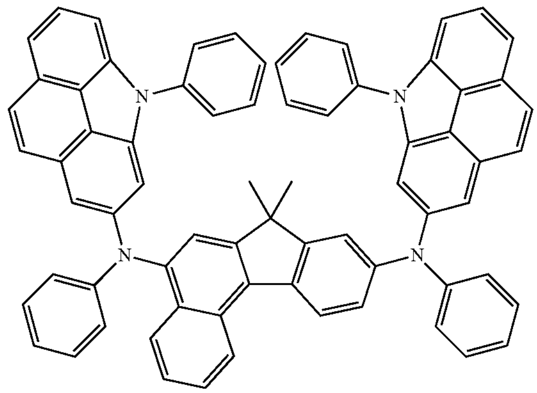
53
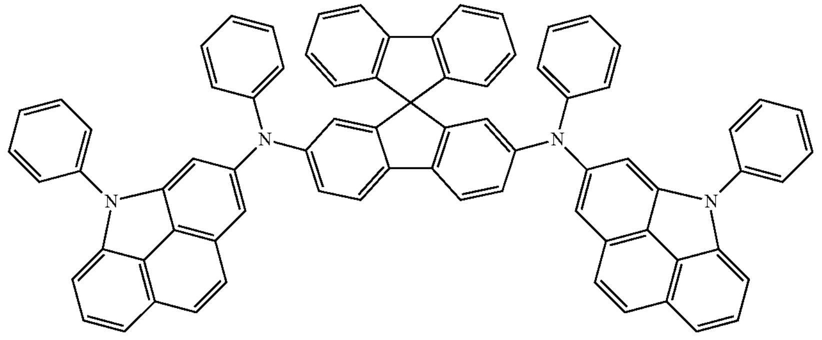
54
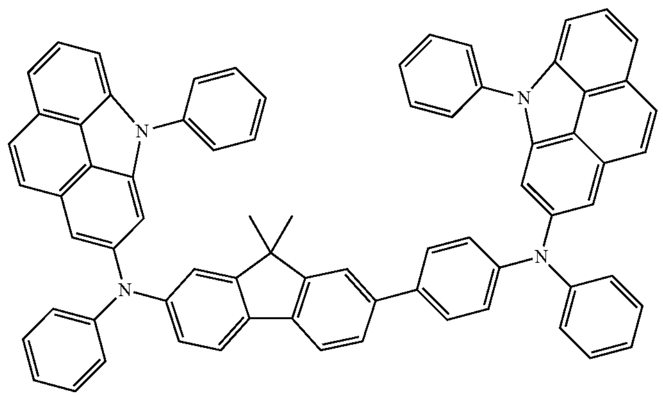

-continued

55

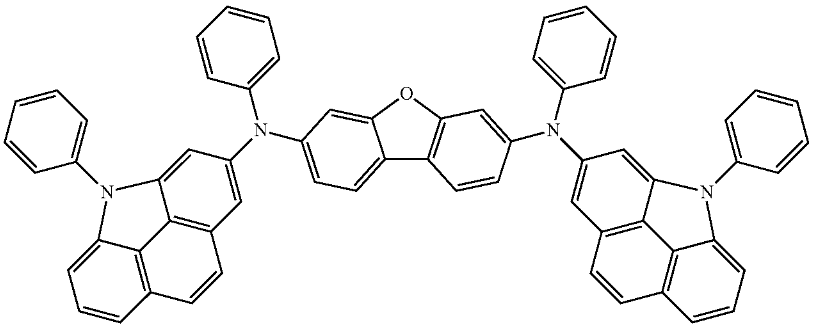

56

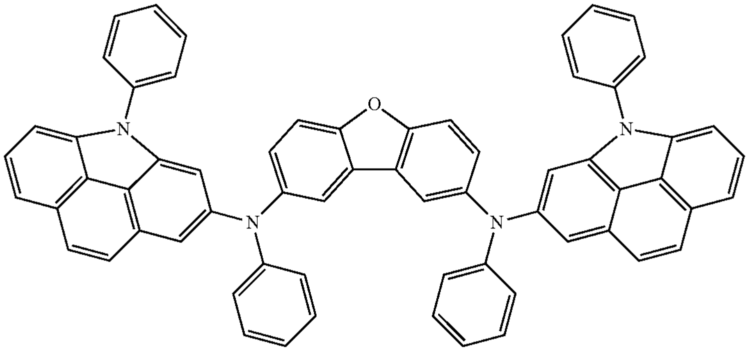

According to another embodiment of the present, an organic light-emitting device includes a first electrode, a second electrode, and an organic film disposed between the first electrode and the second electrode, wherein the organic film includes the compound of Formula 1 described above.

The organic layer may include at least one layer selected from among a hole injection layer, a hole transport layer, a functional layer having both hole injection and hole transport capabilities (hereinafter, "H-functional layer"), a buffer layer, an electron blocking layer, an emission layer, a hole blocking layer, an electron transport layer, an electron injection layer, and a functional layer having both electron injection and electron transport capabilities (hereinafter, "E-functional layer").

For example, the organic layer may serve as a hole injection layer, a hole transport layer, a functional layer having both hole injection and hole transport capabilities, or an emission layer.

In some embodiments, the organic light-emitting device may include an electron injection layer, an electron transport layer, an emission layer, a hole injection layer, a hole transport layer, or a functional layer having both hole injection and transport capabilities, wherein the hole injection layer, the hole transport layer, or the functional layer having both hole injection and transport capabilities may include the compound of Formula 1 above. The emission layer may include the compound of Formula 1 above. The emission layer may further include an anthracene-based compound, an arylamine-based compound, or a styryl-based compound, in addition to the compound of Formula 1 above.

In some other embodiments, the organic light-emitting device may include an electron injection layer, an electron transport layer, an emission layer, a hole injection layer, a hole transport layer, or a functional layer having both hole injection and transport capabilities. At least one of a red emission layer, a green emission layer, a blue emission layer, and a white emission layer of the emission layer may include a phosphorescent compound. The emission layer may include the compound of Formula 1 above. The hole injection layer, the hole transport layer, or the functional layer having both hole injection and hole transport capabilities may further include a charge-generating material, in addition to the compound of Formula 1 above. In some embodiments, the charge-generating material may be a p-type dopant, and the p-type dopant may be a quinine derivative, a metal oxide or a cyano group-containing compound.

In some embodiments, the organic film may include an electron transport layer, and the electron transport layer may include an electron-transporting organic compound and a meta complex. The metal complex may be a lithium (Li) complex.

The term "organic layer" as used herein refers to a single layer and/or a plurality of layers disposed between the first and second electrodes of the organic light-emitting device.

FIG. 1 is a schematic sectional view of an organic light-emitting device according to an embodiment of the present invention. Hereinafter, a structure of an organic light-emitting device according to an embodiment of the present invention and a method of manufacturing the same will now be described with reference to FIG. 1.

A substrate (not shown) may be any substrate that is used in existing organic light emitting devices. In some embodiments the substrate 11 may be a glass substrate or a transparent plastic substrate with strong mechanical strength, thermal stability, transparency, surface smoothness, ease of handling, and water resistance.

The first electrode may be formed by depositing or sputtering a first electrode-forming material on the substrate. When the first electrode is an anode, a material having a high work function may be used as the first electrode-forming material to facilitate hole injection. The first electrode may be a reflective electrode or a transmission electrode. Transparent and conductive materials such as ITO, IZO, $SnO_2$, and ZnO may be used to form the first electrode. The first electrode may be formed as a reflective electrode using magnesium (Mg), aluminum (Al), aluminum-lithium (Al—Li), calcium (Ca), magnesium-indium (Mg—In), magnesium-silver (Mg—Ag), or the like.

The first electrode 13 may have a single-layer structure or a multi-layer structure including at least two layers. For example, the first electrode may have a three-layered structure of ITO/Ag/ITO, but is not limited thereto.

An organic layer(s) is disposed on the first electrode.

The organic layer may include a hole injection layer (HIL), a hole transport layer (HTL), a buffer layer (not shown), an emission layer (EML), an electron transport layer (ETL), or an electron injection layer (EIL).

The HIL may be formed on the first electrode by vacuum deposition, spin coating, casting, Langmuir-Blodgett (LB) deposition, or the like.

When the HIL is formed using vacuum deposition, vacuum deposition conditions may vary according to the compound that is used to form the HIL, and the desired structure and thermal properties of the HIL to be formed. For example, vacuum deposition may be performed at a temperature of about 100° C. to about 500° C., a pressure of about $10^{-8}$ torr to about $10^{-3}$ torr, and a deposition rate of about 0.01 to about 100 Å/sec. However, the deposition conditions are not limited thereto.

When the HIL is formed using spin coating, the coating conditions may vary according to the compound that is used to form the HIL, and the desired structure and thermal properties of the HIL to be formed. For example, the coating rate may be in the range of about 2000 rpm to about 5000 rpm, and a temperature at which heat treatment is performed to remove a solvent after coating may be in the range of about 80° C. to about 200° C. However, the coating conditions are not limited thereto.

A hole injecting material for The HIL may be the compound of Formula 1 above or any known hole injecting material. Non-limiting examples of the known hole injecting material that may be used to form the HIL are N,N'-diphenyl-N,N'-bis-[4-(phenyl-m-tolyl-amino)-phenyl]-biphenyl-4,4'-diamine, (DNTPD), a phthalocyanine compound such as copperphthalocyanine, 4,4',4"-tris(3-methylphenylphenylamino)triphenylamine (m-MTDATA), N,N'-di(1-naphthyl)-N,N'-diphenylbenzidine (NPB), TDATA, 2T-NATA, polyaniline/dodecylbenzenesulfonic acid (Pani/DBSA), poly(3,4-ethylenedioxythiophene)/poly(4-styrenesulfonate) (PEDOT/PSS), polyaniline/camphor sulfonicacid (Pani/CSA), and polyaniline)/poly(4-styrenesulfonate (PANI/PSS).

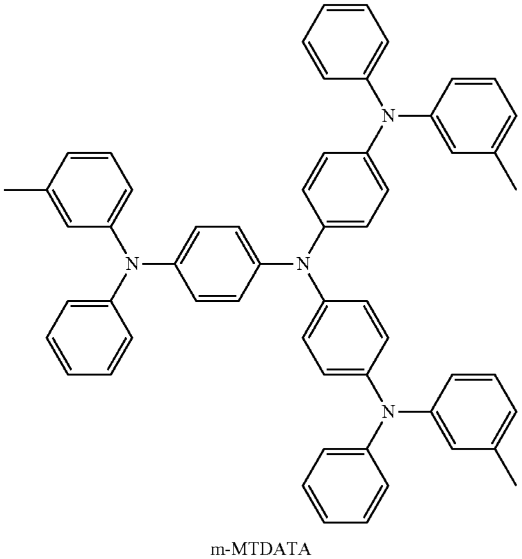

m-MTDATA

-continued

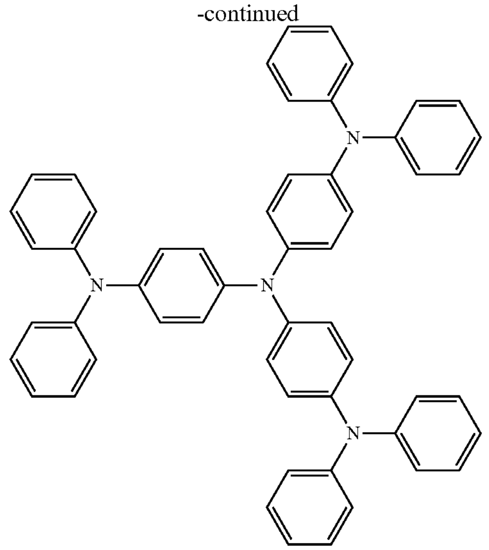

TDATA

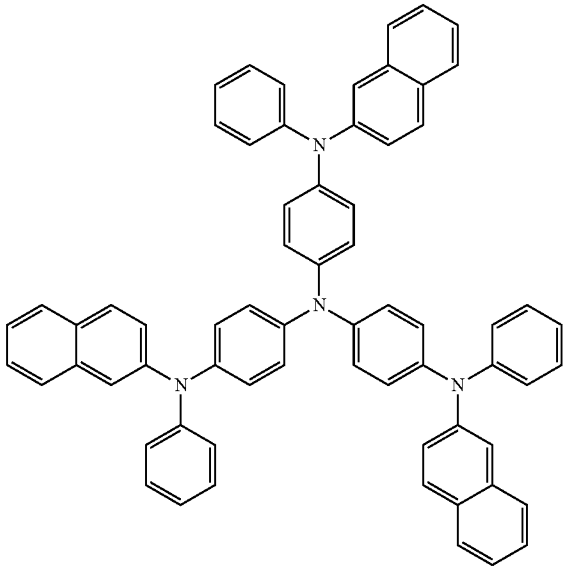

2-TNATA

The thickness of the HIL may be from about 100 Å to about 10000 Å, and in some embodiments, from about 100 Å to about 1000 Å. When the thickness of the HIL is within these ranges, the HIL may have good hole injecting ability without a substantial increase in driving voltage.

Then, a HTL may be formed on the HIL by using vacuum deposition, spin coating, casting, Langmuir-Blodgett (LB) deposition, or the like. When the HTL is formed using vacuum deposition or spin coating, the conditions for deposition and coating may be similar to those for the formation of the HIL, though the conditions for the deposition and coating may vary according to the material that is used to form the HTL.

A hole transporting material for the HTL may the compound of Formula 1 above or any known hole transporting material. Non-limiting examples of the known hole transporting material are carbazole derivatives, such as N-phenylcarbazole or polyvinylcarbazole, N,N'-bis(3-methylphenyl)-N,N'-diphenyl-[1,1-biphenyl]-4,4'-diamine (TPD), 4,4',4"-tris(N-carbazolyl)triphenylamine (TCTA), and N,N'-di(1-naphthyl)-N,N'-diphenylbenzidine) (NPB).

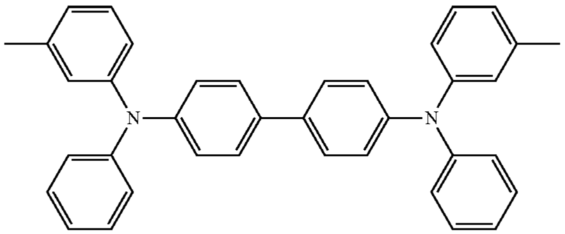

TPD

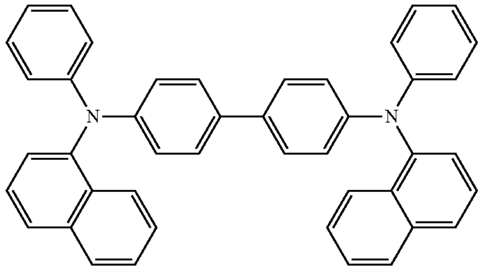

NPB

The thickness of the HTL may be from about 50 Å to about 2000 Å, and in some embodiments, from about 100 Å to about 1500 Å. When the thickness of the HTL is within these ranges, the HTL may have good hole transporting ability without a substantial increase in driving voltage.

The H-functional layer (having both hole injection and hole transport capabilities) may contain at least one material from each group of the hole injection layer materials and hole transport layer materials. The thickness of the H-functional layer may be from about 500 Å to about 10,000 Å, and in some embodiments, may be from about 100 Å to about 1,000 Å. When the thickness of the H-functional layer is within these ranges, the H-functional layer may have good hole injection and transport capabilities without a substantial increase in driving voltage.

In some embodiments, at least one of the HIL, HTL, and H-functional layer may include at least one of a compound of Formula 300 below and a compound of Formula 350 below:

<Formula 300>

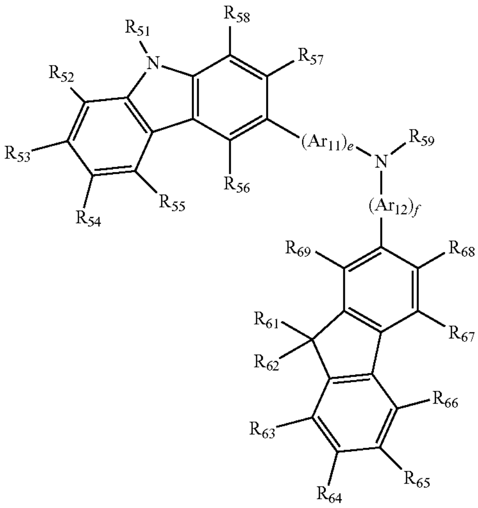

-continued

<Formula 350>

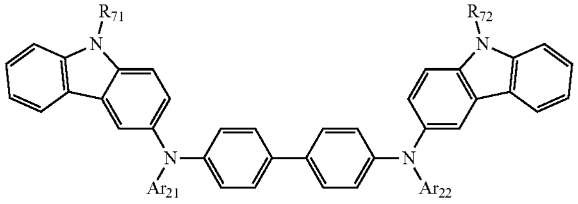

In Formulae 300 and 350, $Ar_{11}$, $Ar_{12}$, $Ar_2$, and $Ar_{22}$ may be each independently a substituted or unsubstituted $C_5$-$C_{60}$ arylene group.

In Formula 300, e and f may be each independently an integer from 0 to 5, for example, may be 0, 1, or 2. For example, e may be 1, and f may be 0, but not limited thereto.

In Formulae 300 and 350 above, $R_{51}$ to $R_{58}$, $R_{61}$ to $R_{69}$, and $R_{71}$ to $R_{72}$ may be each independently a hydrogen atom, a deuterium atom, a halogen atom, a hydroxyl group, a cyano group, a nitro group, an amino group, an amidino group, a hydrazine group, a hydrazone, a carboxyl group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$alkynyl group, a substituted or unsubstituted $C_1$-$C_{60}$ alkoxy group, a substituted or unsubstituted $C_3$-$C_{60}$ cycloalkyl group, a substituted or unsubstituted $C_5$-$C_{60}$ aryl group, a substituted or unsubstituted $C_5$-$C_{60}$ aryloxy group, or a substituted or unsubstituted $C_5$-$C_{60}$ arylthio group. In some embodiments, $R_{51}$ to $R_{58}$, $R_{61}$ to $R_{69}$, $R_{71}$, and $R_{72}$ may be each independently one of a hydrogen atom; a deuterium atom; a halogen atom; a hydroxyl group; a cyano group; a nitro group; an amino group; an amidino group; a hydrazine; a hydrazone; a carboxyl group or a salt thereof; a sulfonic acid group or a salt thereof; a phosphoric acid group or a salt thereof; a $C_1$-$C_{10}$ alkyl group (for example, a methyl group, an ethyl group, a propyl group, a butyl group, a pentyl group, a hexyl group, or the like); a $C_1$-$C_{10}$ alkoxy group (for example, a methoxy group, an ethoxy group, a propoxy group, a butoxy group, a pentoxy group, or the like); a $C_1$-$C_{10}$ alkyl group and a $C_1$-$C_{10}$ alkoxy group that are substituted with at least one of a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, and a phosphoric acid group or a salt thereof; a phenyl group; a naphthyl group; an anthryl group; a fluorenyl group; a pyrenyl group; and a phenyl group, a naphthyl group, an anthryl group, a fluorenyl group, and a pyrenyl group that are substituted with at least one of a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a $C_1$-$C_{10}$ alkyl group, and a $C_1$-$C_{10}$ alkoxy group.

In Formula 300, $R_{59}$ may be one of a phenyl group, a naphthyl group, an anthryl group, a biphenyl group, a pyridyl group; and a phenyl group, a naphthyl group, an anthryl group, a biphenyl group, and a pyridyl group that are substituted with at least one of a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a substituted or unsubstituted $C_1$-$C_{20}$ alkyl group, and a substituted or unsubstituted $C_1$-$C_{20}$ alkoxy group.

In an embodiment the compound of Formula 300 may be a compound represented by Formula 300A below:

<Formula 300A>

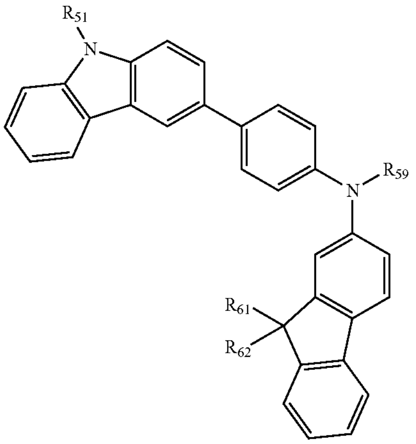

In Formula 300A, $R_{51}$, $R_{60}$, $R_{61}$, and $R_{59}$ may be as defined above.

In some non-limiting embodiments, at least one of the HIL, HTL, and H-functional layer may include at least one of compounds represented by Formulae 301 to 320 below:

301

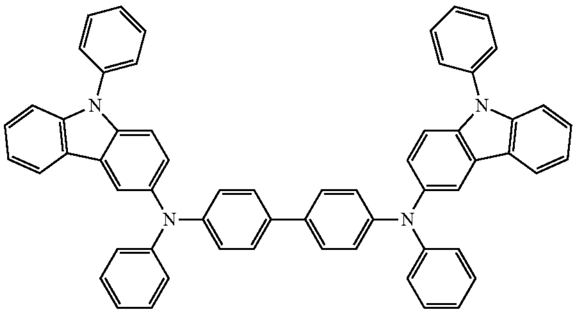

302

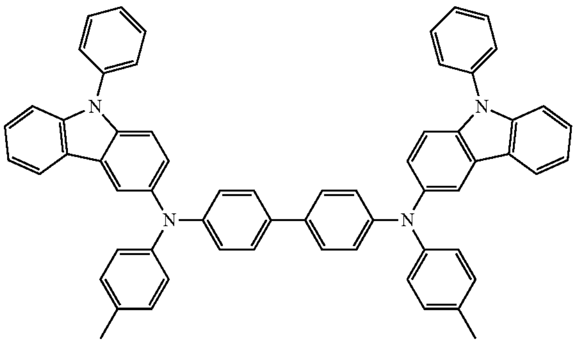

-continued

303

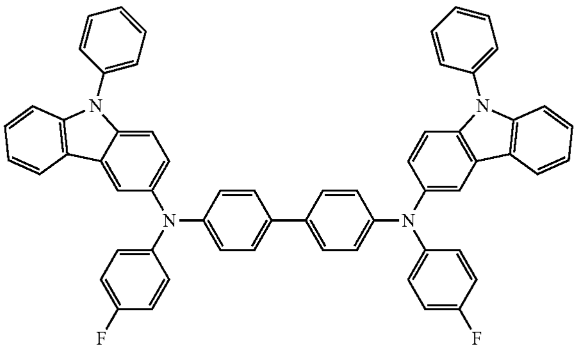

304

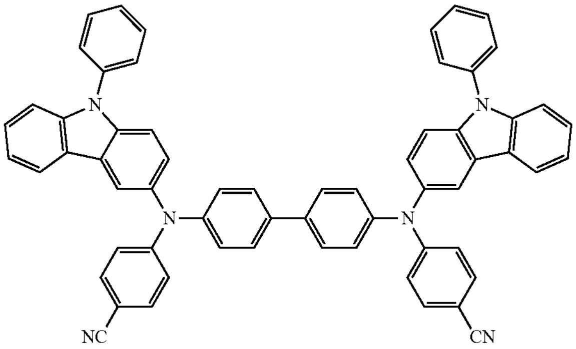

305

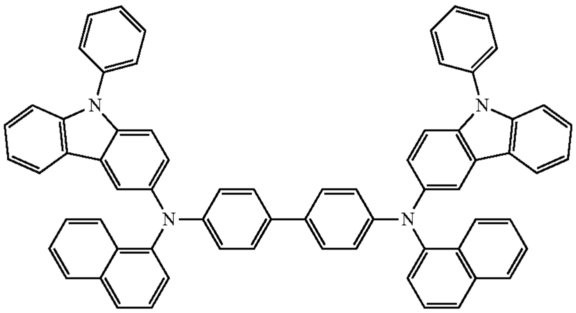

306

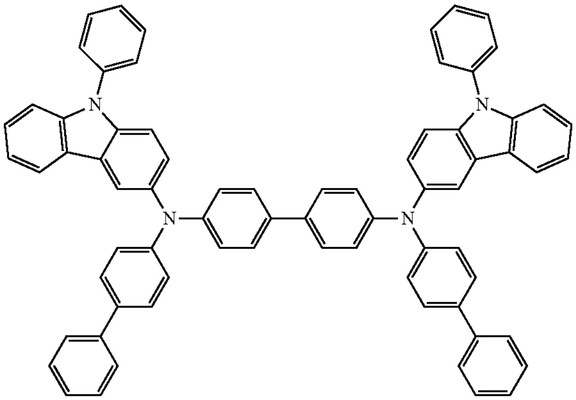

-continued
307
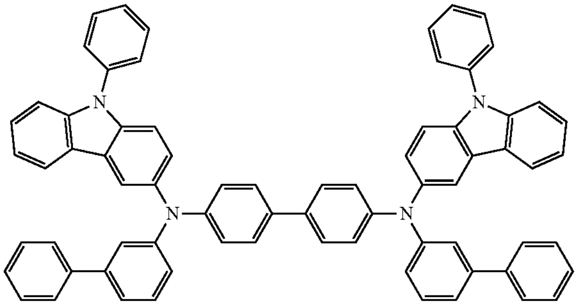
308
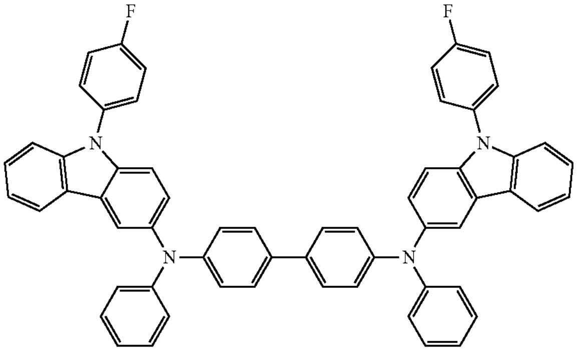
309
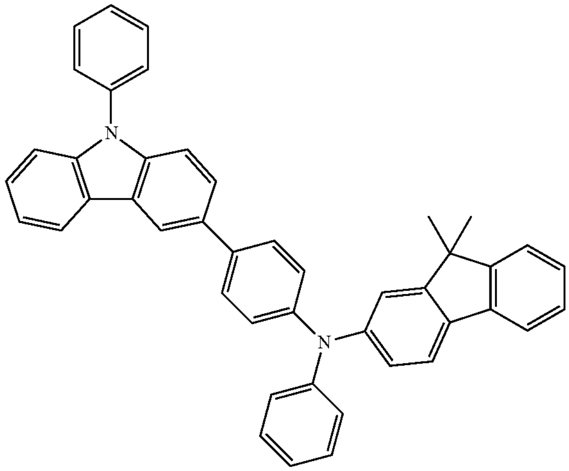
-continued
310
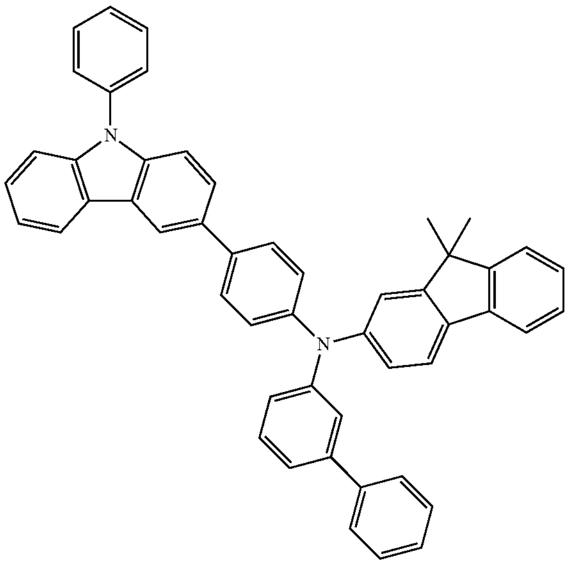
311
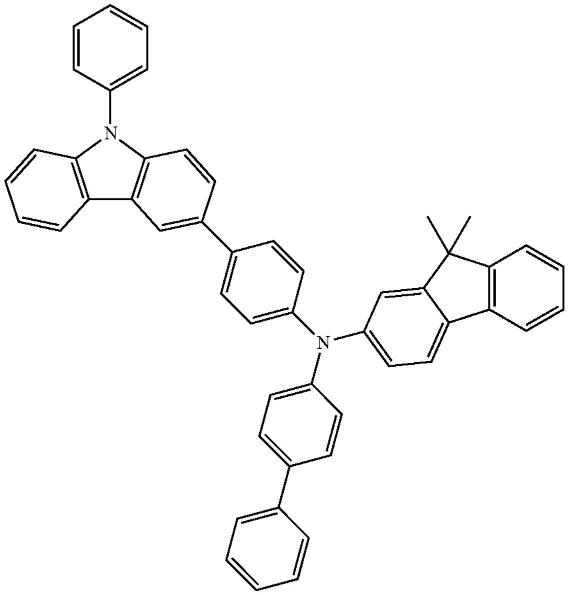

-continued
312
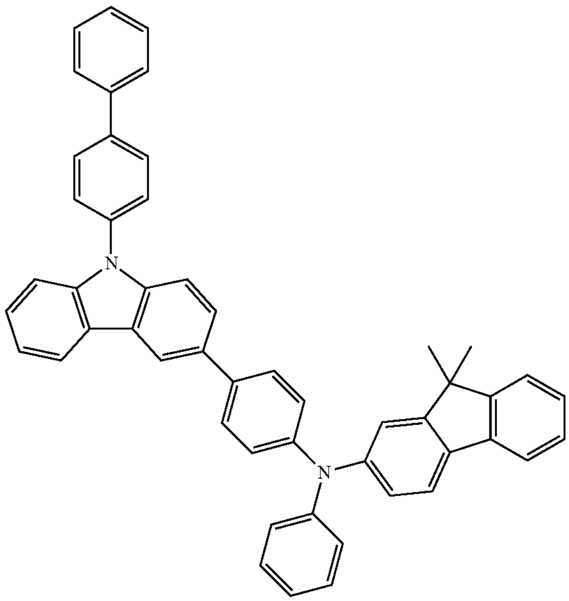
313
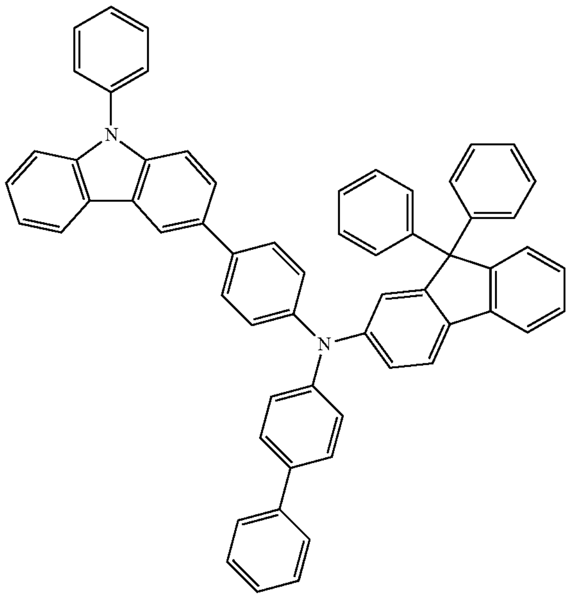
-continued
314
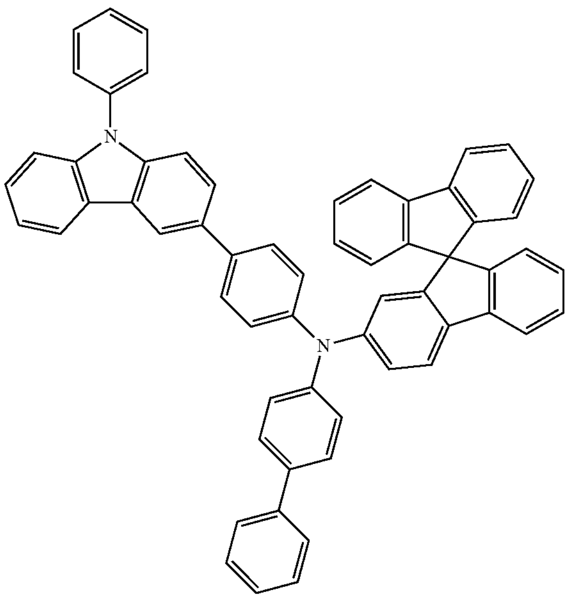
315
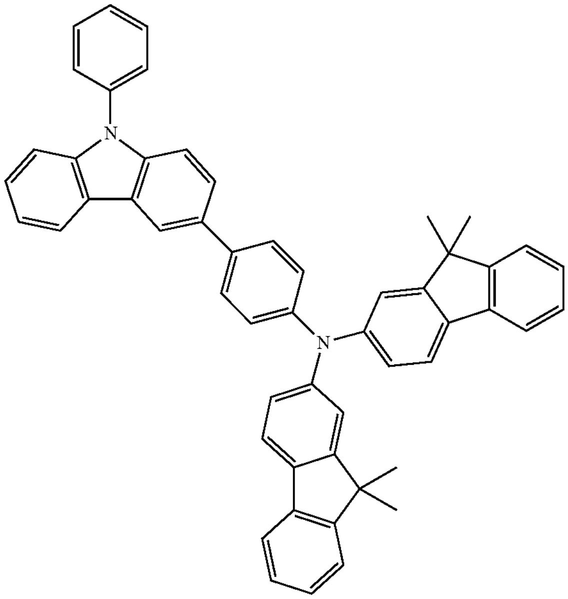

-continued

316

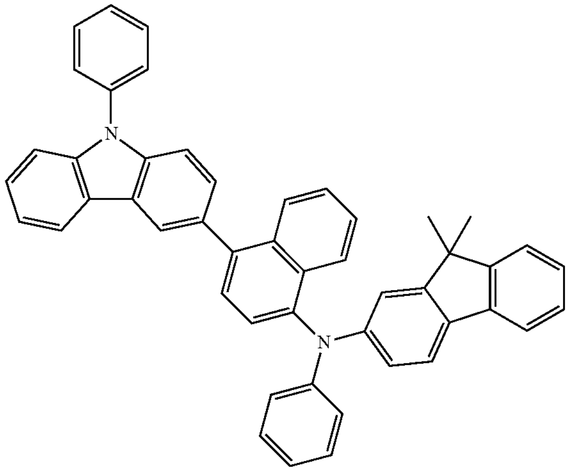

317

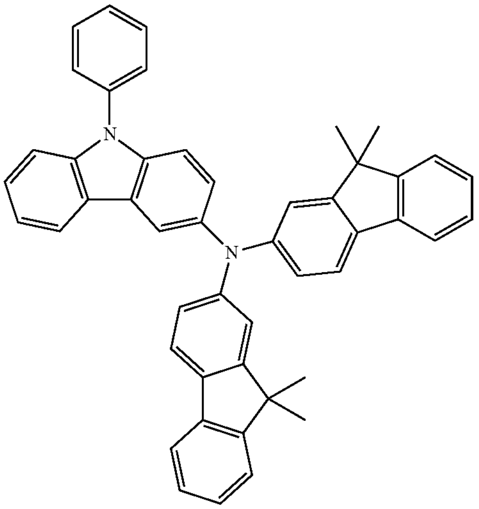

318

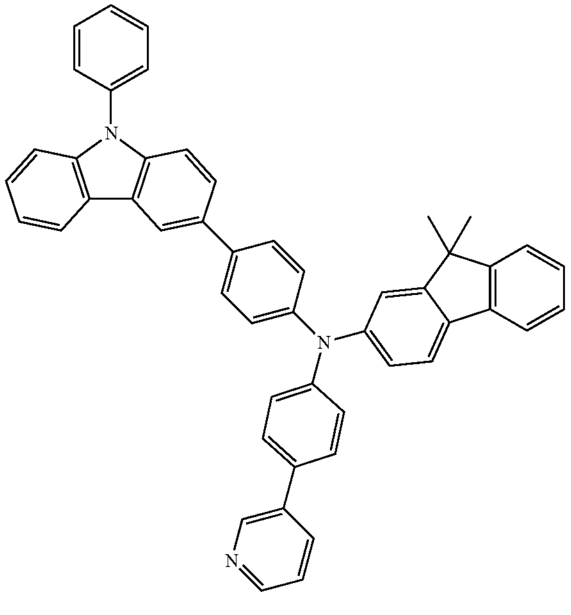

-continued

319

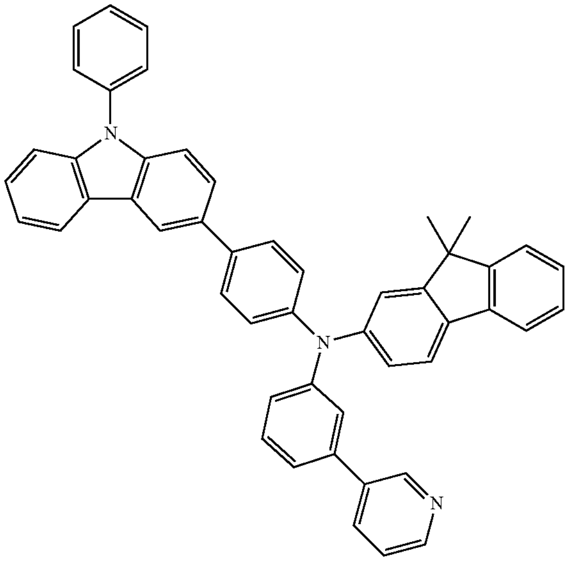

320

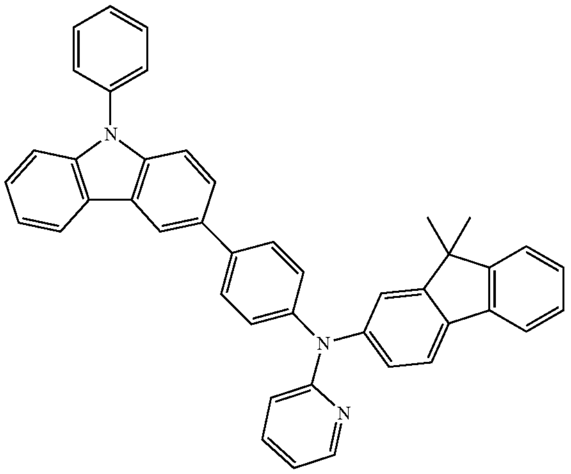

At least one of the HIL, HTL, and H-functional layer may further include a charge-generating material for improved layer conductivity, in addition to a known hole injecting material, hole transport material, and/or material having both hole injection and hole transport capabilities as described above.

The charge-generating material may be, for example, a p-dopant. The p-dopant may be one of quinine derivatives, metal oxides, and compounds with a cyano group, but are not limited thereto. Non-limiting examples of the p-dopant are quinone derivatives such as tetracyanoquinonedimethane (TCNQ), 2,3,5,6-tetrafluoro-tetracyano-1,4-benzoquinonedimethane (F4-TCNQ), and the like; metal oxides such as tungsten oxide, molybdenum oxide, and the like; and cyano-containing compounds such as Compound 200 below.

<Compound 200>

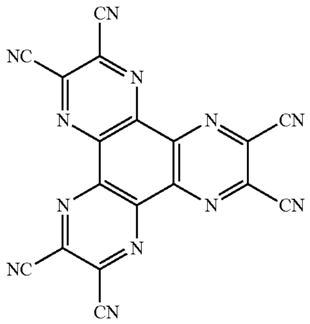

<F4-TCNQ>

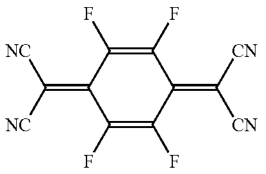

When the hole injection layer, hole transport layer, or H-functional layer further includes a charge-generating material, the charge-generating material may be homogeneously dispersed or inhomogeneously distributed in the layer.

A buffer layer may be disposed between at least one of the HIL, HTL, and H-functional layer, and the EML. The buffer layer may compensate for an optical resonance distance of light according to a wavelength of the light emitted from the EML, and thus may increase efficiency. The butter layer may include any hole injecting material or hole transporting material that are widely known. In some other embodiments, the buffer layer may include the same material as one of the materials included in the HIL, HTL, and H-functional layer that underly the buffer layer.

Then, an EML may be formed on the HTL, H-functional layer, or buffer layer by vacuum deposition, spin coating, casting, Langmuir-Blodget (LB) deposition, or the like. When the EML is formed using vacuum deposition or spin coating, the deposition and coating conditions may be similar to those for the formation of the HIL, though the conditions for deposition and coating may vary according to the material that is used to form the EML.

The EML may be formed using the compound of Formula 1 above, or any of a variety of known light-emitting materials, such as known hosts and dopants. Dopants that may be used to form the EML may include either a fluorescent dopant or a phosphorescent dopant which are widely known in the art.

Non-limiting example of the known host are $Alq_3$, 4,4'-N, N'-dicarbazole-biphenyl (CBP), poly(n-vinylcarbazole) (PVK), 9,10-di(naphthalene-2-yl)anthracene (ADN), TCTA, 1,3,5-tris(N-phenylbenzimidazole-2-yl)benzene (TPBI), 3-tert-butyl-9,10-di-2-naphthylanthracene (TBADN), E3, distyrylarylene (DSA), dmCBP (see a formula below), and Compounds 501 to 509 below.

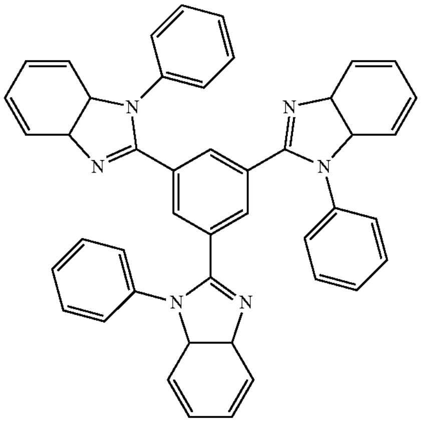

TPBI

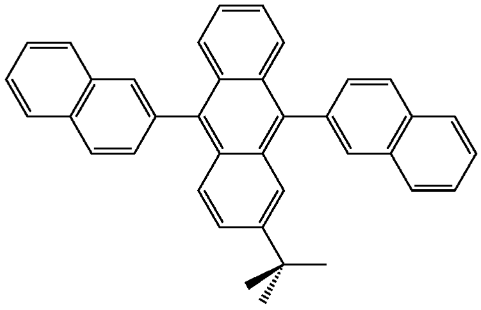

TBADN

E3

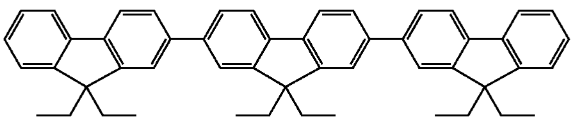

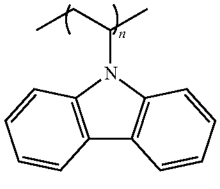

PVK

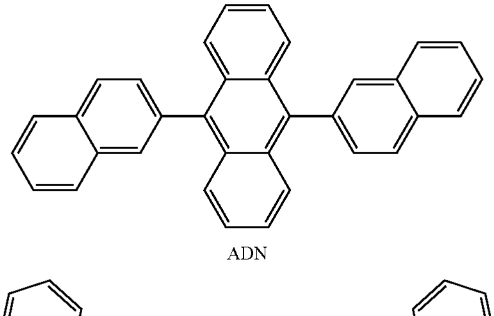

ADN

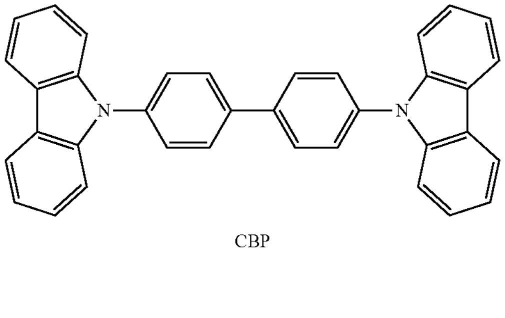

CBP

-continued
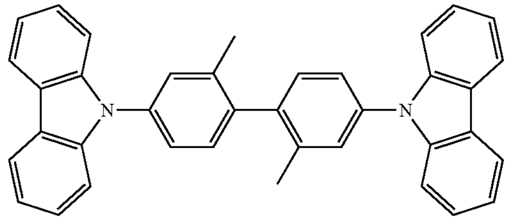
dmCBP
501
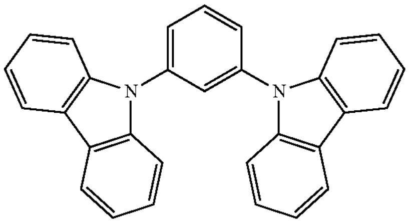
502
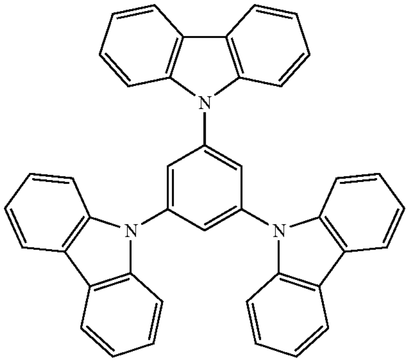
503
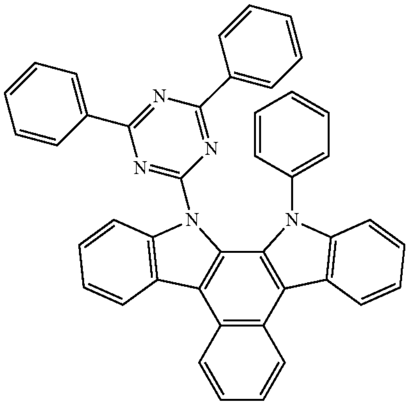
-continued
504
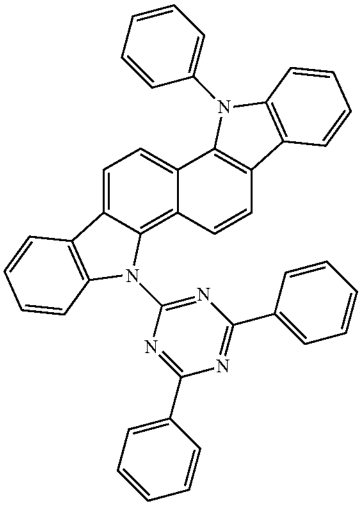
505
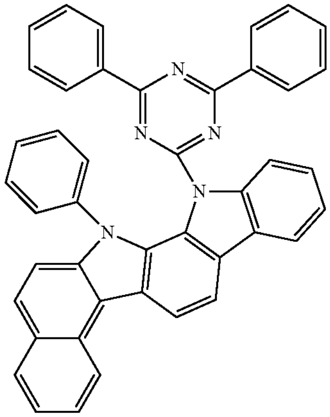
506
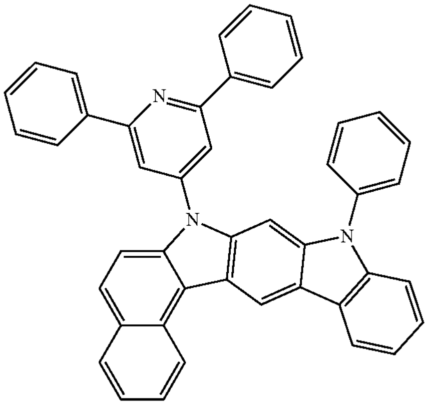

-continued

507

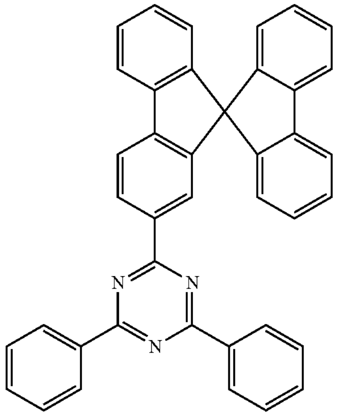

508

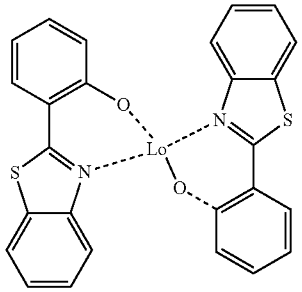

509

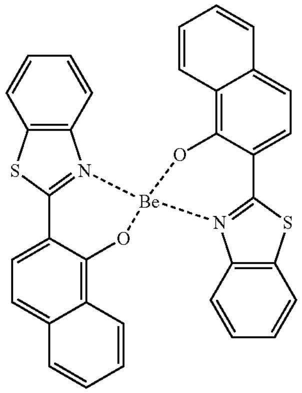

In some embodiments, an anthracene-based compound represented by Formula 400 below may be used as the host.

<Formula 400>

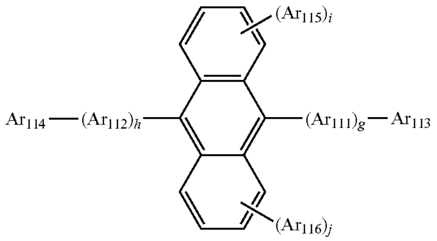

In Formula 400, $Ar_{111}$ and $Ar_{112}$ are each independently a substituted or unsubstituted $C_6$-$C_{60}$ arylene group; $Ar_{113}$ to $Ar_{116}$ are each independently a substituted or unsubstituted $C_1$-$C_{10}$ alkyl group, or a substituted or unsubstituted $C_5$-$C_{60}$ aryl group; and g, h, I, and j are each independently an integer from 0 to 4.

In some embodiments, $Ar_{111}$ and $Ar_{112}$ in Formula 400 may be each independently a phenylene group, a naphthylene group, a phenanthrenylene group, or a pyrenylene group; or a phenylene group, a naphthylene group, a phenanthrenylene group, a fluorenyl group, or a pyrenylene group that are substituted with at least one of a phenyl group, a naphthyl group, and an anthryl group.

In Formula 400 above, g, h, I, and j may be each independently 0, 1, or 2.

In some embodiments, $Ar_{113}$ to $Ar_{116}$ in Formula 400 may be each independently one of a $C_1$-$C_{10}$ alkyl group substituted with at least one of a phenyl group, a naphthyl group, and an anthryl group; a phenyl group; a naphthyl group; an anthryl group; a pyrenyl group; a phenanthrenyl group; a fluorenyl group; a phenyl group, a naphthyl group, an anthryl group, a pyrenyl group, a phenanthrenyl group, and a fluorenyl group that are substituted with at least one of a deuterium atom, a halogen atom, a hydroxyl group, a cyano group, a nitro group, an amino group, an amidino group, hydrazine, hydrazone, a carboxyl group or a salt thereof, a sulfonic acid group or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a phenyl group, a naphthyl group, an anthryl group, a pyrenyl group, a phenanthrenyl group, and a fluorenyl group, but are not limited thereto.

For example, the anthracene-based compound of Formula 400 above may be one of the compounds represented by the following formulae, but is not limited thereto:

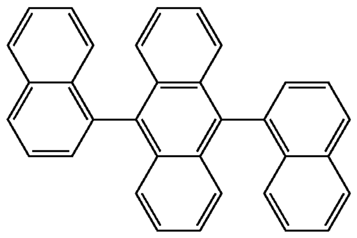

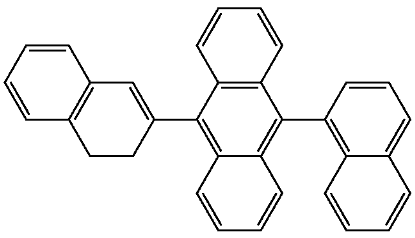

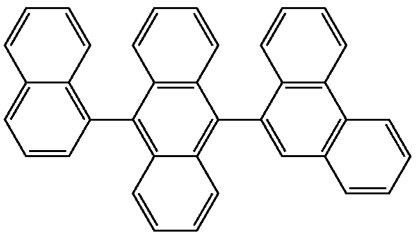

-continued
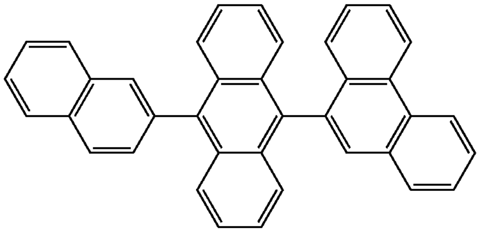
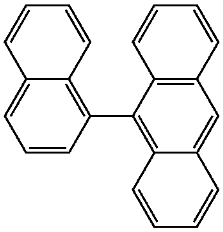
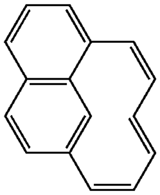
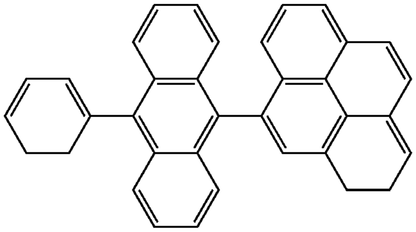
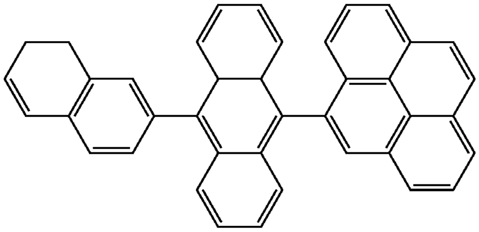
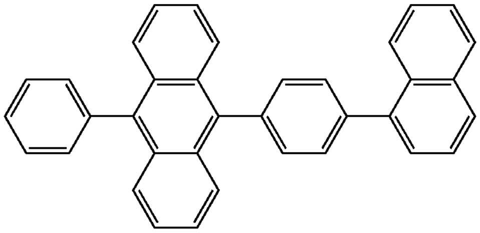
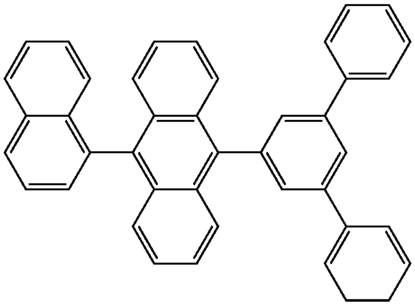
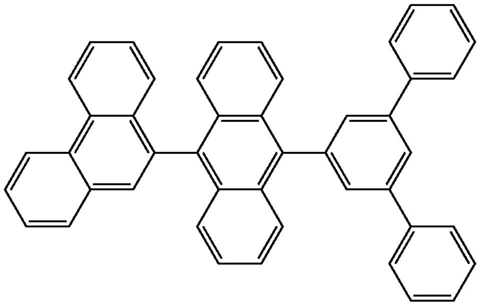
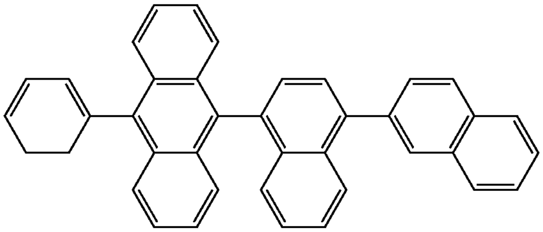
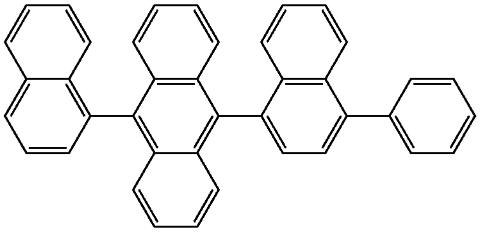
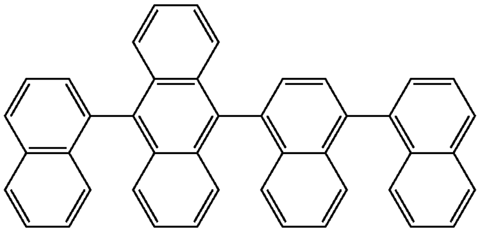
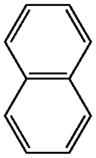
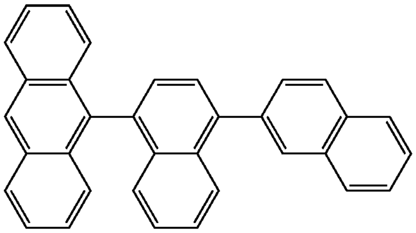
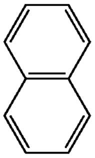
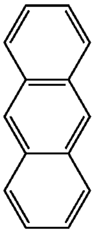
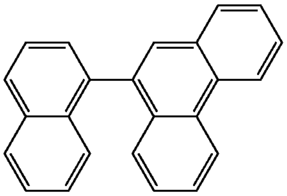

-continued
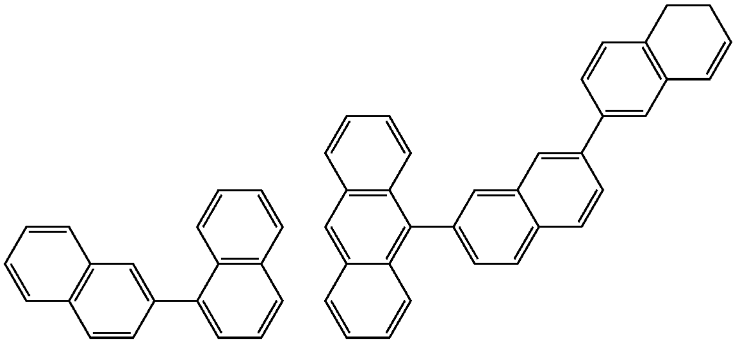
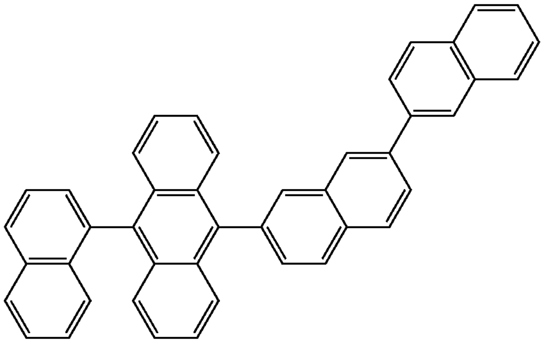
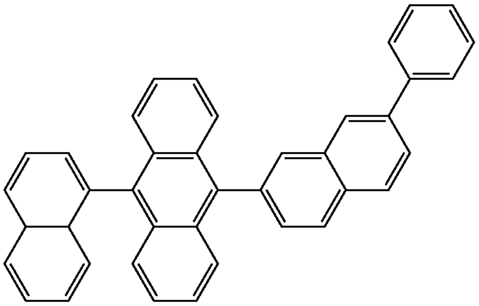
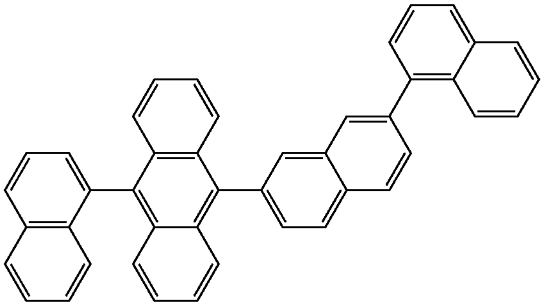
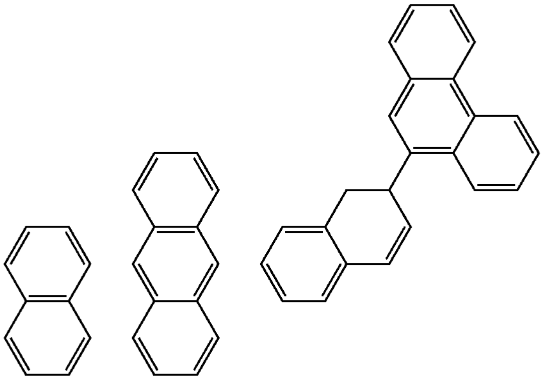
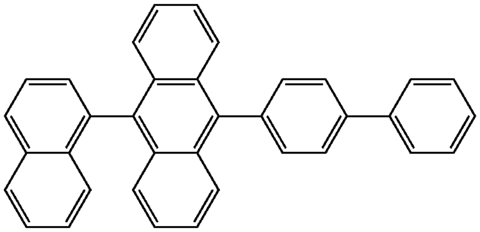
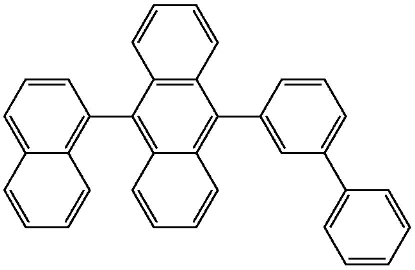
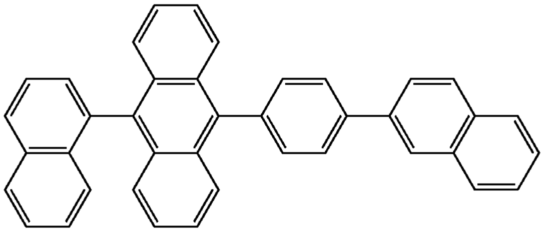
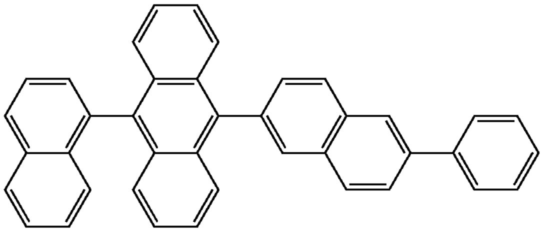

-continued
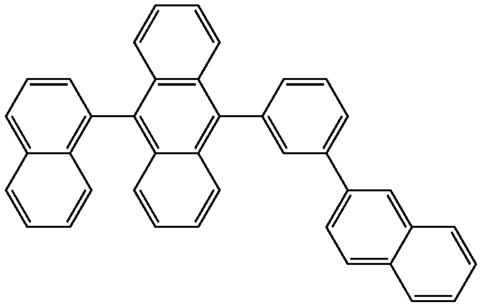
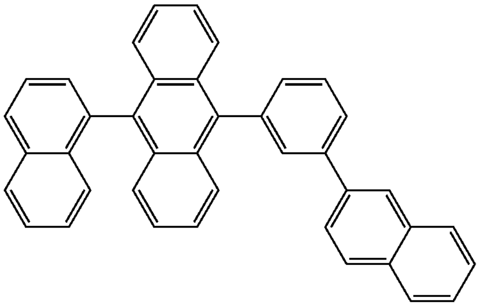
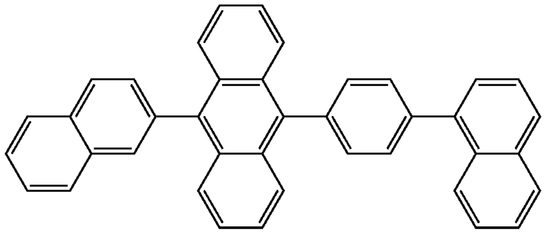
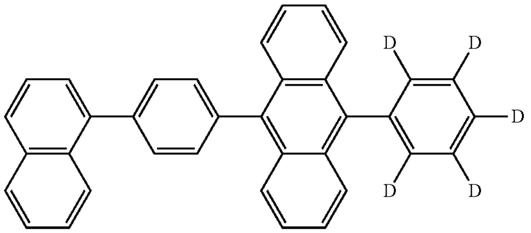
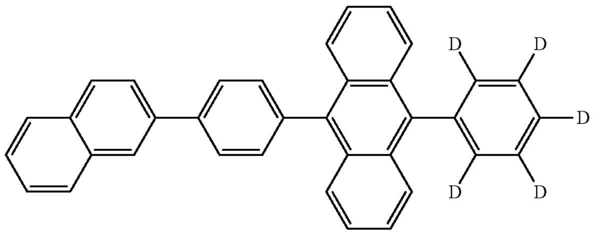
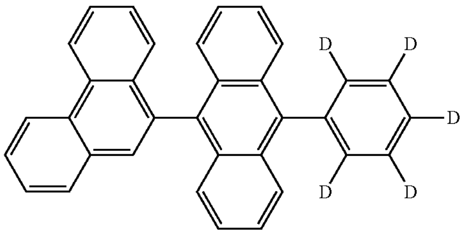
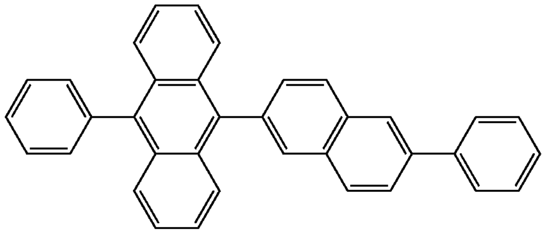
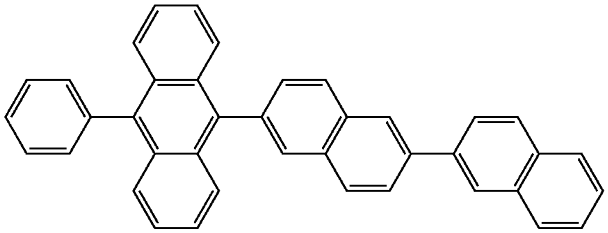
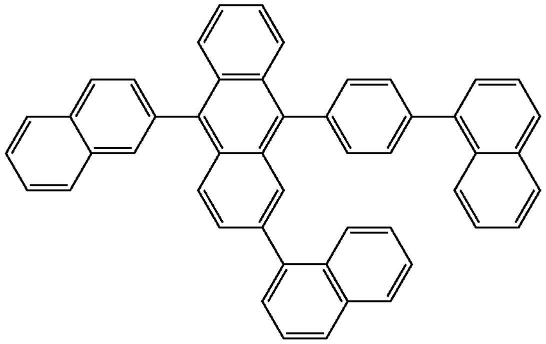
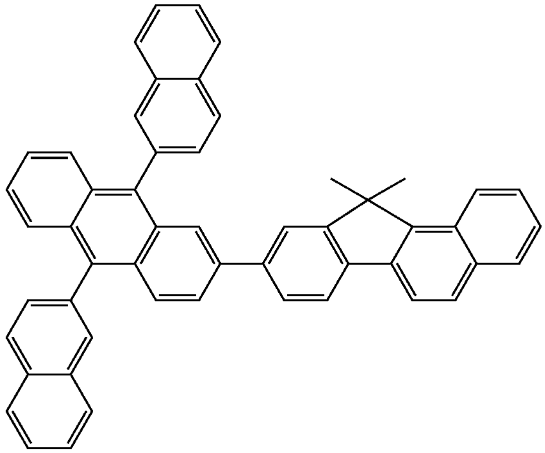

-continued

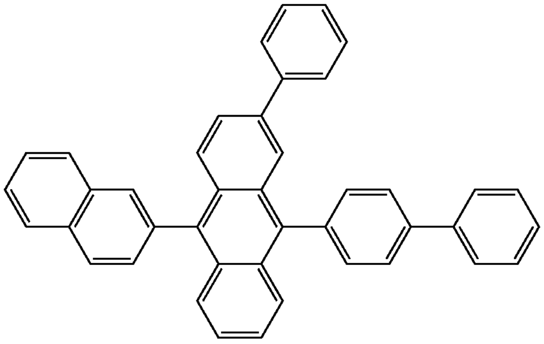

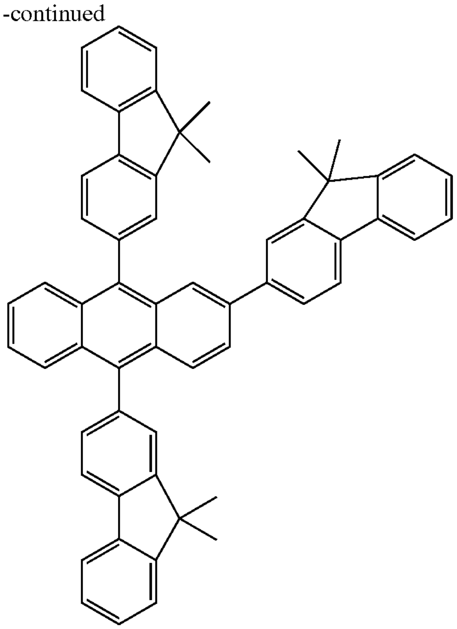

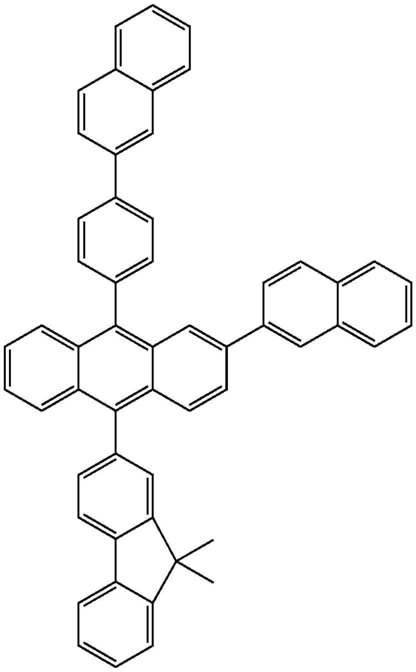

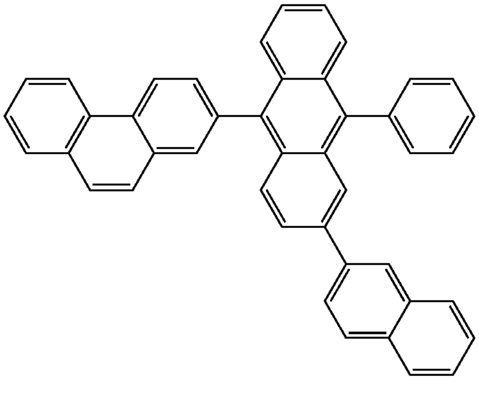

In some embodiments, an anthracene-based compound represented by Formula 401 below may be used as the host.

<Formula 401>

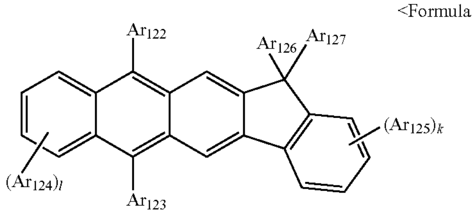

$Ar_{122}$ to $Ar_{125}$ in Formula 401 above may be defined as described above in conjunction with $Ar_{113}$ of Formula 400, and thus detailed descriptions thereof will not be provided here.

$Ar_{126}$ and $Ar_{127}$ in Formula 401 above may be each independently a $C_1$-$C_{10}$ alkyl group, for example, a methyl group, an ethyl group, or a propyl group.

In Formula 401, k and l may be each independently an integer from 0 to 4, for example, 0, 1, or 2.

For example, the anthracene compound of Formula 401 above may be one of the compounds represented by the following formulae, but is not limited thereto:

-continued

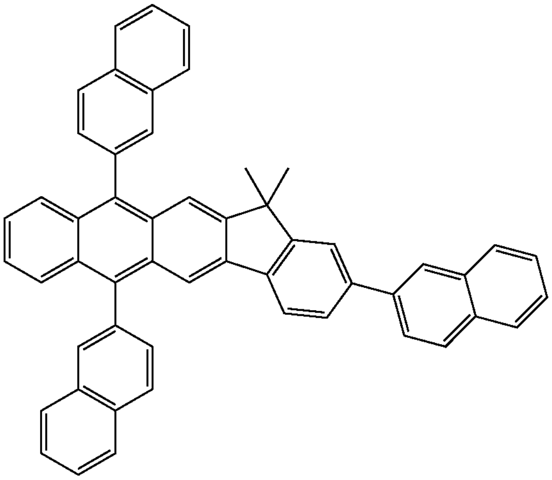

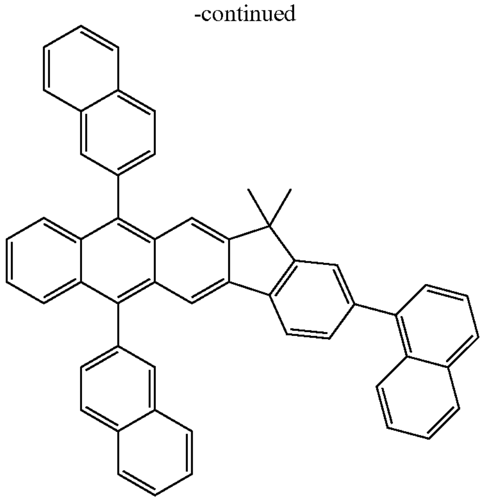

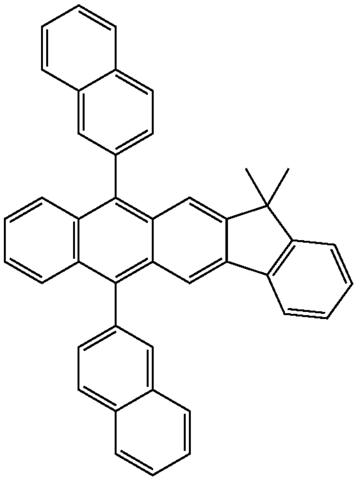

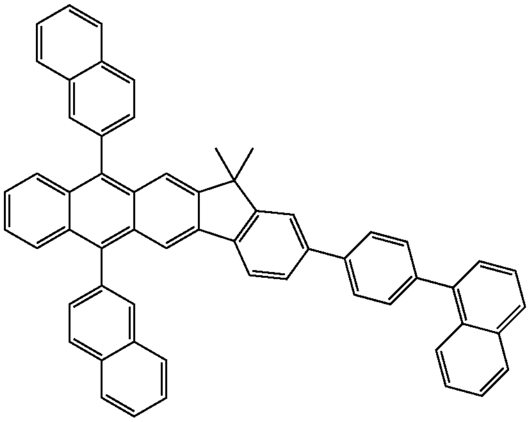

When the organic light-emitting device is a full color organic light-emitting device, the emission layer may be patterned into a red emission layer, a green emission layer, and a blue emission layer.

At least one of the red EML, the green EML, and the blue EML may include a dopant below (ppy=phenylpyridine).

Further to the compound of Formula 1 above, non-limiting examples of the blue dopant are compounds represented by the following formulae.

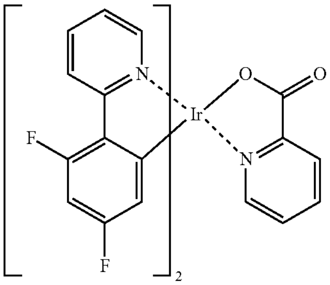

$F_2Irpic$

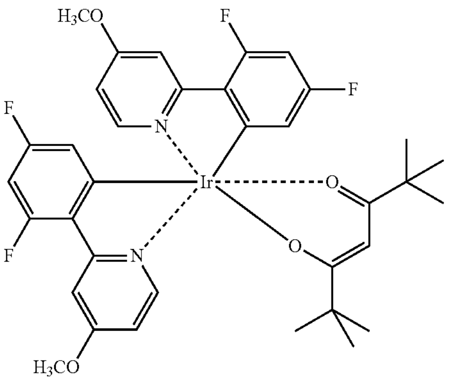

$(F_2ppy)_2Ir(tmd)$

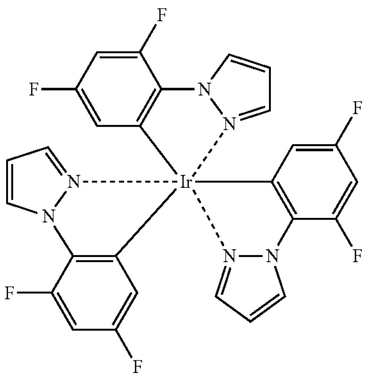

$Ir(dfppz)_3$

-continued
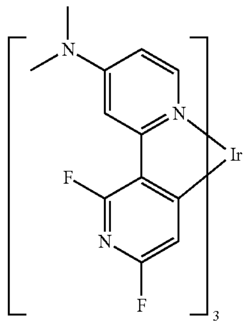
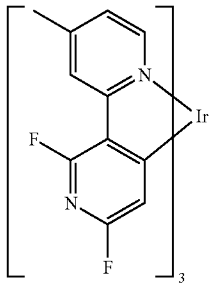
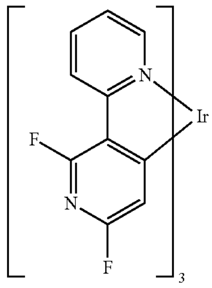
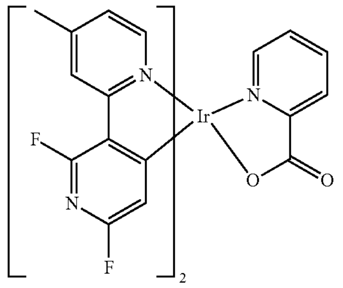
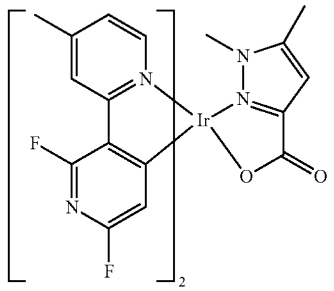
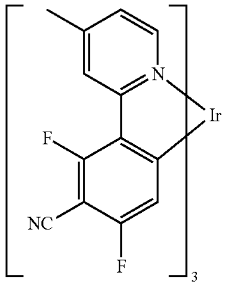
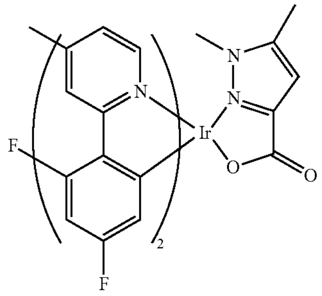
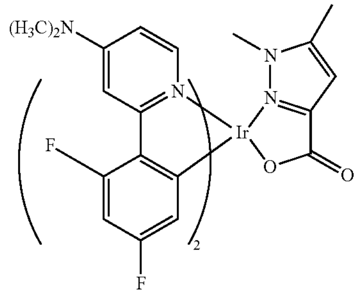
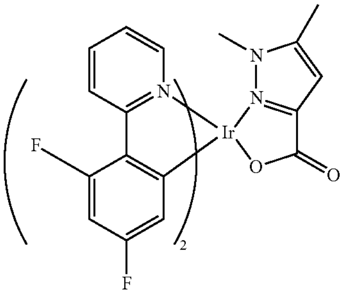
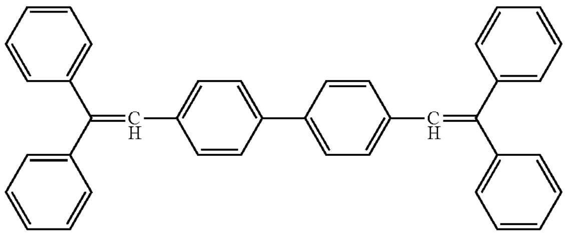
DPVBi
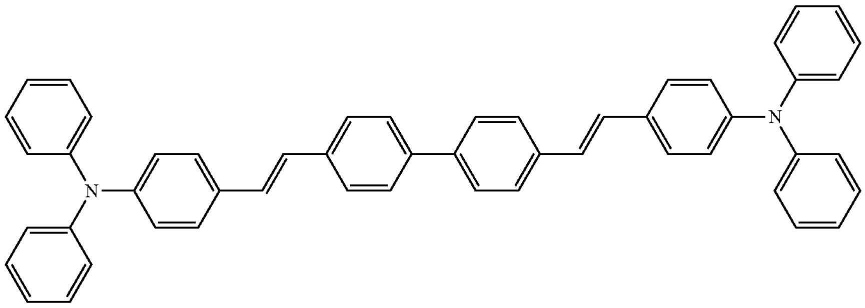
DPAVBi
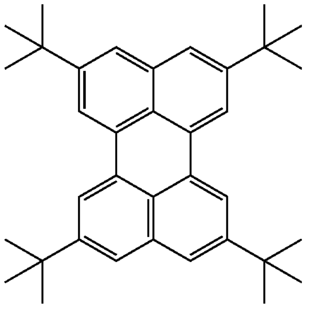
TBPe Non-limiting examples of the red dopant are compounds represented by the following formulae.
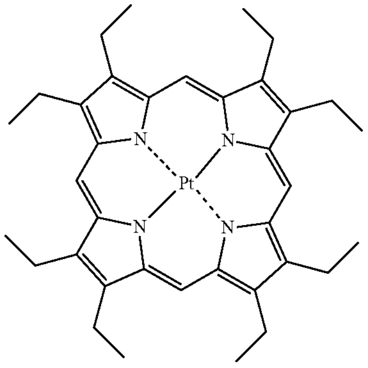
PtOEP
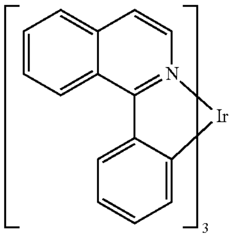
$Ir(piq)_3$
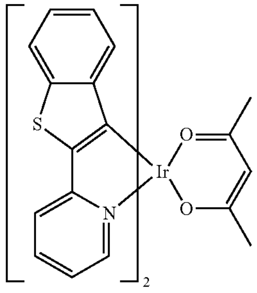
$Btp_2Ir(acac)$
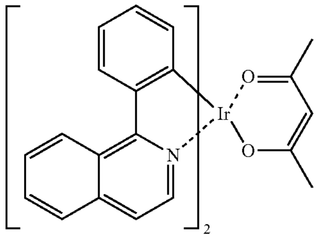
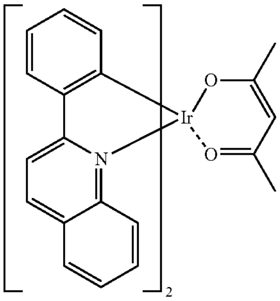
$Ir(pq)_2(acac)$
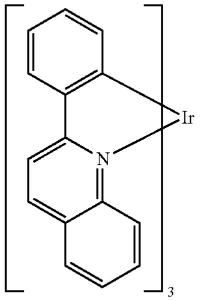
$Ir(2\text{-}phq)_3$
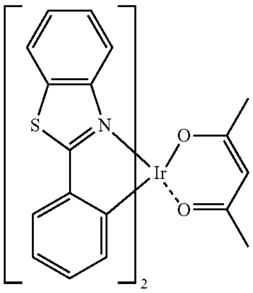
$Ir(BT)_2(acac)$
-continued
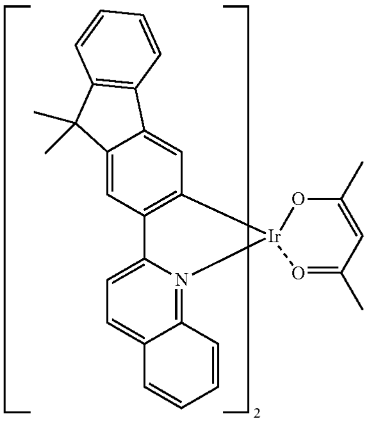
$Ir(flq)_2(acac)$
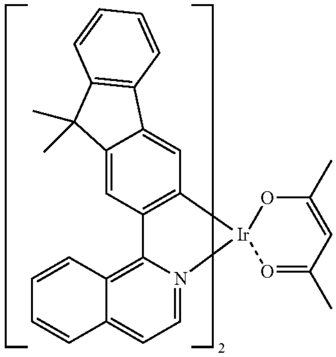
$Ir(fliq)_2(acac)$
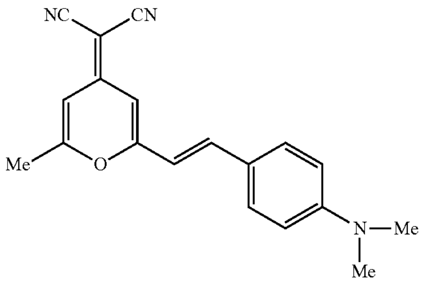
DCM
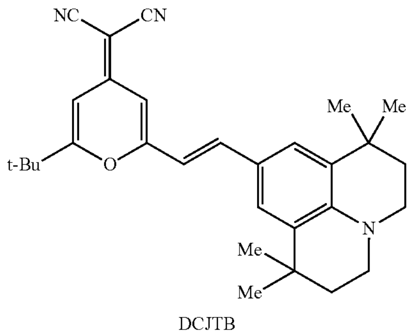 [SMILES: CC(C)(C)C1=CC(=C(C#N)C#N)C=C(/C=C/c2cc3c4c(c2)C(C)(C)CCN4CCC3(C)C)O1]
DCJTB Non-limiting examples of the green dopant are compounds represented by the following formulae.
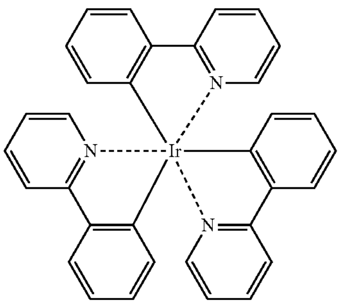
Ir(ppy)3
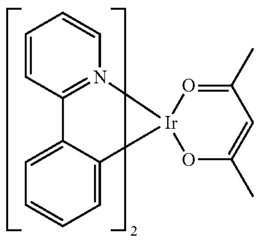
Ir(ppy)2(acac)
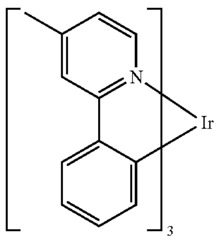
Ir(mpyp)3
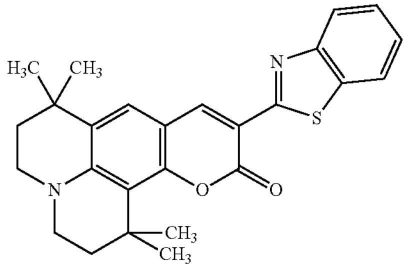
C545T
Non-limiting examples of the dopant that may be used in the EML are Pd complexes or Pt complexes represented by the following formulae.
D1
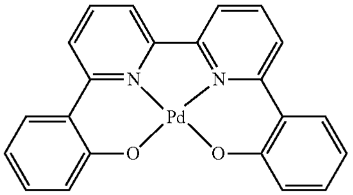
D2
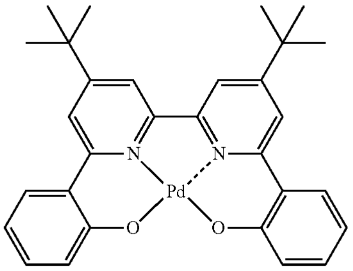
-continued
D3
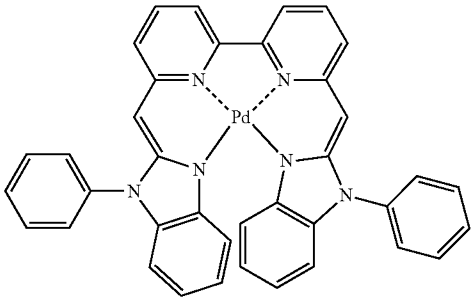
D4
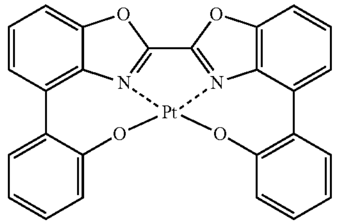
D5
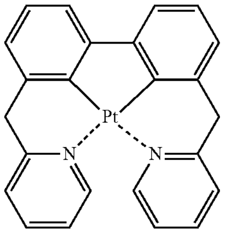
D6
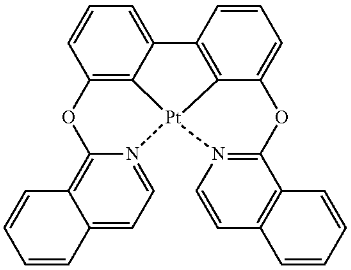
D7
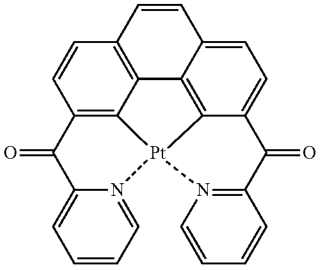
D8
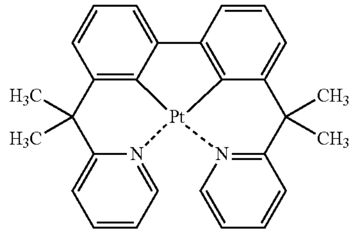

-continued
D9
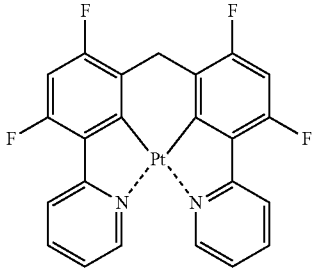
D10
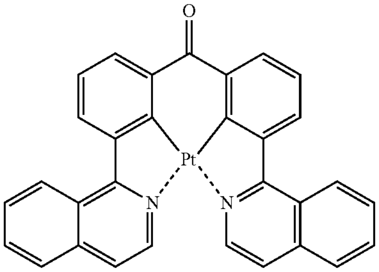
D11
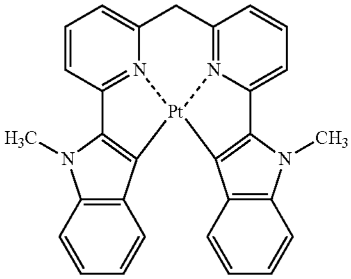
D12
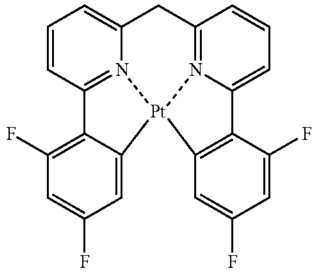
D13
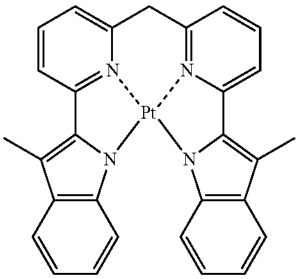
-continued
D14
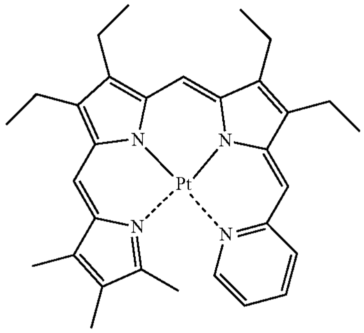
D15
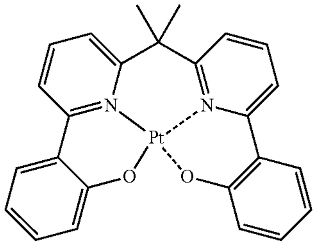
D16
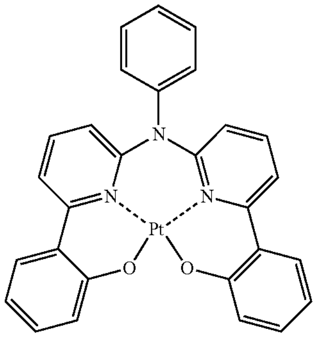
D17
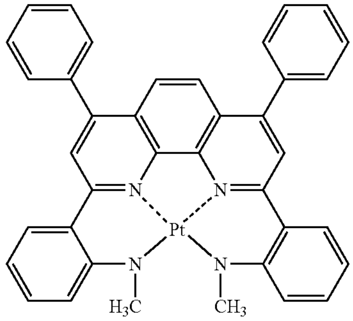
D18
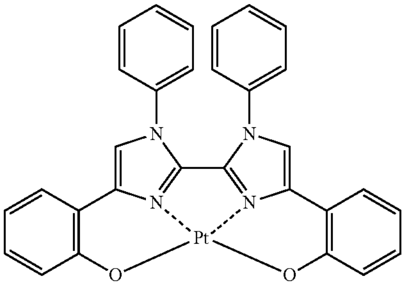

-continued
D19
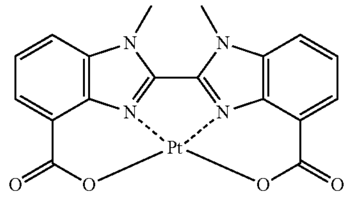
D20
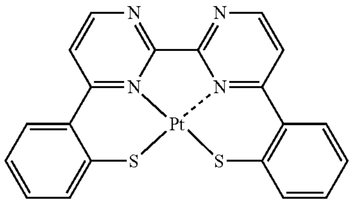
D21
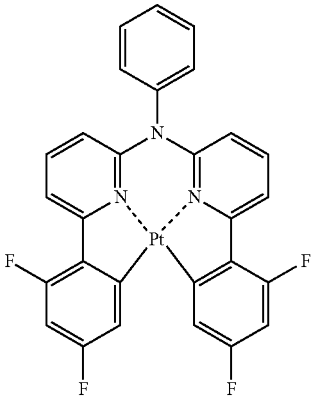
D22
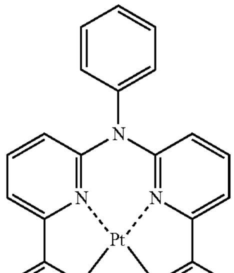
D23
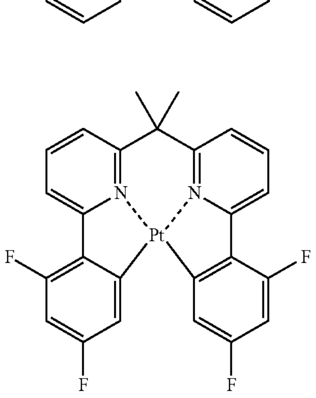
-continued
D24
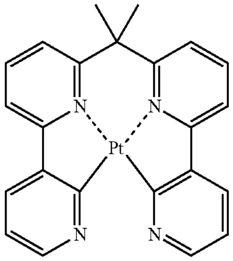
D25
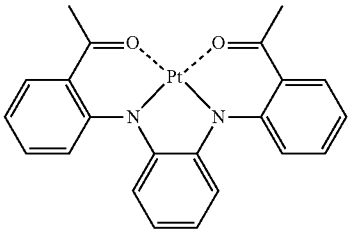
D26
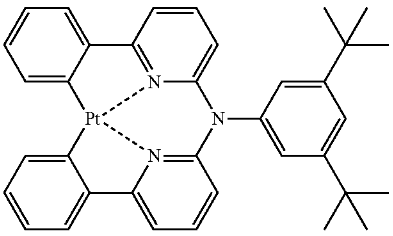
D27
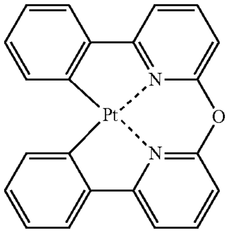
D28
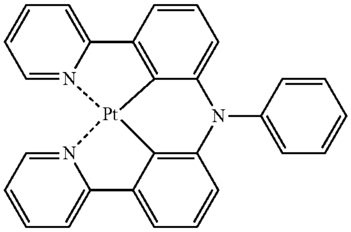
D29
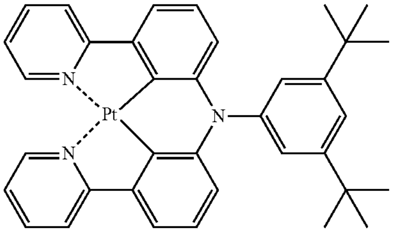

-continued
D30
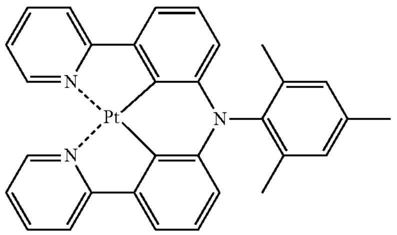
D31
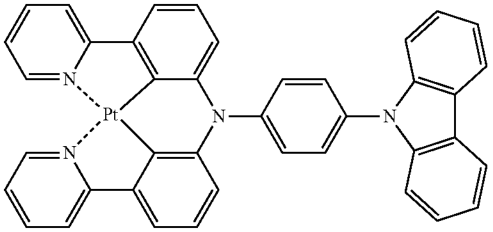
D32
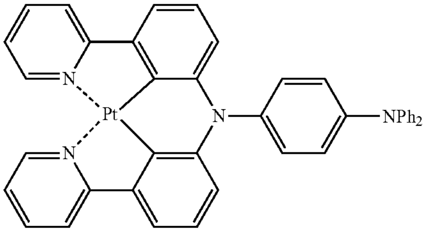
D33
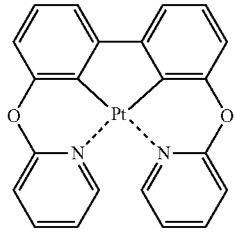
D34
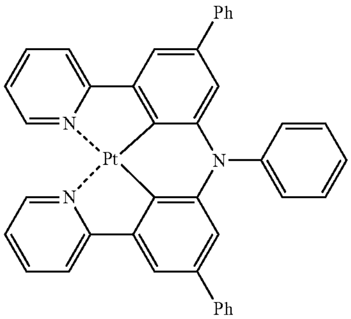
D35
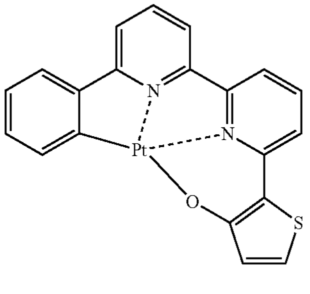
-continued
D36
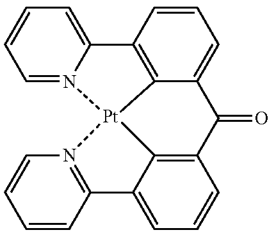
D37
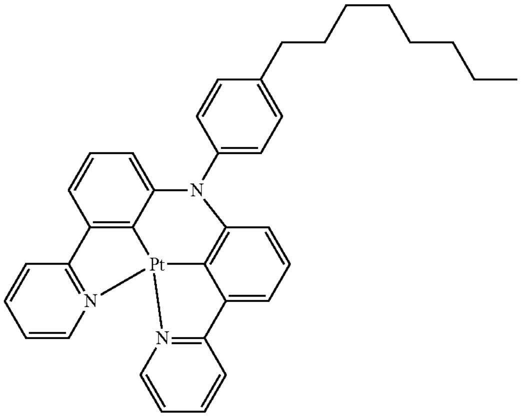
D38
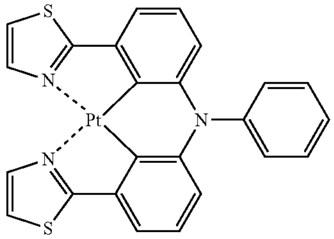
D39
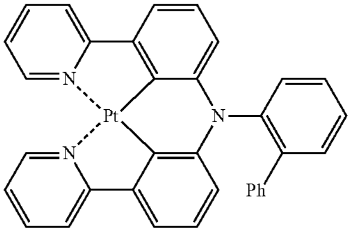
D40
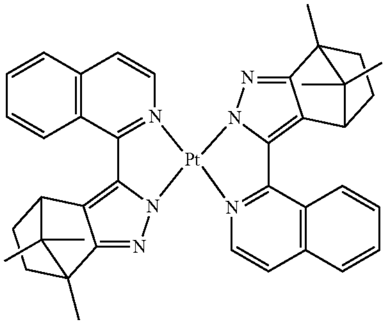

-continued
D41
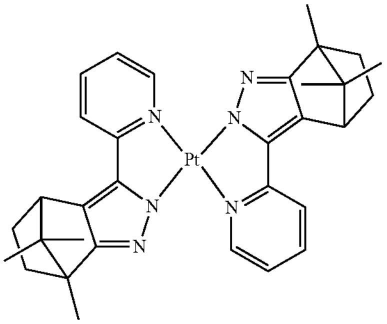
D42
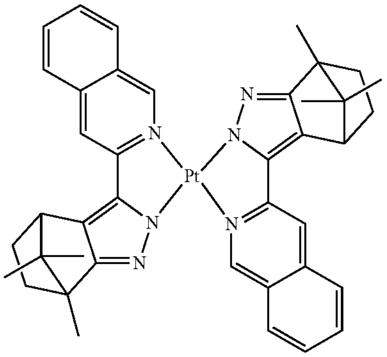
D43
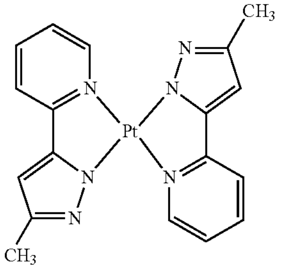
D44
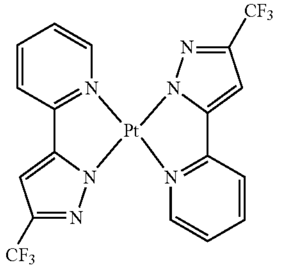
D45
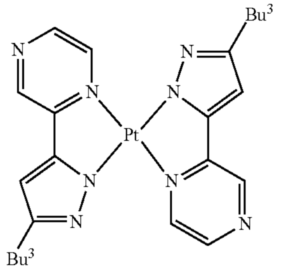
-continued
D46
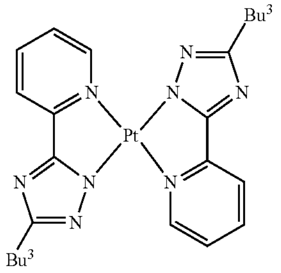
D47
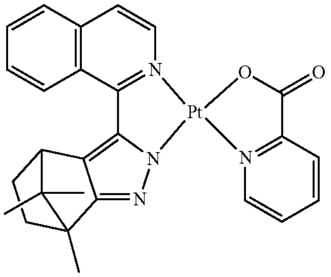
D48
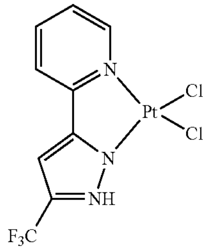
D49
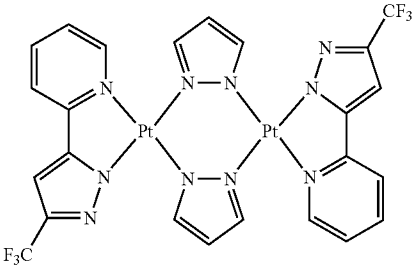
D50
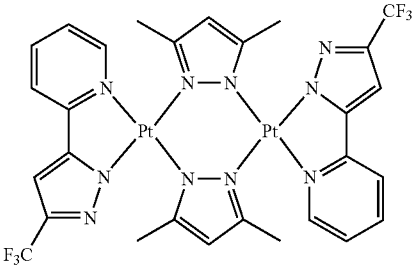
Non-limiting examples of the dopant that may be used in the EML are Os complexes represented by the following formulae.

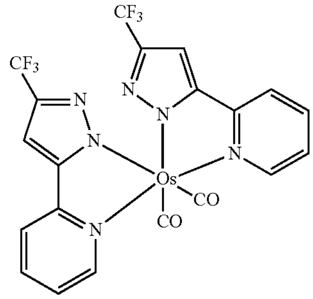

Os(fppz)$_2$(CO)$_2$

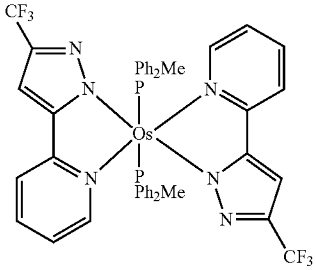

Os(fppz)$_2$(PPh$_2$Me)$_2$

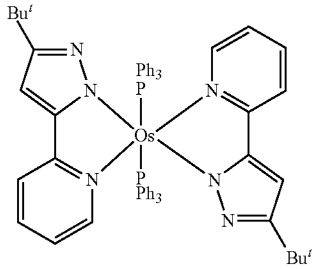

Os(bppz)$_2$(PPh$_3$)$_2$

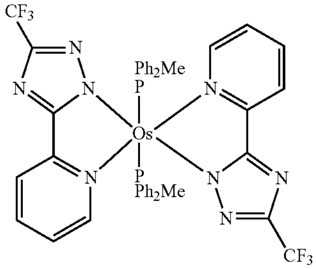

Os(fptz)$_2$(PPh$_2$Me)$_2$

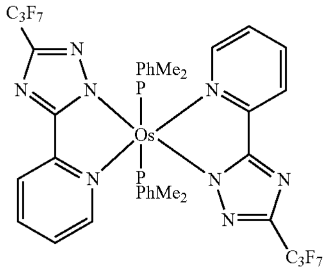

Os(hptz)$_2$(PPhMe$_2$)$_2$

When the EML includes both a host and a dopant, the amount of the dopant may be from about 0.01 to about 15 parts by weight based on 100 parts by weight of the host. However, the amount of the dopant is not limited to this range.

The thickness of the EML may be from about 100 Å to about 1000 Å, and in some embodiments, from about 200 Å to about 600 Å. When the thickness of the EML is within these ranges, the EML may have good light emitting ability without a substantial increase in driving voltage.

Then, an ETL may be formed on the EML by vacuum deposition, spin coating, casting, or the like. When the ETL is formed using vacuum deposition or spin coating, the deposition and coating conditions may be similar to those for the formation of the HIL, though the deposition and coating conditions may vary according to a compound that is used to form the ETL.

A material for forming the ETL may be any known material that can stably transport electrons injected from an electron injecting electrode (cathode). Non-limiting examples of materials for forming the ETL are a quinoline derivative, such as tris(8-quinolinorate)aluminum (Alq3), TAZ, BAlq, beryllium bis(benzoquinolin-10-olate (Bebq$_2$), 9,10-di(naphthalene-2-yl)anthracene (ADN), Compound 201, and Compound 202, but are not limited thereto.

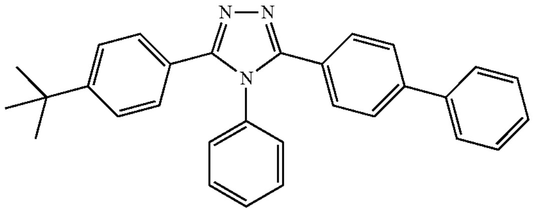

TAZ

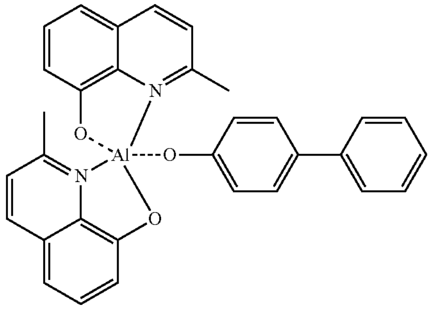

BAlq

<Compound 201>

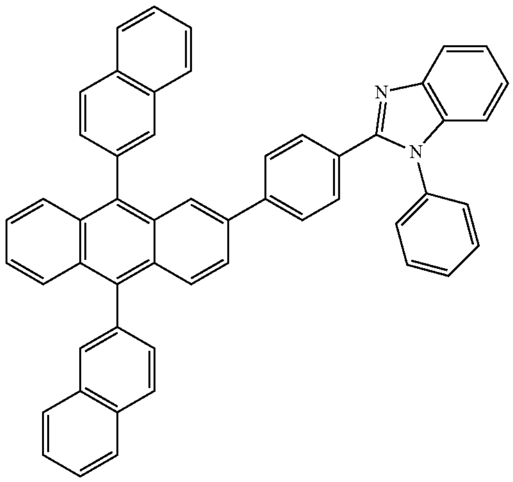

-continued

<Compound 202>

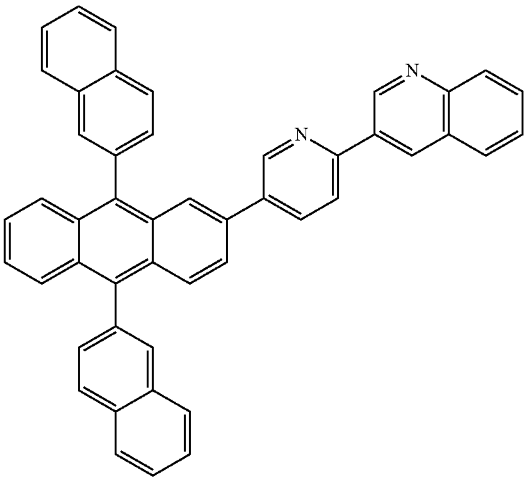

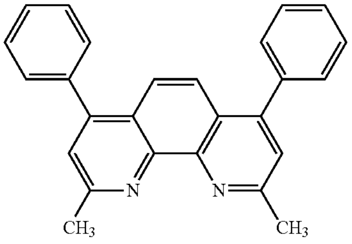

BCP

The thickness of the ETL may be from about 100 Å to about 1000 Å, and in some embodiments, from about 150 Å to about 500 Å. When the thickness of the ETL is within these ranges, the ETL may have satisfactory electron transporting ability without a substantial increase in driving voltage.

In some embodiments the ETL may further include a metal-containing material, in addition to any known electron-transporting organic compound.

The metal-containing material may include a lithium (Li) complex. Non-limiting examples of the Li complex are lithium quinolate (LiQ) and Compound 203 below:

<Compound 203>

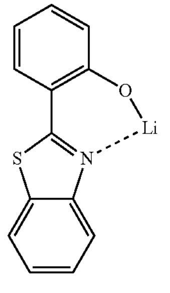

Then, an EIL, which facilitates injection of electrons from the cathode, may be formed on the ETL. Any known electron-injecting material may be used to form the EIL.

Non-limiting examples of the known electron-injecting material for the EIL are LiF, NaCl, CsF, $Li_2O$, and BaO. The deposition and coating conditions for forming the EIL 18 may be similar to those for the formation of the HIL, though the deposition and coating conditions may vary according to the material that is used to form the EIL 18.

The thickness of the EIL may be from about 1 Å to about 100 Å, and in some embodiments, from about 3 Å to about 90 Å. When the thickness of the EIL is within these ranges, the EIL may have satisfactory electron injection ability without a substantial increase in driving voltage.

Finally, the second electrode is disposed on the organic layer. The second electrode may be a cathode that is an electron injection electrode. A material for forming the second electrode may be a metal, an alloy, an electro-conductive compound, which have a low work function, or a mixture thereof. In this regard, the second electrode may be formed of lithium (Li), magnesium (Mg), aluminum (Al), aluminum (Al)-lithium (Li), calcium (Ca), magnesium (Mg)-indium (In), magnesium (Mg)-silver (Ag), or the like, and may be formed as a thin film type transmission electrode. In some embodiments, to manufacture a top-emission light-emitting device, the transmission electrode may be formed of indium tin oxide (ITO) or indium zinc oxide (IZO).

Although the organic light-emitting device of FIG. 1 is described above, the present invention is not limited thereto.

When a phosphorescent dopant is used in the EML, a HBL may be formed between the ETL and the EML or between the E-functional layer and the EML by using vacuum deposition, spin coating, casting, Langmuir-Blodgett (LB) deposition, or the like, in order to prevent diffusion of triplet excitons or holes into the ETL. When the HBL is formed using vacuum deposition or spin coating, the conditions for deposition and coating may be similar to those for the formation of the HIL, although the conditions for deposition and coating may vary according to the material that is used to form the HBL. Any known hole-blocking material may be used. Non-limiting examples of hole-blocking materials are oxadiazole derivatives, triazole derivatives, and phenanthroline derivatives. For example, BCP (2,9-dimethyl-4,7-diphenyl-1,10-phenanthroline) represented by the following formula may be used as a material for the HBL.

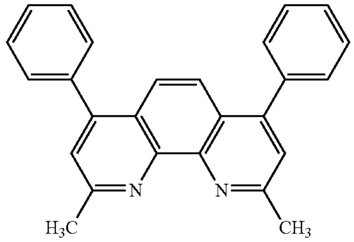

BCP

The thickness of the HBL may be from about 20 Å to about 1000 Å, and in some embodiments, from about 30 Å to about 300 Å. When the thickness of the HBL is within these ranges, the HBL may have improved hole blocking ability without a substantial increase in driving voltage.

According to embodiments of the present invention, the organic light-emitting device may be included in various types of flat panel display devices, such as in a passive matrix organic light-emitting display device or in an active matrix organic light-emitting display device. In particular, when the organic light-emitting device is included in an active matrix organic light-emitting display device including a thin-film transistor, the first electrode on the substrate may function as a pixel electrode, electrically connected to a source electrode or a drain electrode of the thin-film transistor. Moreover, the organic light-emitting device may also be included in flat panel display devices having double-sided screens.

In some embodiments the organic layer of the organic light-emitting device may be formed of the compound of Formula 1 by using a deposition method or may be formed using a wet method of coating a solution of the compound of Formula 1.

Hereinafter, the present invention will be described in detail with reference to the following synthesis examples and other examples. However, these examples are for illustrative purposes only and are not intended to limit the scope of the present invention.

EXAMPLES

Synthesis Example 1

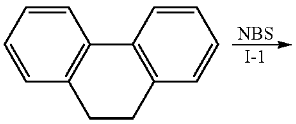

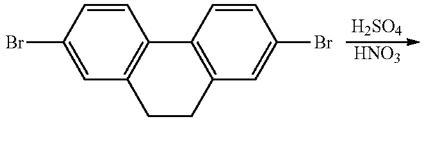

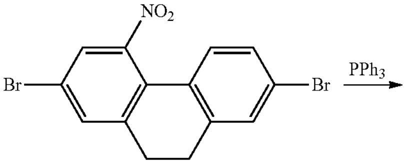

I-2

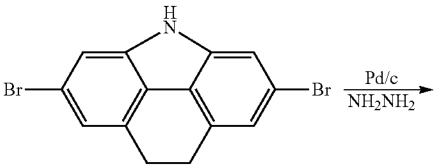

I-3

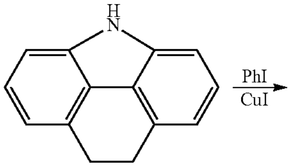

I-4

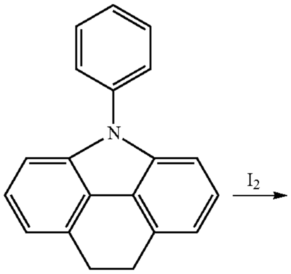

I-5

-continued

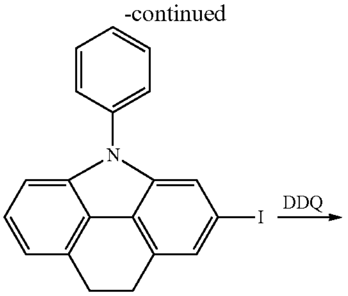

I-6

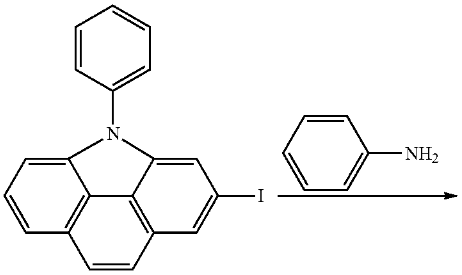

I-7

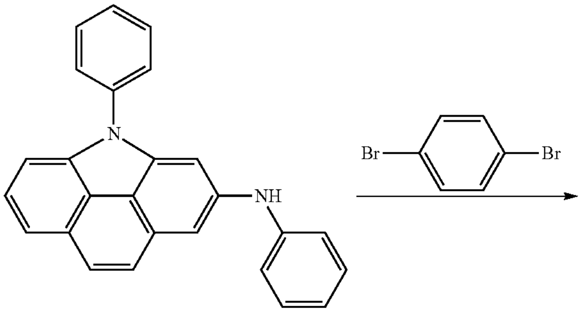

I-8

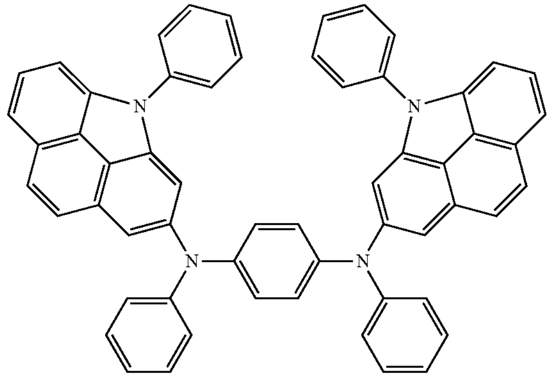

1

Synthesis of Intermediate I-1

10.0 g (55.4 mmol) of 9,10-dihydrophenanthrene, 21.8 g (121.0 mmol) of N-bromosuccinimide, and 0.5 g (2.7 mmol) of p-TsOH were dissolved in 30 mL of acetonitrile, and then stirred at about 50° C. for about 12 hours. The reaction solution was cooled down to room temperature, and stirred for about 30 minutes to precipitate crystals. The crystals were collected through a vacuum filter, and washed with methanol to obtain 8.4 g (Yield 45%) of Intermediate I-1 as gray crystals. This compound was identified using liquid chromatography-mass spectroscopy (LC-MS).

$C_{14}H_{10}Br_2$ $M^+$ 336.9

Synthesis of Intermediate I-2

After 5.0 g (15.0 mmol) of Intermediate I-1 was completely dissolved in 50 mL of dichloromethane, 1.7 g (30.0 mmol) of nitric acid was added, and 1.5 g (15.0 mmol) of sulfuric acid was slowly dropwise added thereto to obtain a solution, which was then stirred at about 30° C. for about 6 hours. After completion of the reaction, the reaction solution was cooled down to room temperature, 50 mL of methanol was added thereto and stirred for about 2 hours to precipitate crystals. The crystals were collected through a vacuum filter, and washed with methanol to obtain 5.2 g (Yield 90%) of Intermediate I-2 as yellow crystals. This compound was identified using LC-MS.

$C_{14}H_9Br_2NO_2$ $M^+$ 381.9

Synthesis of Intermediate I-3

After 4.6 g (12.0 mmol) of Intermediate I-2 was dissolved in 30 mL of o-dichloromethane and heated until completely dissolved, 4.7 g (18.0 mmol) of triphenylphosphine was added thereto and stirred at about 180° C. for about 3 hours. After the reaction solution was cooled down to room temperature, the solvent was removed by evaporation to obtain a residue, which was then separated and purified using silica gel column chromatography, and washed with methanol to obtain 2.9 g of Intermediate I-3 (Yield: 70%) as white crystals. This compound was identified using LC-MS.

$C_{14}H_9Br_2N$ $M^+$ 349.9

Synthesis of Intermediate I-4

After 10 g (28.5 mmol) of Intermediate I-3 and 0.03 g (0.28 mmol) of Pd/c were dissolved in 100 mL of ethanol at room temperature, the temperature was increased to 50° C., and 5.48 g (171 mmol) of hydrazine was dropwise added thereto and stirred for about 24 hours. The reaction solution was cooled down to room temperature, washed with acetone, and then added with 100 mL of ice water to obtain 3.63 g of Intermediate I-4 (Yield: 66%) as white crystals. This compound was identified using LC-MS.

$C_{14}H_{11}N$ M+ 194.1

Synthesis of Intermediate I-5

1.93 g (10.0 mmol) of Intermediate I-4, 2.5 g (12.0 mmol) of iodobenzene, 0.2 g (1.0 mmol) of 1,10-phenanthroline, 0.2 g (2.0 mmol) of CuI, and 4.1 g (30.0 mmol) of $K_2CO_3$ were dissolved in 30 mL of DMF (N,N-dimethylformamide) to obtain a solution, which was then stirred at about 80° C. for about 24 hours. The reaction solution was cooled to room temperature, followed by three times of extraction with 30 mL of water and 40 mL of diethylether. The organic phase was collected and was dried using magnesium sulfate to evaporate the solvent. The residue was separated and purified using silica gel column chromatography to obtain 2.39 g of Intermediate I-5 (Yield: 89%). This compound was identified using LC-MS.

$C_{20}H_{15}N$ $M^+$ 270.1

Synthesis of Intermediate I-6

After 10 g (37.1 mmol) of Intermediate I-5 was completely dissolved in 100 mL of dichloromethane, 3.58 g (14.1 mmol) of iodine and 2.38 g (11.13 mmol) of $KIO_3$ were added over five times, each by one fifth. After being stirred for about 6 hours, the reaction solution was washed with methanol to obtain 8.06 g (Yield 55%) of Intermediate I-6. This compound was identified using LC-MS.

$C_{20}H_{14}IN$ M+ 396.1

Synthesis of Intermediate I-7

After 10 g (25.3 mmol) of Intermediate I-6 was dissolved in 100 mL of toluene in an oxygen atmosphere, 1.57 g (7.6 mmol) of 2,3-dichloro-5,6-dicyano-1,4-benzoquinone and 0.52 g (7.6 mmol) of $NaNO_2$ were added thereto. After being stirred at about 110° C. for about 6 hours and completion of the reaction, the reaction solution was cooled down to room temperature, and the solvent was evaporated. The residue was separated and purified using silica gel column chromatography to obtain 8.94 g of Intermediate I-7 (Yield: 90%). This compound was identified using LC-MS.

$C_{20}H_{12}IN$ M+ 394.0

Synthesis of Intermediate I-8

3.93 g (10.0 mmol) of Intermediate I-7, 1.02 g (11.0 mmol) of aniline, 0.18 g (0.2 mmol) of $Pd_2(dba)_3$, and 0.02 g (0.2 mmol) of $PtBu_3$, and 2.0 g (20 mmol) of KOtBu were dissolved in 40 mL of toluene to obtain a mixture, which was then stirred at about 85° C. for 4 hours. The reaction solution was cooled to room temperature, followed by three times of extraction with 30 mL of water and 30 mL of diethylether. The organic phase was collected and was dried using magnesium sulfate to evaporate the solvent. The residue was separated and purified using silica gel column chromatography to obtain 3.04 g of Intermediate I-8 (Yield: 85%). This compound was identified using LC-MS.

$C_{26}H_{18}N_2$ M+ 359.1

Synthesis of Compound 1

3.58 g (10.0 mmol) of Intermediate I-8, 1.18 g (5.0 mmol) of 1,4-dibromobenzene, 0.09 g (0.1 mmol) of $Pd_2(dba)_3$, 0.01 g (0.1 mmol) of $PtBu_3$, and 1.0 g (10.0 mmol) of KOtBu were dissolved in 30 mL of toluene to obtain a mixture, which was then stirred at about 85° C. for 4 hours. The reaction solution was cooled to room temperature, followed by three times of extraction with 20 mL of water and 20 mL of diethylether. The organic phase was collected and was dried using magnesium sulfate to evaporate the solvent. The residue was separated and purified using silica gel column chromatography to obtain 3.2 g of Compound 1 (Yield: 81%). This compound was identified using mass spectroscopy/fast atom bombardment (MS/FAB) and $^1H$ nuclear magnetic resonance (NMR).

$C_{58}H_{38}N_4$ cal. 790.31, found 791.31

$^1H$ NMR ($CDCl_3$, 400 MHz) . . . 7.78-7.76 (m, 2H), 7.58-7.47 (m, 12H), 7.43-7.35 (m, 8H), 7.10-7.05 (m, 4H), 6.73 (d, 2H), 6.67-6.63 (m, 2H), 6.59 (s, 4H), 6.38-6.34 (m, 4H)

Synthesis of Compound 7

3.58 g (10.0 mmol) of Intermediate I-8, 1.56 g (5.0 mmol) of 4,4-dibromobiphenyl, 0.09 g (0.1 mmol) of $Pd_2(dba)_3$, 0.01 g (0.1 mmol) of $PtBu_3$, and 1.0 g (10.0 mmol) of KOtBu were dissolved in 30 mL of toluene to obtain a mixture, which was then stirred at about 85° C. for 4 hours. The reaction solution was cooled to room temperature, followed by three times of extraction with 20 mL of water and 20 mL of diethylether. The organic phase was collected and was dried using magnesium sulfate to evaporate the solvent. The residue was separated and purified using silica gel column chromatography to obtain 3.42 g of Compound 7 (Yield: 79%). This compound was identified using MS/FAB and $^1H$ NMR.

$C_{64}H_{42}N_4$ cal. 866.34, found 867.34

$^1H$ NMR ($CDCl_3$, 400 MHz) δ=7.78-7.76 (m, 2H), 7.58-7.34 (m, 24H), 7.10-7.05 (m, 4H), 6.75-6.71 (m, 6H), 6.71-6.62 (m, 2H), 6.38-6.34 (m, 4H)

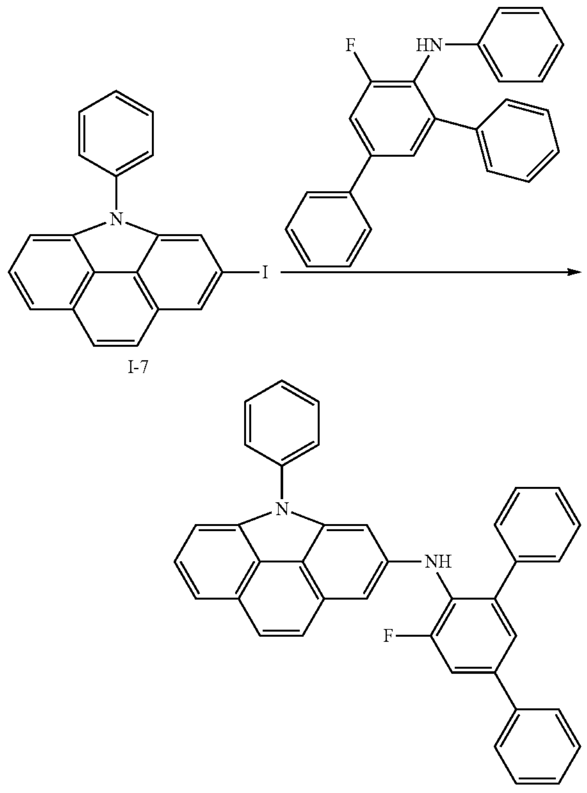

I-7

I-9

Synthesis of Intermediate I-9

Intermediate I-9 was synthesized in the same manner as in the synthesis of Intermediate I-8, except that (5'-fluoro-[1,1'; 3',1"]tetraphenyl-4'-yl)-phenyl-amine, instead of aniline, was used. This compound was identified using LC-MS.

$C_{38}H_{25}FN_2$ $M^+$ 528.20

Synthesis of Compound 8

5.28 g (10.0 mmol) of Intermediate I-9, 1.56 g (5.0 mmol) of 4,4-dibromobiphenyl, 0.09 g (0.1 mmol) of $Pd_2(dba)_3$, 0.01 g (0.1 mmol) of $PtBu_3$, and 1.0 g (10.0 mmol) of KOtBu were dissolved in 30 mL of toluene to obtain a mixture, which was then stirred at about 85° C. for 4 hours. The reaction solution was cooled to room temperature, followed by three times of extraction with 20 mL of water and 20 mL of diethylether. The organic phase was collected and was dried using magnesium sulfate to evaporate the solvent. The residue was separated and purified using silica gel column chromatography to obtain 4.28 g of Compound 8 (Yield: 71%). This compound was identified using MS/FAB and $^1$H NMR.

$C_{64}H_{42}N_4$ cal. 1206.45, found 1207.45

$^1$H NMR ($CDCl_3$, 400 MHz) δ=7.78-7.76 (m, 2H), 7.72-7.69 (m, 4H), 7.65-7.61 (m, 5H), 7.58-7.49 (m, 22H), 7.44-7.34 (m, 15H), 7.16-7.13 (dd, 2H), 6.76 (d, 2H), 6.62-6.58 (m, 4H)

Synthesis of Compound 33

3.58 g (10.0 mmol) of Intermediate I-8, 1.81 g (5.0 mmol) of 1-bromo-4-(4-bromo-phenyl)-naphthalene, 0.09 g (0.1 mmol) of $Pd_2(dba)_3$, 0.01 g (0.1 mmol) of $PtBu_3$, and 1.0 g (10.0 mmol) of KOtBu were dissolved in 30 mL of toluene to obtain a mixture, which was then stirred at about 85° C. for 4 hours. The reaction solution was cooled to room temperature, followed by three times of extraction with 20 mL of water and 20 mL of diethylether. The organic phase was collected and was dried using magnesium sulfate to evaporate the solvent. The residue was separated and purified using silica gel column chromatography to obtain 3.66 g of Compound 33 (Yield: 80%). This compound was identified using MS/FAB and $^1$H NMR.

$C_{68}H_{44}N_4$ cal. 916.36, found 917.36

$^1$H NMR ($CDCl_3$, 400 MHz) δ=7.80-7.76 (m, 3H), 7.58-7.34 (m, 25H), 7.15 (ss, 1H), 7.09-7.03 (m, 4H), 6.96-6.88 (m, 3H), 6.73 (d, 2H), 6.67-6.61 (m, 2H), 6.38-6.34 (m, 2H), 6.21-6.17 (m, 2H)

Synthesis of Compound 34

3.58 g (10.0 mmol) of Intermediate I-8, 1.81 g (5.0 mmol) of 1-bromo-5-(4-bromo-phenyl)-naphthalene, 0.09 g (0.1 mmol) of $Pd_2(dba)_3$, 0.01 g (0.1 mmol) of $PtBu_3$, and 1.0 g (10.0 mmol) of KOtBu were dissolved in 30 mL of toluene to obtain a mixture, which was then stirred at about 85° C. for 4 hours. The reaction solution was cooled to room temperature, followed by three times of extraction with 20 mL of water and 20 mL of diethylether. The organic phase was collected and was dried using magnesium sulfate to evaporate the solvent. The residue was separated and purified using silica gel column chromatography to obtain 3.58 g of Compound 34 (Yield: 78%). This compound was identified using MS/FAB and $^1$H NMR.

$C_{68}H_{44}N_4$ cal. 916.36, found 917.55

$^1$H NMR ($CDCl_3$, 400 MHz) δ=7.81-7.75 (m, 3H), 7.58-7.53 (m, 4H), 7.47-7.28 (m, 22H), 7.10-7.03 (m, 4H), 6.94-6.92 (m, 2H), 6.76-6.73 (m, 3H), 6.66-6.62 (m, 2H), 6.38-6.34 (m, 2H), 6.21-6.17 (m, 2H)

Synthesis of Compound 45

3.58 g (10.0 mmol) of Intermediate I-8, 2.01 g (5.0 mmol) of 2,7-dibromo-9-phenylcarbazole, 0.09 g (0.1 mmol) of $Pd_2(dba)_3$, 0.01 g (0.1 mmol) of $PtBu_3$, and 1.0 g (10.0 mmol) of KOtBu were dissolved in 30 mL of toluene to obtain a mixture, which was then stirred at about 85° C. for 4 hours. The reaction solution was cooled to room temperature, followed by three times of extraction with 20 mL of water and 20 mL of diethylether. The organic phase was collected and was dried using magnesium sulfate to evaporate the solvent. The residue was separated and purified using silica gel column chromatography to obtain 3.87 g of Compound 45 (Yield: 81%). This compound was identified using MS/FAB and $^1$H NMR.

$C_{70}H_{45}N_5$ cal. 955.37, found 956.37

$^1$H NMR ($CDCl_3$, 400 MHz) δ=7.81-7.75 (m, 3H), 7.58-7.53 (m, 4H), 7.47-7.28 (m, 22H), 7.10-7.03 (m, 4H), 6.94-6.92 (m, 2H), 6.76-6.73 (m, 3H), 6.66-6.62 (m, 2H), 6.38-6.34 (m, 2H), 6.21-6.17 (m, 2H)

Synthesis of Compound 51

3.58 g (10.0 mmol) of Intermediate I-8, 2.38 g (5.0 mmol) of 2,7-dibromo-9,9-diphenyl-fluorene, 0.09 g (0.1 mmol) of $Pd_2(dba)_3$, 0.01 g (0.1 mmol) of $PtBu_3$, and 1.0 g (10.0 mmol) of KOtBu were dissolved in 30 mL of toluene to obtain a mixture, which was then stirred at about 85° C. for 4 hours. The reaction solution was cooled to room temperature, followed by three times of extraction with 20 mL of water and 20 mL of diethylether. The organic phase was collected and was dried using magnesium sulfate to evaporate the solvent. The residue was separated and purified using silica gel column chromatography to obtain 3.86 g of Compound 51 (Yield: 75%). This compound was identified using MS/FAB and $^1$H NMR.

$C_{70}H_{45}N_5$ cal. 1030.40, found 1031.40

$^1$H NMR ($CDCl_3$, 400 MHz) δ=7.78-7.75 (m, 2H), 7.74 (s, 1H), 7.72 (s, 1H), 7.65-7.63 (m, 4H), 7.58-7.46 (m, 12H), 7.40-7.33 (m, 12H), 7.28-7.25 (m, 4H), 7.11-7.06 (m, 4H), 6.90-6.88 (dd, 2H), 6.69 (d, 2H), 6.65-6.63 (m, 2H), 6.30-6.26 (m, 4H)

Synthesis of Compound 56

3.58 g (10.0 mmol) of Intermediate I-8, 1.63 g (5.0 mmol) of 2,8-dibromo-dibenzofuran, 0.09 g (0.1 mmol) of $Pd_2(dba)_3$, 0.01 g (0.1 mmol) of $PtBu_3$, and 1.0 g (10.0 mmol) of KOtBu were dissolved in 30 mL of toluene to obtain a mixture, which was then stirred at about 85° C. for 4 hours. The reaction solution was cooled to room temperature, followed by three times of extraction with 20 mL of water and 20 mL of diethylether. The organic phase was collected and was dried using magnesium sulfate to evaporate the solvent. The residue was separated and purified using silica gel column chromatography to obtain 3.61 g of Compound 56 (Yield: 82%). This compound was identified using MS/FAB and $^1H$ NMR.

$C_{70}H_{45}N_5$ cal. 880.32, found 881.32

$^1H$ NMR ($CDCl_3$, 400 MHz) δδ=7.78-7.75 (dd, 2H), 7.63-7.62 (m, 2H), 7.58-7.47 (m, 14H), 7.44-7.43 (d, 2H), 7.40-7.35 (m, 6H), 7.11-7.06 (m, 4H), 6.82-6.79 (dd, 2H), 6.74 (d, 2H), 6.67-6.63 (m, 2H), 6.41-6.38 (m, 4H)

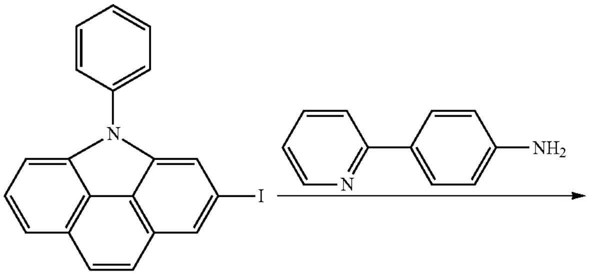

I-7

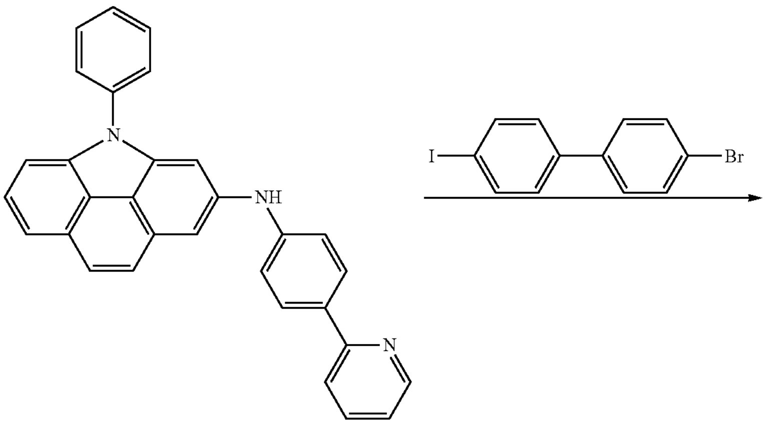

I-10

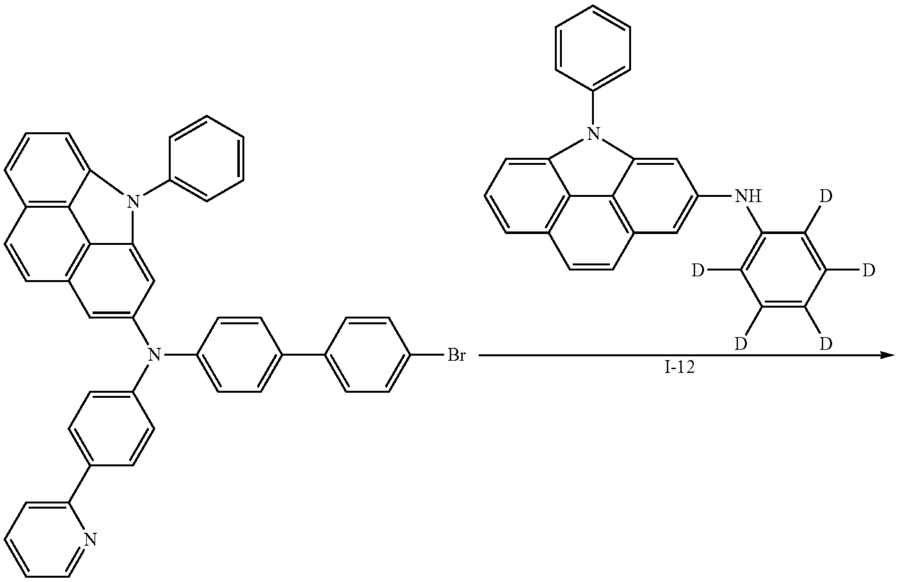

I-12

I-11

-continued

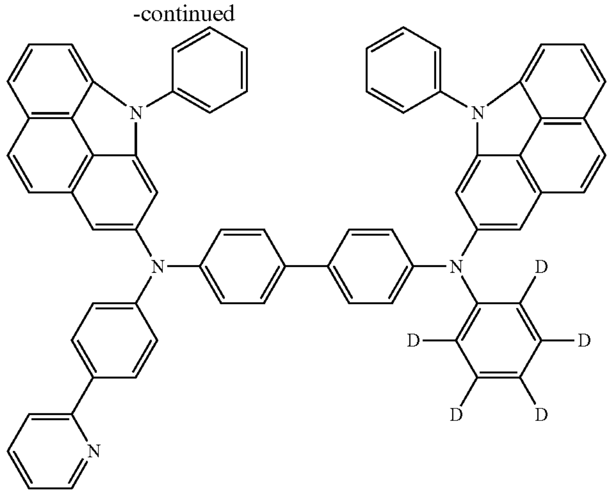

15

Synthesis of Intermediate I-10

Intermediate I-10 was synthesized in the same manner as in the synthesis of Intermediate I-8, except that 4-(pyridine-2-yl), instead of aniline, was used. This compound was identified using LC-MS.

$C_{31}H_{21}N_3$ $M^+$ 436.1

Synthesis of Intermediate I-11

Intermediate I-11 was synthesized in the same manner as in the synthesis of intermediate I-8, except that 4'-bromo-4-iodobiphenyl and Intermediate I-10, instead of Intermediate I-7 and aniline, were used. This compound was identified using LC-MS.

$C_{43}H_{28}BrN_3$ $M^+$ 666.1

Synthesis of Intermediate I-12

Intermediate I-12 was synthesized in the same manner as in the synthesis of Intermediate I-8, except that aniline-d5, instead of aniline, was used. This compound was identified using LC-MS.

$C_{26}H_{13}D_5N_2$ $M^+$ 364.1

Synthesis of Compound 15

6.66 g (10.0 mmol) of Intermediate I-11, 3.63 g (10.0 mmol) of Intermediate I-12, 0.18 g (0.2 mmol) of $Pd_2(dba)_3$, 0.02 g (0.2 mmol) of $PtBu_3$, and 2.0 g (20.0 mmol) of KOtBu were dissolved in 40 mL of toluene to obtain a mixture, which was then stirred at about 85° C. for 4 hours. The reaction solution was cooled to room temperature, followed by three times of extraction with 30 mL of water and 30 mL of diethylether. The organic phase was collected and was dried using magnesium sulfate to evaporate the solvent. The residue was separated and purified using silica gel column chromatography to obtain 7.1 g of Compound 15 (Yield: 75%). This compound was identified using MS/FAB and $^1H$ NMR.

$C_{69}H_{40}D_5N_5$ cal. 948.40, found 949.40

$^1H$ NMR ($CDCl_3$, 400 MHz) . . . 8.70-8.68 (m, 1H), 7.82-7.71 (m, 5H), 7.66-7.64 (m, 1H), 7.57-7.34 (m, 24H), 7.28-7.26 (m, 1H), 6.90-6.86 (m, 2H), 6.81-6.79 (m, 2H), 6.74-6.71 (m, 4H)

Additional compounds were synthesized according to the same synthetic pathways and the same method as described above. Analysis data of these compounds by $^1H$ NMR and MS/FAB are shown in Table 1 below.

It is obvious to one of ordinary skill in the art that other compounds not shown in Table 1 may also be synthesized based on the above-described synthetic pathways and source materials.

TABLE 1

| Compound | $^1H$ NMR ($CDCl_3$, 400 MHz) | MS/FAB found | MS/FAB calc. |
|---|---|---|---|
| 1 | δ = 7.78-7.76 (m, 2H), 7.58-7.47 (m, 12H), 7.43-7.35 (m, 8H), 7.10-7.05 (m, 4H), 6.73 (d, 2H), 6.67-6.63 (m, 2H), 6.59 (s, 4H), 6.38-6.34 (m, 4H) | 791.41 | 790.31 |
| 4 | δ = 7.77-7.75 (dd, 2H), 7.58-7.46 (m, 12H), 7.40-7.34 (m, 8H), 7.11-7.06 (m, 4H), 6.70 (d, 2H), 6.67-6.63 (m, 2H), 6.53-6.52 (m, 2H), 6.34-6.30 (m, 4H), 5.87-5.84 (dd, 2H) | 791.45 | 790.31 |
| 7 | δ = 7.78-7.76 (m, 2H), 7.58-7.34 (m, 24H), 7.10-7.05 (m, 4H), 6.75-6.71 (m, 6H), 6.71-6.62 (m, 2H), 6.38-6.34 (m, 4H) | 867.34 | 866.34 |
| 8 | δ = 7.78-7.76 (m, 2H), 7.72-7.69 (m, 4H), 7.65-7.61 (m, 5H), 7.58-7.49 (m, 22H), 7.44-7.34 (m, 15H), 7.16-7.13 (dd, 2H), 6.76 (d, 2H), 6.62-6.58 (m, 4H) | 1207.45 | 1206.45 |
| 11 | δ = 8.12-8.10 (m, 2H), 7.87-7.85 (m, 2H), 7.77-7.76 (m, 2H), 7.57-7.29 (m, 32H), 6.75-6.73 (m, 4H), 6.55-6.52 (m, 4H) | 967.47 | 966.37 |
| 15 | δ = 8.70-8.68 (m, 1H), 7.82-7.71 (m, 5H), 7.66-7.64 (m, 1H), 7.57-7.34 (m, 24H), 7.28-7.26 (m, 1H), 6.90-6.86 (m, 2H), 6.81-6.79 (m, 2H), 6.74-6.71 (m, 4H) | 949.40 | 948.40 |
| 22 | δ = 7.78-7.85 (m, 1H), 7.78-7.71 (m, 3H), 7.67-7.65 (m, 1H), 7.57-7.34 (m, 21H), 7.28 (d, 1H), 7.20-7.18 (m, 2H), 7.10-7.04 (m, 5H), 6.93-6.92 (m, 3H), 6.71-6.63 (m, 3H), 6.33-6.30 (m, 2H), 6.23-6.21 (m, 2H) | 957.35 | 956.35 |

TABLE 1-continued

| Compound | $^1H$ NMR ($CDCl_3$, 400 MHz) | MS/FAB found | MS/FAB calc. |
|---|---|---|---|
| 23 | δ = 7.77-7.76 (m, 3H), 7.58-7.47 (m, 18H), 7.43-7.42 (m, 2H), 7.40-7.34 (m, 6H), 7.27-7.24 (m, 1H), 7.10-7.05 (m, 4H), 6.73 (d, 2H), 6.70-6.62 (m, 6H), 6.38-6.34 (m, 4H) | 943.37 | 942.37 |
| 26 | δ = 7.77-7.72 (m, 4H), 7.58-7.46 (m, 12H), 7.40-7.34 (m, 8H), 7.18 (t, 2H), 7.08-7.03 (m, 4H), 6.73 (d, 2H), 6.71-6.68 (dd, 2H), 6.63-6.61 (m, 2H), 6.21-6.17 (m, 4H) | 841.33 | 840.33 |
| 28 | δ = 7.78-7.72 (m, 4H), 7.58-7.54 (m, 5H), 7.51-7.46 (m, 7H), 7.40-7.36 (m, 11H), 7.34 (d, 1H), 7.18-7.14 (t, 2H), 6.73 (d, 2H), 6.68-6.65 (m, 6H) | 891.32 | 890.32 |
| 33 | δ = 7.80-7.76 (m, 3H), 7.58-7.34 (m, 25H), 7.15 (ss, 1H), 7.09-7.03 (m, 4H), 6.96-6.88 (m, 3H), 6.73 (d, 2H), 6.67-6.61 (m, 2H), 6.38-6.34 (m, 2H), 6.21-6.17 (m, 2H) | 917.36 | 916.36 |
| 34 | δ = 7.81-7.75 (m, 3H), 7.58-7.53 (m, 4H), 7.47-7.28 (m, 22H), 7.10-7.03 (m, 4H), 6.94-6.92 (m, 2H), 6.76-6.73 (m, 3H), 6.66-6.62 (m, 2H), 6.38-6.34 (m, 2H), 6.21-6.17 (m, 2H) | 917.55 | 916.36 |
| 42 | δ = 7.78-7.75 (m, 2H), 7.58-7.47 (m, 12H), 7.44-7.43 (d, 2H), 7.40 (t, 1H), 7.37-7.35 (m, 5H), 7.11-7.08 (m, 7H), 7.04 (s, 1H), 6.71 (d, 2H), 6.66-6.63 (m, 2H), 6.53-6.52 (d, 1H), 6.50 (d, 1H), 6.41-6.38 (m, 4H), 1.37 (6H) | 907.37 | 906.37 |
| 45 | δ = 7.78-7.76 (dd, 2H), 7.72-7.69 (dd, 2H), 7.58-7.47 (m, 16H), 7.43 (d, 2H), 7.40-7.35 (m, 6H), 7.31-7.26 (m, 1H), 7.11-7.06 (m, 4H), 6.91 (d, 2H), 6.78 (d, 2H), 6.70 (d, 1H), 6.69-6.62 (m, 3H), 6.45-6.41 (m, 4H) | 956.37 | 955.37 |
| 48 | δ = 7.77-7.75 (dd, 2H), 7.63-7.45 (m, 16H), 7.40-7.35 (m, 11H), 7.32 (s, 2H), 7.12-7.06 (m, 4H), 6.77 (d, 2H), 6.72 (d, 2H), 6.67-6.62 (m, 2H), 6.41-6.38 (m, 4H) | 980.37 | 979.37 |
| 50 | δ = 7.78-7.75 (dd, 2H), 7.74 (s, 1H), 7.72 (s, 1H), 7.65-7.63 (m, 4H), 7.58-7.46 (m, 12H), 7.40-7.33 (m, 12H), 7.30-7.25 (m, 4H), 7.11-7.06 (m, 4H), 6.90-6.88 (dd, 2H), 6.69 (d, 2H), 6.67-6.63 (m, 2H), 6.30-6.26 (m, 4H) | 1047.38 | 1046.38 |
| 51 | δ = 7.78-7.75 (m, 2H), 7.74 (s, 1H), 7.72 (s, 1H), 7.65-7.63 (m, 4H), 7.58-7.46 (m, 12H), 7.40-7.33 (m, 12H), 7.28-7.25 (m, 4H), 7.11-7.06 (m, 4H), 6.90-6.88 (dd, 2H), 6.69 (d, 2H), 6.65-6.63 (m, 2H), 6.30-6.26 (m, 4H) | 1031.40 | 1030.40 |
| 52 | δ = 7.86-7.84 (ss, 1H), 7.77-7.75 (dd, 2H), 7.67-7.62 (m, 2H), 7.57-7.53 (m, 4H), 7.49-7.47 (m, 8H), 7.42 (t, 1H), 7.40-7.35 (m, 7H), 7.12-7.04 (m, 8H), 6.85 (s, 1H), 6.66-6.62 (m, 2H), 6.53-6.49 (m, 2H), 6.35-6.32 (m, 2H), 6.18-6.16 (m, 2H), 1.62 (s, 6H) | 957.39 | 956.39 |
| 53 | δ = 7.93-7.91 (m, 2H), 7.77-7.75 (m, 2H), 7.61 (ss, 2H), 7.55-7.35 (m, 22H), 7.20-7.16 (m, 2H), 7.11-7.06 (m, 4H), 6.81-6.79 (dd, 2H), 6.76-6.75 (dd, 2H), 6.67-6.63 (m, 4H), 6.60 (d, 2H), 6.35-6.32 (m, 4H) | 1029.39 | 1028.39 |
| 56 | δ = 7.78-7.75 (dd, 2H), 7.63-7.62 (m, 2H), 7.58-7.47 (m, 14H), 7.44-7.43 (d, 2H), 7.40-7.35 (m, 6H), 7.11-7.06 (m, 4H), 6.82-6.79 (dd, 2H), 6.74 (d, 2H), 6.67-6.63 (m, 2H), 6.41-6.38 (m, 4H) | 881.32 | 880.32 |

Example 1

To manufacture a first electrode (anode), a corning 15 Ω/cm$^2$ (1200 Å) ITO glass substrate was cut to a size of 50 mm×50 mm×0.7 mm and then sonicated in isopropyl alcohol and pure water each for five minutes, and then cleaned by irradiation of ultraviolet rays for 30 minutes and exposure to ozone. The resulting glass substrate was loaded into a vacuum deposition device.

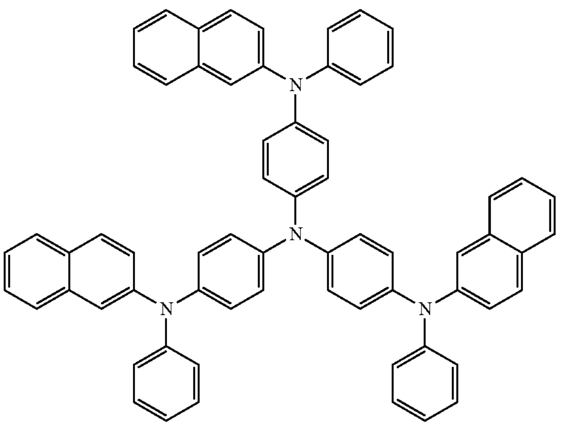

2-THATA 4,4',4'-tris(2-naphthyl(phenyl)amino)triphenylamine (2-TNATA) was vacuum-deposited on the substrate to form a HIL having a thickness of 600 Å. Subsequently, Compound 7 as a hole transporting compound was vacuum-deposited on the HIL to a form a HTL having a thickness of 300 Å.

Subsequently, 9,10-di-naphthalene-2-yl-anthracene (AND) and 4,4'-bis[2-(4-(N,N-diphenylamino)phenyl)vinyl] biphenyl (DPAVBi) were co-deposited on the HTL in a weight ratio of 98:2 to form an EML having a thickness of about 300 Å.

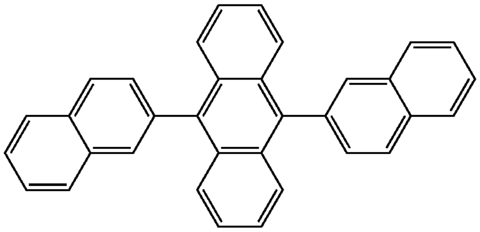

ADN

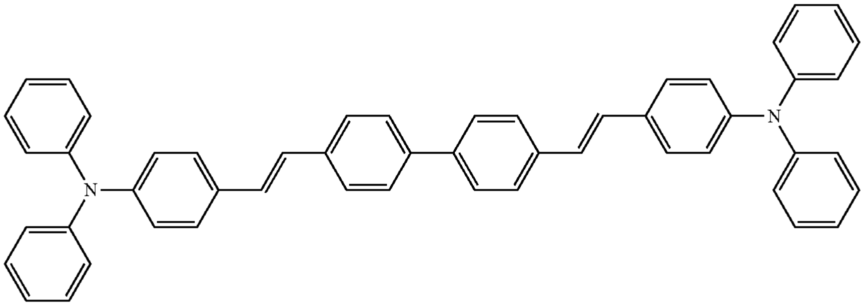

DPAVBi

Then, $Alq_3$ was deposited on the EML to form an ETL having a thickness of 300 Å, and then LiF, which is a halogenated alkali metal, was deposited on the ETL to form an EIL having a thickness of 10 Å. Then, Al was vacuum-deposited on the EIL to form a cathode having a thickness of 3000 Å, thereby forming a second electrode (cathode) and completing the manufacture of an organic light-emitting device.

The organic light-emitting device had a driving voltage of about 6.31V at a current density of 50 mA/cm$^2$, a luminosity of 3,250 cd/m$^2$, a luminescent efficiency of 6.50 cd/A, and a half life-span (hr @100 mA/cm$^2$) of about 256 hours.

Example 2

An organic light-emitting device was manufactured in the same manner as in Example 1, except that Compound 15, instead of Compound 7, was used to form the HTL.

The organic light-emitting device had a driving voltage of about 6.42V at a current density of 50 mA/cm$^2$, a luminosity of 3,255 cd/m$^2$, a luminescent efficiency of 6.57 cd/A, and a half life-span (hr @100 mA/cm$^2$) of about 260 hours.

Example 3

An organic light-emitting device was manufactured in the same manner as in Example 1, except that Compound 33, instead of Compound 7, was used to form the HTL.

The organic light-emitting device had a driving voltage of about 5.96V at a current density of 50 mA/cm$^2$, a luminosity of 3,460 cd/m$^2$, a luminescent efficiency of 6.92 cd/A, and a half life-span (hr @100 mA/cm$^2$) of about 344 hours.

Example 4

An organic light-emitting device was manufactured in the same manner as in Example 1, except that Compound 45, instead of Compound 7, was used to form the HTL.

The organic light-emitting device had a driving voltage of about 6.47V at a current density of 50 mA/cm$^2$, a luminosity of 3,280 cd/m$^2$, a luminescent efficiency of 6.56 cd/A, and a half life-span (hr @100 mA/cm$^2$) of about 282 hours.

Example 5

An organic light-emitting device was manufactured in the same manner as in Example 1, except that Compound 51, instead of Compound 7, was used to form the HTL.

The organic light-emitting device had a driving voltage of about 5.57V at a current density of 50 mA/cm$^2$, a luminosity of 3,470 cd/m$^2$, a luminescent efficiency of 6.94 cd/A, and a half life-span (hr @100 mA/cm$^2$) of about 326 hours.

Example 6

An organic light-emitting device was manufactured in the same manner as in Example 1, except that Compound 56, instead of Compound 7, was used to form the HTL.

The organic light-emitting device had a driving voltage of about 5.82V at a current density of 50 mA/cm$^2$, a luminosity of 3,440 cd/m$^2$, a luminescent efficiency of 6.88 cd/A, and a half life-span (hr @100 mA/cm$^2$) of about 318 hours.

Example 7

An organic light-emitting device was manufactured in the same manner as in Example 1, except that Compound 34, instead of well-known 2-TNATA, was used to form the HIL, and well-known 4,4'-bis[N-(1-naphthyl)-N-phenylamino]biphenyl (NPB), instead of Compound 7, was used to form the HTL.

The organic light-emitting device had a driving voltage of about 6.81V at a current density of 50 mA/cm$^2$, a luminosity of 3,210 cd/m$^2$, a luminescent efficiency of 6.42 cd/A, and a half life-span (hr @100 mA/cm$^2$) of about 236 hours.

Example 8

An organic light-emitting device was manufactured in the same manner as in Example 7, except that Compound 45, instead of Compound 34, was used to form the HIL.

The organic light-emitting device had a driving voltage of about 6.72V at a current density of 50 mA/cm$^2$, a luminosity of 3,075 cd/m$^2$, a luminescent efficiency of 6.15 cd/A, and a half life-span (hr @100 mA/cm$^2$) of about 244 hours.

Example 9

An organic light-emitting device was manufactured in the same manner as in Example 7, except that Compound 56, instead of Compound 34, was used to form the HIL.

The organic light-emitting device had a driving voltage of about 6.60V at a current density of 50 mA/cm$^2$, a luminosity of 3,120 cd/m$^2$, a luminescent efficiency of 6.24 cd/A, and a half life-span (hr @100 mA/cm$^2$) of about 252 hours.

Example 10

An organic light-emitting device was manufactured in the same manner as in Example 1, except that Compound 8, instead of well-known DPAVBi, was used to form the EML, and well-known NPB, instead of Compound 7, was used to form the HTL.

The organic light-emitting device had a driving voltage of about 6.62V at a current density of 50 mA/cm$^2$, a luminosity of 3,395 cd/m$^2$, a luminescent efficiency of 6.79 cd/A, and a half life-span (hr @100 mA/cm$^2$) of about 318 hours.

Example 11

An organic light-emitting device was manufactured in the same manner as in Example 1, except that Compound 33, instead of Compound 8, was used to form the EML.

The organic light-emitting device had a driving voltage of about 6.38V at a current density of 50 mA/cm$^2$, a luminosity of 3,295 cd/m$^2$, a luminescent efficiency of 6.59 cd/A, and a half life-span (hr @100 mA/cm$^2$) of about 306 hours.

Example 12

An organic light-emitting device was manufactured in the same manner as in Example 1, except that Compound 33, instead of Compound 7, was used to form the HTL, and Compound 8, instead of well-known DPAVBi, was used to form the EML.

The organic light-emitting device had a driving voltage of about 5.95V at a current density of 50 mA/cm$^2$, a luminosity of 3,505 cd/m$^2$, a luminescent efficiency of 7.01 cd/A, and a half life-span (hr @100 mA/cm$^2$) of about 340 hours.

Comparative Example 1

An organic light-emitting device was manufactured in the same manner as in Example 1, except that well-known 4,4'-bis[N-(1-naphthyl)-N-phenylamino]biphenyl (NPB), instead of Compound 7, was used to form the HTL.

The organic light-emitting device had a driving voltage of about 7.35V at a current density of 50 mA/cm$^2$, a luminosity of 2,065 cd/m$^2$, a luminescent efficiency of 4.13 cd/A, and a half life-span (hr @100 mA/cm$^2$) of about 145 hours.

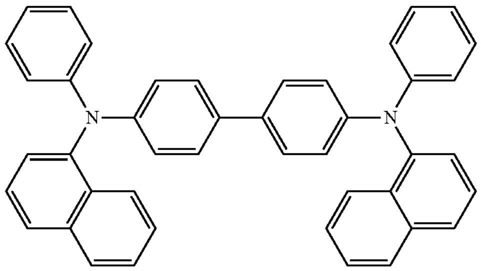

NPB

The organic light-emitting devices manufactured using the compounds represented by Formula 1 above as hole transporting materials for blue devices had lower driving voltages and much higher I-V-L characteristics, and in particular, markedly improved lifetime characteristics, as compared to those manufactured using the widely-known material NPB. The organic light-emitting devices of Examples 7, 8, and 9 using the compounds of Formula 1 above as a hole injecting material, had low driving voltages and high efficiencies, as compared with those using well-known 2-TNATA, indicating that the compound of Formula 1 above is suitable as a hole injecting material. The organic light-emitting devices of Examples 10 and 11 using the compound of Formula 1 above as a dopant for the blue EML had low driving voltages and high efficiencies as compared with those using widely known DPAVBi, indicating that the compound of Formula 1 above is suitable as a blue light-emitting material. Some main characteristics and lifetime characteristics of the organic light-emitting devices of Examples 1 to 12 and Comparative Example 1 are shown in Table 2 below.

TABLE 2

| Example | HTL/HIL/EML material | Driving voltage (V) | Current density (mA/cm$^2$) | Luminance (cd/m$^2$) | Efficiency (cd/A) | Emission color | Half-lifespan (hr @100 mA/cm$^2$) |
|---|---|---|---|---|---|---|---|
| Example 1 | Compound 7 | 6.31 | 50 | 3,250 | 6.50 | Blue | 256 hr |
| Example 2 | Compound 15 | 6.42 | 50 | 3,255 | 6.57 | Blue | 260 hr |
| Example 3 | Compound 33 | 5.96 | 50 | 3,460 | 6.92 | Blue | 344 hr |
| Example 4 | Compound 45 | 6.47 | 50 | 3,280 | 6.56 | Blue | 282 hr |
| Example 5 | Compound 51 | 5.57 | 50 | 3,470 | 6.94 | Blue | 326 hr |
| Example 6 | Compound 56 | 5.82 | 50 | 3,440 | 6.88 | Blue | 318 hr |
| Example 7 | Compound 34 | 6.81 | 50 | 3,210 | 6.42 | Blue | 236 hr |
| Example 8 | Compound 45 | 6.72 | 50 | 3,075 | 6.15 | Blue | 244 hr |
| Example 9 | Compound 56 | 6.60 | 50 | 3,120 | 6.24 | Blue | 252 hr |
| Example 10 | Compound 8 | 6.62 | 50 | 3,395 | 6.79 | Blue | 318 hr |
| Example 11 | Compound 33 | 6.38 | 50 | 3,295 | 6.59 | Blue | 306 hr |
| Example 12 | Compound 33 & Compound 8 | 5.95 | 50 | 3,505 | 7.01 | Blue | 340 hr |
| Comparative Example 1 | NPB | 7.35 | 50 | 2,065 | 4.13 | Blue | 145 hr |

As described above, according to the one or more embodiments of the present invention, the arylamine compound of Formula 1 above has improved charge transporting capability and improved light-emitting capability, and thus is suitable as a light-emitting material for fluorescent or phosphorescent devices of any color of red, green, blue, or white. Therefore, an organic light-emitting device having high efficiency, low driving voltages, high luminance, and long lifetime may be manufactured using the arylamine compound of Formula 1 above.

It should be understood that the exemplary embodiments described therein should be considered in a descriptive sense only and not for purposes of limitation. Descriptions of features or aspects within each embodiment should typically be considered as available for other similar features or aspects in other embodiments.

What is claimed is:

1. An arylamine compound represented by Formula 1 below:

<Formula 1>

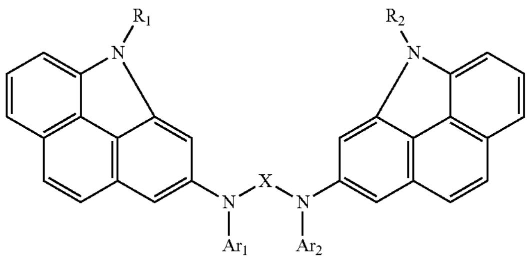

wherein, in Formula 1,

X is a substituted or unsubstituted C6-C60 arylene group, a substituted or unsubstituted C2-C60 heteroarylene group, a substituted or unsubstituted C6-C60 polycyclic group, or a divalent linking group including at least two of one or more of the following groups linked together: arylene groups, heteroarylene groups, or polycyclic groups;

$R_1$ and $R_2$ are each independently a substituted or unsubstituted C1-C60 alkyl group, a substituted or unsubstituted C3-C60 cycloalkyl group, a substituted or unsubstituted C6-C60 aryl group, a substituted or unsubstituted C2-C60 heteroaryl group, a substituted or unsubstituted C6-C60 polycyclic group, or a cyano group; and $Ar_1$ and $Ar_2$ are each independently a substituted or unsubstituted C6-C60 aryl group, a substituted or unsubstituted C2-C60 heteroaryl group, or a substituted or unsubstituted C6-C60 polycyclic group.

2. An arylamine compound of claim 1, wherein $R_1$ and $R_2$ in Formula 1 are each independently a substituted or unsubstituted C1-C30 alkyl group or

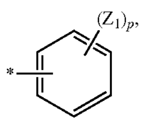

wherein $Z_1$ is a hydrogen atom, a deuterium atom, a substituted or unsubstituted C1-C20 alkyl group, a substituted or unsubstituted C6-C20 aryl group, a substituted or unsubstituted C2-C20 heteroaryl group, or a substituted or unsubstituted C6-C20 polycyclic group;

p is an integer from 1 to 5; and

* indicates a binding site.

3. An arylamine compound of claim 1, wherein X in Formula 1 is a group represented by one of Formulae 2a to 2m below:

2a

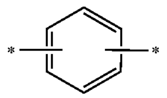

2b

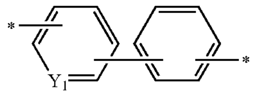

2c

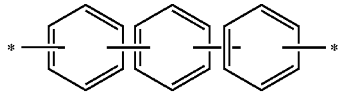

2d

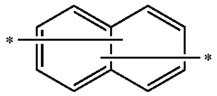

2e

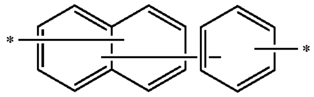

2f

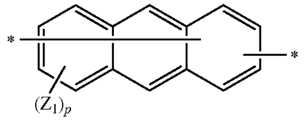

2g

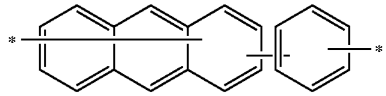

2h

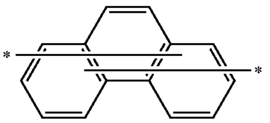

2i

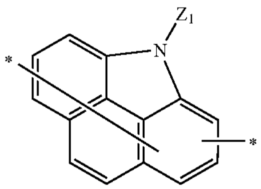

2j

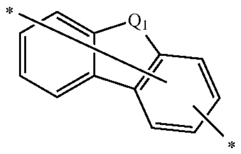

-continued

2k

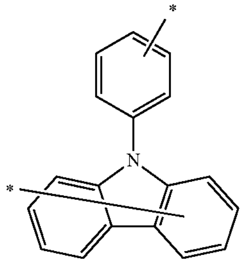

2l

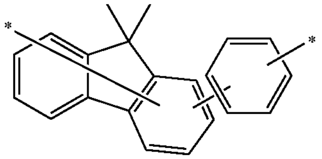

2m

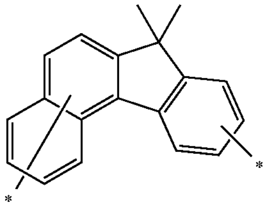

wherein, in Formulae 2a to 2m, $Y_1$ is CH or N;

$Q_1$ is a linking group represented by —$C(R_{30})(R_{31})$—, —$NR_{32}$—, —$Si(R_{33})(R_{34})$—, —S—, or —O—;

$R_{30}$ to $R_{34}$, and $Z_1$ are each independently, a hydrogen atom, a deuterium atom, a substituted or unsubstituted C1-C20 alkyl group, a substituted or unsubstituted C6-C20 aryl group, a substituted or unsubstituted C6-C20 polycyclic group, wherein $R_{30}$ and $R_{31}$ are optionally linked to form a ring;

p is an integer from 1 to 8; and

* indicates a binding site.

4. An arylamine compound of claim 1, wherein $Ar_1$ and $Ar_2$ in Formula 1 are each independently a group represented by one of Formulae 3a to 3c below:

3a

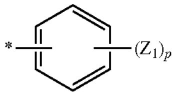

3b

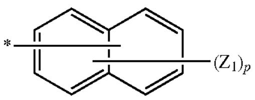

3c

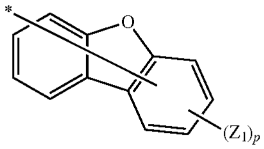

wherein, in Formulae 3a to 3c, $Z_1$ is a hydrogen atom, a deuterium atom, a substituted or unsubstituted C1-C20 alkyl group, a substituted or unsubstituted C6-C20 aryl group, an amino group substituted with a substituted or unsubstituted C6-C20 aryl group, or a substituted or unsubstituted C6-C20 polycyclic group;

p is an integer from 1 to 7; and

* indicates a binding site.

5. An arylamine compound of claim 1, wherein $Ar_1$ and $Ar_2$ in Formula 1 are linked to each other directly or via an adjacent substituent.

6. An arylamine compound of claim 1, wherein $R_1$ and $R_2$ in Formula 1 are the same.

7. An arylamine compound of claim 1, wherein the compound of Formula 1 is one of the compounds below:

7

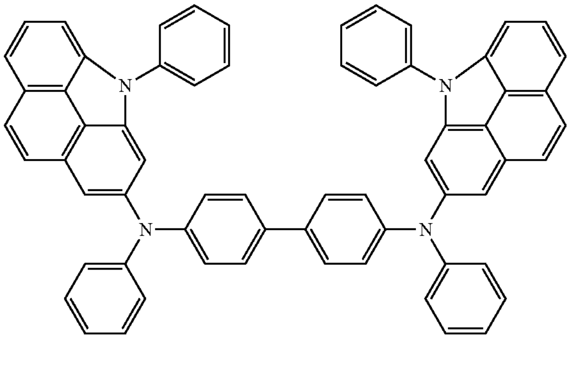

8

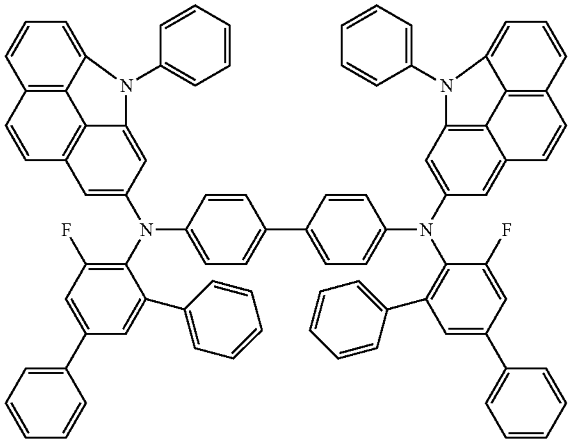

-continued
15
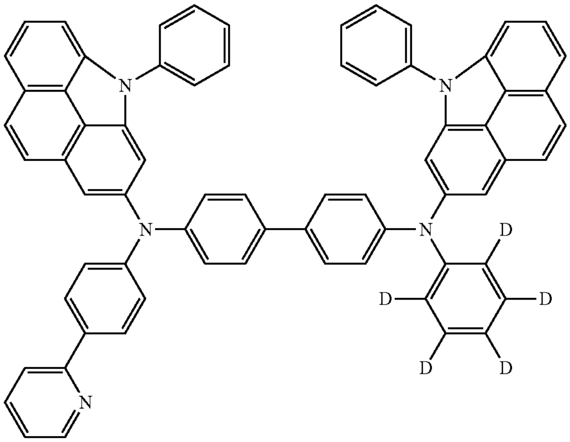
33
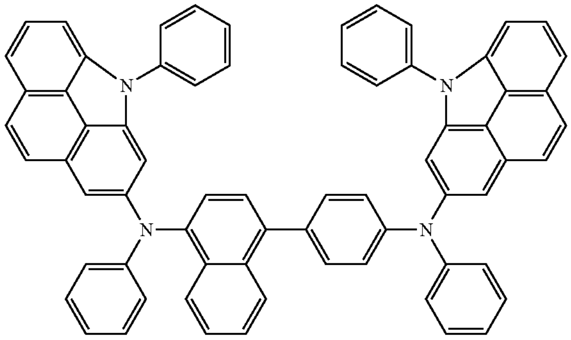
34
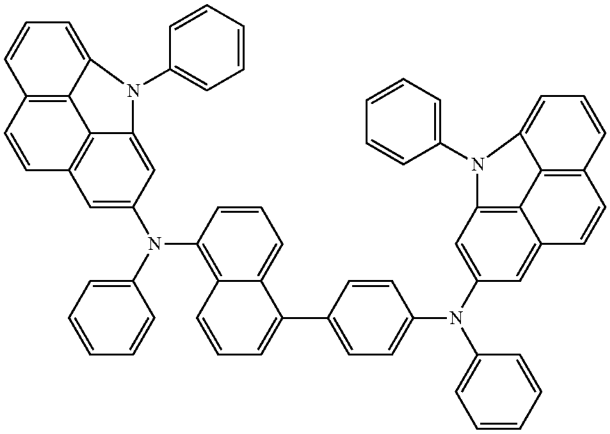
45
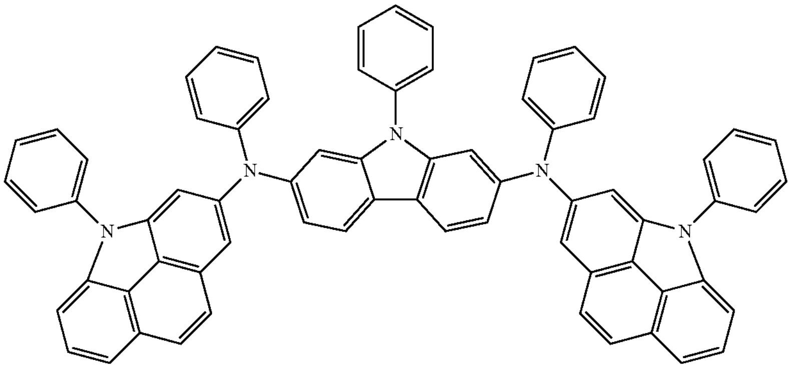
51
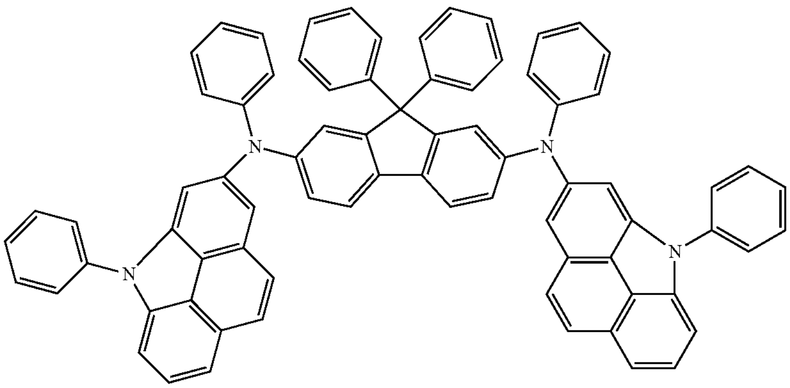

-continued

56

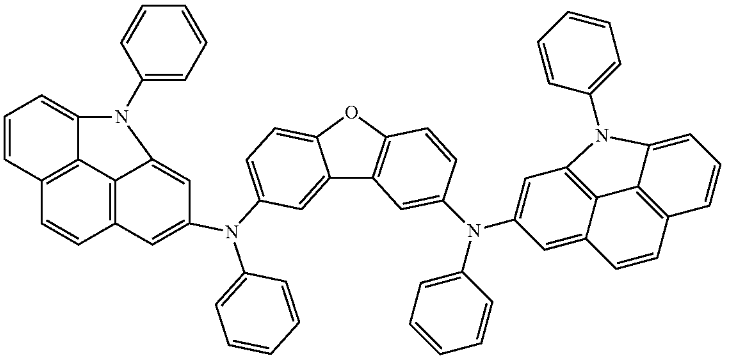

8. An organic light-emitting device comprising:

a first electrode;

a second electrode; and an organic layer disposed between the first electrode and the second electrode, the organic layer comprising an arylamine compound of claim 1.

9. The organic light-emitting device of claim 8, wherein the organic layer is a hole injection layer, a hole transport layer, a functional layer having both hole injection and hole transport capabilities, or an emission layer.

10. The organic light-emitting device of claim 8, wherein the organic light-emitting device comprises an emission layer, an electron injection layer, an electron transport layer, a functional layer having both electron injection and transport capabilities; a hole injection layer, a hole transport layer, or a functional layer having both hole injection and transport capabilities, at least one of the hole injection layer, the hole transport layer, or the functional layer having both hole injection and hole transport capabilities comprises an arylamine compound of Formula 1 of claim 1, and the emission layer comprises an arylamine compound of Formula 1 of claim 1, an anthracene-based compound, an arylamine-based compound, or a styryl-based compound.

11. The organic light-emitting device of claim 8, wherein the organic light-emitting device comprises an emission layer, an electron injection layer, an electron transport layer, a functional layer having both electron injection and transport capabilities; a hole injection layer, a hole transport layer, or a functional layer having both hole injection and transport capabilities; and at least one of the hole injection layer, the hole transport layer, or the functional layer having both hole injection and hole transport capabilities comprises an arylamine compound of Formula 1 of claim 1; and the emission layer comprises red, green, blue, and white emission layers, one or more of which comprises a phosphorescent compound.

12. The organic light-emitting device of claim 11, wherein at least one of the hole injection layer, the hole transport layer, or the functional layer having both hole injection and hole transport capabilities further comprises a charge-generating material.

13. The organic light-emitting device of claim 12, wherein the charge-generating material is a p-dopant.

14. The organic light-emitting device of claim 13, wherein the p-dopant is a quinine derivative, a metal oxide, or a cyano group-containing compound.

15. The organic light-emitting device of claim 8, wherein the organic layer further comprises an electron transport layer, and the electron transport layer comprises a metal complex.

16. The organic light-emitting device of claim 15, wherein the metal complex is a Li complex.

17. The organic light-emitting device of claim 16, wherein the metal complex is lithium quinolate (LiQ).

18. The organic light-emitting device of claim 16, wherein the metal complex is Compound 203 below:

<Compound 203>

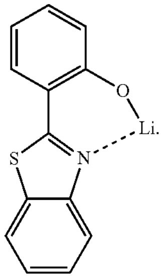

19. The organic light-emitting device of claim 8, wherein the organic layer is formed from an arylamine compound of Formula 1 of claim 1 using a wet process.

20. A flat panel display device comprising the organic light-emitting device of claim 8, wherein the first electrode of the organic light-emitting device is electrically connected to a source electrode or a drain electrode of a thin-film transistor.

* * * * *